US008940735B2

(12) United States Patent
Hoekstra et al.

(10) Patent No.: US 8,940,735 B2
(45) Date of Patent: *Jan. 27, 2015

(54) METALLOENZYME INHIBITOR COMPOUNDS

(75) Inventors: William J. Hoekstra, Durham, NC (US); Robert J. Schotzinger, Raleigh, NC (US); Gary D. Gustafson, Zionsville, IN (US)

(73) Assignee: Viamet Pharmaceuticals, Inc., Durham, NC (US)

(*) Notice: Subject to any disclaimer, the term of this patent is extended or adjusted under 35 U.S.C. 154(b) by 216 days.

This patent is subject to a terminal disclaimer.

(21) Appl. No.: 13/528,283

(22) Filed: Jun. 20, 2012

(65) Prior Publication Data

US 2013/0012503 A1  Jan. 10, 2013

Related U.S. Application Data

(60) Provisional application No. 61/500,372, filed on Jun. 23, 2011, provisional application No. 61/611,917, filed on Mar. 16, 2012.

(51) Int. Cl.
| *A01N 43/713* | (2006.01) |
| *A01N 43/78* | (2006.01) |
| *A01N 43/42* | (2006.01) |
| *A01N 43/88* | (2006.01) |
| *A01N 43/54* | (2006.01) |
| *A01N 43/60* | (2006.01) |
| *A01N 43/58* | (2006.01) |
| *C07D 417/06* | (2006.01) |
| *C07D 401/06* | (2006.01) |
| *C07D 409/06* | (2006.01) |
| *C07D 403/06* | (2006.01) |
| *A61K 31/497* | (2006.01) |
| *A61K 45/06* | (2006.01) |
| *A61K 31/41* | (2006.01) |
| *A61K 31/428* | (2006.01) |
| *A61K 31/498* | (2006.01) |
| *C07D 257/04* | (2006.01) |
| *A61K 31/427* | (2006.01) |
| *A61K 31/4709* | (2006.01) |
| *A61K 31/4439* | (2006.01) |
| *A61K 31/506* | (2006.01) |
| *A61K 31/4725* | (2006.01) |
| *A61K 31/501* | (2006.01) |

(52) U.S. Cl.
CPC .............. *A61K 45/06* (2013.01); *A61K 31/497* (2013.01); *A61K 31/41* (2013.01); *A61K 31/428* (2013.01); *A61K 31/498* (2013.01); *C07D 257/04* (2013.01); *A61K 31/427* (2013.01); *A61K 31/4709* (2013.01); *A61K 31/4439* (2013.01); *A61K 31/506* (2013.01); *C07D 401/06* (2013.01); *A61K 31/4725* (2013.01); *A61K 31/501* (2013.01); *C07D 417/06* (2013.01); *C07D 409/06* (2013.01); *C07D 403/06* (2013.01)
USPC ................... 514/229.2; 514/249; 514/252.05; 514/256; 514/269; 514/266.23; 514/314; 514/381; 514/365; 544/238; 544/333; 544/353; 548/252; 548/203

(58) Field of Classification Search
CPC .. C07D 417/06; C07D 401/06; C07D 409/06; C07D 403/06; A01N 43/713; A01N 43/78; A01N 43/42; A01N 43/88; A01N 43/54; A01N 43/60; A01N 43/58
USPC ......... 514/229.2, 249, 365, 252.05, 381, 314, 514/266.23, 256, 269; 544/238, 333, 353; 548/252, 203
See application file for complete search history.

(56) References Cited

U.S. PATENT DOCUMENTS

| 4,616,206 | A |   | 10/1986 | Bridges et al. |
| 4,960,782 | A | * | 10/1990 | Gymer et al. ................. 514/383 |
| 5,364,938 | A |   | 11/1994 | Dickinson et al. |
| 5,495,024 | A | * | 2/1996 | Itoh et al. ................... 548/267.8 |
| 6,015,825 | A |   | 1/2000 | Bell et al. |
| 8,236,962 | B2 | * | 8/2012 | Hoekstra et al. ........... 546/268.1 |
| 2006/0178415 | A1 |   | 8/2006 | Salman et al. |
| 2012/0329788 | A1 |   | 12/2012 | Hoekstra et al. |
| 2013/0005719 | A1 |   | 1/2013 | Hoekstra et al. |
| 2013/0005729 | A1 |   | 1/2013 | Hoekstra et al. |
| 2013/0005752 | A1 |   | 1/2013 | Hoekstra et al. |
| 2013/0012503 | A1 | * | 1/2013 | Hoekstra et al. ........... 514/229.2 |

FOREIGN PATENT DOCUMENTS

| WO | WO-9217474 A1 | 10/1992 |
| WO | WO-2008064311 A2 | 5/2008 |
| WO | WO-2011133875 A2 | 10/2011 |

OTHER PUBLICATIONS

Eto et al., Chemical and Pharmaceutical Bulletin; 982-990 (2000).*
Qin et al., Electrophoresis 1050-1059.*

(Continued)

*Primary Examiner* — Kamal Saeed
*Assistant Examiner* — Ebenezer O Sackey
(74) *Attorney, Agent, or Firm* — Edwards Wildman Palmer LLP; Jeffrey D. Hsi; Stephen W. Rafferty

(57) ABSTRACT

The instant invention describes compounds having metalloenzyme modulating activity, and methods of treating diseases, disorders or symptoms thereof mediated by such metalloenzymes.

22 Claims, No Drawings

(56) References Cited

OTHER PUBLICATIONS

J.H. Poupaert, Drug Design: Basic Principles and Applications, in 2 Enclopedia of Pharmaceutical Technology 1362-1369, 1367 (James Swarbrick ed., 3rd ed., 2007).

B.A. Chabner et al., Chemotherapy of Neoplastic Diseases, Neoplastic Agents in, Goodman & Gilman's: The Pharmacological Basis if Therapeutics 1315-1403, 1315 (L.L. Brunto et al., eds., 11th ed., 2006).

International Search Report for PCT/US2012/043295.

* cited by examiner

METALLOENZYME INHIBITOR COMPOUNDS

CROSS-REFERENCE TO RELATED APPLICATIONS

The present application claims priority benefit under 35 U.S.C. §119(e) of U.S. Provisional Patent Application Ser. No. 61/500,372, filed Jun. 23, 2011; and U.S. Provisional Patent Application Ser. No. 61/611,917, filed Mar. 16, 2012. The disclosures of these applications are incorporated herein by reference.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as cytochrome P450 2C9 (CYP2C9), CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

Fungicides are compounds, of natural or synthetic origin, which act to protect and cure plants against damage caused by agriculturally relevant fungi. Generally, no single fungicide is useful in all situations. Consequently, research is ongoing to produce fungicides that may have better performance, are easier to use, and cost less.

The present disclosure relates to compounds of Formula I, shown below, and their derivatives and their use as fungicides. The compounds of the present disclosure may offer protection against ascomycetes, basidiomycetes, deuteromycetes and oomycetes.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

A method of controlling a pathogen-induced disease in a plant that is at risk of being diseased from the pathogen comprising contacting one of the plant and an area adjacent to the plant with a composition of Formula I, or salt, solvate, hydrate or prodrug thereof, wherein:

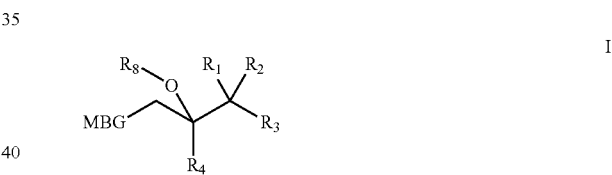

MBG is optionally substituted tetrazolyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'-OCH$_2$CF$_3$ or 4'-F, or heteroaryl, which may be optionally substituted with 1, 2 or 3 independent $R_5$;

$R_4$ is aryl, heteroaryl, alkyl or cycloalkyl, optionally substituted with 0, 1, 2 or 3 independent $R_6$;

each $R_5$ is independently H, halo, aryl optionally substituted with 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alkylaryl, arylalkynyl, arylalkyl, cycloalkyl, halocycloalkyl, thioalkyl, SF$_3$, SF$_6$, SCN, SO$_2$R$_7$, C(O)alkyl, C(O)OH, C(O)Oalkyl;

each $R_6$ is independently alkyl, thioalkyl, cyano, haloalkyl, hydroxy, alkoxy, halo, haloalkoxy, —C(O)alkyl, —C(O)OH, —C(O)Oalkyl, SF$_3$, SF$_6$, SCN, SO$_3$H; and SO$_2$R$_7$;

$R_7$ is independently alkyl, aryl, substituted aryl, heteroaryl or substituted heteroaryl;

$R_8$ is H, —Si(R$_9$)$_3$, —P(O)(OH)$_2$, —CH$_2$—O—P(O)(OH)$_2$, or —C(O)alkyl optionally substituted with amino;

$R_9$ is independently alkyl or aryl;

and wherein R₃ is not 2-pyridyl optionally substituted with 1, 2 or 3 independent R₅.

Other aspects are a compound of the formulae herein:
wherein R₁ is fluoro;
wherein R₂ is fluoro;
wherein R₁ and R₂ are fluoro;
wherein R₄ is phenyl optionally substituted with 0, 1, 2 or 3 independent R₆;
wherein R₄ is phenyl optionally substituted with 0, 1, 2 or 3 independent halo;
wherein R₄ is phenyl optionally substituted with 0, 1, 2 or 3 independent fluoro;
wherein R₄ is 2,4-difluorophenyl;
wherein R₅ is halo;
wherein R₃ is heteroaryl other than 2-pyridyl, optionally substituted with 1, 2 or 3 independent R₅;
wherein at least one R₅ is halo;
wherein:
  R₁ is fluoro;
  R₂ is fluoro;
  R₄ is 2,4-difluorophenyl; and
  R₃ is heteroaryl other than 2-pyridyl, substituted with 1, 2 or 3 independent R₅;
wherein:
  R₁ is fluoro;
  R₂ is fluoro;
  R₄ is 2,4-difluorophenyl; and
  R₃ is bicyclic heteroaryl substituted with 1, 2 or 3 independent R₅;
wherein R₃ is 2-quinolinyl substituted with 1, 2 or 3 independent R₅;
wherein MBG is optionally substituted tetrazolyl or optionally substituted triazolyl;
wherein MBG is 1H-tetrazol-1-yl, 2H-tetrazol-2-yl, 4H-1,2,4-triazol-4-yl, or 1H-1,2,4-triazol-1-yl;
wherein MBG is 1H-tetrazol-1-yl, or 2H-tetrazol-2-yl;
wherein MBG is 4H-1,2,4-triazol-4-yl, or 1H-1,2,4-triazol-1-yl;
wherein R₃ is thienyl, thiazolyl, quinolinyl, pyridyl, benzothiazolyl, pyrimidinyl, quinoxalinyl, pyrazinyl, or pyridiazinyl, each optionally substituted with 1, 2 or 3 independent R₅;
wherein:
  R₁ is fluoro;
  R₂ is fluoro;
  R₄ is 2,4-difluorophenyl; and
  R₃ is thienyl, thiazolyl, quinolinyl, pyridyl, benzothiazolyl, pyrimidinyl, quinoxalinyl, pyrazinyl, or pyridiazinyl, each optionally substituted with 1, 2 or 3 independent R₅;
wherein R₃ is thienyl, thiazolyl, quinolinyl, pyridyl, benzothiazolyl, pyrimidinyl, quinoxalinyl, pyrazinyl, or pyridiazinyl, each optionally substituted with 1, 2 or 3 independent alkyl, alkenyl, alkoxy, halo, cyano, haloalkyl, haloalkoxy, alkyl substituted with halophenyl, alkynyl substituted with halophenyl, or phenyl substituted with haloalkyl, haloalkoxy, halo, or cyano.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi-cation interactions, pi-anion interactions, dipole-dipole interactions, ion-dipole interactions. In one aspect, the compound is identified as having a bonding interaction with the metal via the 1-tetrazolyl moiety; in another aspect, the compound is identified as having a bonding interaction with the metal via the N2 of the 1-tetrazolyl moiety; in another aspect, the compound is identified as having a bonding interaction with the metal via the N3 of the 1-tetrazolyl moiety; in another aspect, the compound is identified as having a bonding interaction with the metal via the N4 of the 1-tetrazolyl moiety. In one aspect, the compound is identified as having a bonding interaction with the metal via the 4-triazolyl moiety; in another aspect, the compound is identified as having a bonding interaction with the metal via the N1 of the 4-triazolyl moiety; in another aspect, the compound is identified as having a bonding interaction with the metal via the N2 of the 4-tetrazolyl moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson, John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of Formula I (and pharmaceutically and agriculturally acceptable salts, solvates, or hydrates thereof)

1-(5-Chlorothiophen-2-yl)-2-(2,4-difluorophenyl)-1,1-difluoro-3-(1H-tetrazol-1-yl)propan-2-ol (1);
1-(4-Bromothiazol-2-yl)-2-(2,4-difluorophenyl)-1,1-difluoro-3-(1H-tetrazol-1-yl)propan-2-ol (2);
4-(2-(2-(2,4-Difluorophenyl)-1,1-difluoro-2-hydroxy-3-(1H-tetrazol-1-yl)propyl)thiazol-4-yl)benzonitrile (3);
1-(6-Chloroquinolin-2-yl)-2-(2,4-difluorophenyl)-1,1-difluoro-3-(1H-tetrazol-1-yl)propan-2-ol (4);
2-(2,4-Difluorophenyl)-1,1-difluoro-1-(quinolin-2-yl)-3-(1H-tetrazol-1-yl)propan-2-ol (5);
1-(Benzo[d]thiazol-2-yl)-2-(2,4-difluorophenyl)-1,1-difluoro-3-(1H-tetrazol-1-yl)propan-2-ol (6);
2-(2,4-Difluorophenyl)-1,1-difluoro-1-(pyrimidin-2-yl)-3-(1H-tetrazol-1-yl)propan-2-ol (7);
2-(4-Chloro-2-fluorophenyl)-1-(6-chloroquinolin-2-yl)-1,1-difluoro-3-(1H-tetrazol-1-yl)propan-2-ol (8);
1-(6-Bromoquinolin-2-yl)-2-(2,4-difluorophenyl)-1,1-difluoro-3-(1H-tetrazol-1-yl)propan-2-ol (9);
1-(6-Chloroquinoxalin-2-yl)-2-(2,4-difluorophenyl)-1,1-difluoro-3-(1H-tetrazol-1-yl)propan-2-ol (10);
1-(6-Chlorobenzo[d]thiazol-2-yl)-2-(2,4-difluorophenyl)-1,1-difluoro-3-(1H-tetrazol-1-yl)propan-2-ol (11);
2-(2,4-Difluorophenyl)-1,1-difluoro-3-(1H-tetrazol-1-yl)-1-(thiazol-2-yl)propan-2-ol (12);
1-(5-Bromothiophen-2-yl)-2-(2,4-difluorophenyl)-1,1-difluoro-3-(1H-tetrazol-1-yl)propan-2-ol (13);
2-(2,4-Difluorophenyl)-1,1-difluoro-3-(1H-tetrazol-1-yl)-1-(thiophen-2-yl)propan-2-ol (14);
1-(6-Chloroquinolin-2-yl)-1,1-difluoro-2-(4-methoxyphenyl)-3-(1H-tetrazol-1-yl)propan-2-ol (15);
1-(6-Chloroquinolin-2-yl)-2-(2,4-difluorophenyl)-1,1-difluoro-3-(2H-tetrazol-2-yl)propan-2-ol (16);
2-(2,4-Difluorophenyl)-1,1-difluoro-1-(6-fluoroquinolin-2-yl)-3-(1H-tetrazol-1-yl)propan-2-ol (17);
2-(2,4-Difluorophenyl)-1,1-difluoro-3-(1H-tetrazol-1-yl)-1-(6-(trifluoromethyl)quinolin-2-yl)propan-2-ol (18);
2-(2,4-Difluorophenyl)-1,1-difluoro-3-(1H-tetrazol-1-yl)-1-(6-(2,2,2-trifluoroethoxy)quinolin-2-yl)propan-2-ol (19);

1-(6-Chloroquinolin-2-yl)-1,1-difluoro-2-(2-fluoro-4-(trifluoromethyl)phenyl)-3-(1H-tetrazol-1-yl)propan-2-ol (20);
2-(2,4-Difluorophenyl)-1,1-difluoro-3-(1H-tetrazol-1-yl)-1-(6-(trifluoromethoxy)quinolin-2-yl)propan-2-ol (21);
2-(2-Chloro-4-(trifluoromethyl)phenyl)-1-(6-chloroquinolin-2-yl)-1,1-difluoro-3-(1H-tetrazol-1-yl)propan-2-ol (22);
1-(6-Chloroquinolin-2-yl)-2-(3,4-difluorophenyl)-1,1-difluoro-3-(1H-tetrazol-1-yl)propan-2-ol (23);
2-(2-(2,4-Difluorophenyl)-1,1-difluoro-2-hydroxy-3-(1H-tetrazol-1-yl)propyl)quinoline-6-carbonitrile (24);
1-(6-(Difluoromethyl)quinolin-2-yl)-2-(2,4-difluorophenyl)-1,1-difluoro-3-(1H-tetrazol-1-yl)propan-2-ol (25);
2-(2,4-Difluorophenyl)-1,1-difluoro-1-(6-methylquinolin-2-yl)-3-(1H-tetrazol-1-yl)propan-2-ol (26);
1-(6-Bromobenzo[d]thiazol-2-yl)-2-(2,4-difluorophenyl)-1,1-difluoro-3-(1H-tetrazol-1-yl)propan-2-ol (27);
1-(6-Chloroquinolin-2-yl)-2-(2,5-difluorophenyl)-1,1-difluoro-3-(2H-tetrazol-2-yl)propan-2-ol (28);
1-(5,6-Dichloroquinolin-2-yl)-2-(2,4-difluorophenyl)-1,1-difluoro-3-(1H-tetrazol-1-yl)propan-2-ol (29);
2-(2,4-Difluorophenyl)-1,1-difluoro-3-(1H-tetrazol-1-yl)-1-(5-(2,2,2-trifluoroethoxy)quinolin-2-yl)propan-2-ol (30);
1-(5-Chloroquinolin-2-yl)-2-(2,4-difluorophenyl)-1,1-difluoro-3-(1H-tetrazol-1-yl)propan-2-ol (31);
1-(6-Chloroquinolin-2-yl)-1,1-difluoro-2-(4-fluorophenyl)-3-(1H-tetrazol-1-yl)propan-2-ol (32);
1-(6-Cloroquinolin-2-yl)-2-(2,4-difluorophenyl)-1,1-difluoro-3-(1H-1,2,4-triazol-1-yl)propan-2-ol (33);
2-(4-Chloro-2-fluorophenyl)-1-(6-chloroquinoxalin-2-yl)-1,1-difluoro-3-(1H-tetrazol-1-yl)propan-2-ol (34);
1-(6-Chloroquinolin-2-yl)-2-(2,4-difluorophenyl)-1,1-difluoro-3-(4H-1,2,4-triazol-4-yl)propan-2-ol (35);
2-(2,4-Difluorophenyl)-1,1-difluoro-3-(1H-tetrazol-1-yl)-1-(6-(4-(2,2,2-trifluoroethoxy)phenyl)pyridin-3-yl)propan-2-ol (36);
1-(7-Chloroisoquinolin-3-yl)-2-(2,4-difluorophenyl)-1,1-difluoro-3-(1H-tetrazol-1-yl)propan-2-ol (37);
1-(6-Bromoquinoxalin-2-yl)-2-(2,4-difluorophenyl)-1,1-difluoro-3-(1H-tetrazol-1-yl)propan-2-ol (38);
1-(5-(4-(Difluoromethoxy)phenyl)pyrazin-2-yl)-2-(2,4-difluorophenyl)-1,1-difluoro-3-(1H-tetrazol-1-yl)propan-2-ol (39);
1-(5-(4-Chlorophenyl)pyrazin-2-yl)-2-(2,4-difluorophenyl)-1,1-difluoro-3-(1H-tetrazol-1-yl)propan-2-ol (40);
2-(2,4-Difluorophenyl)-1,1-difluoro-3-(1H-tetrazol-1-yl)-1-(5-(4-(2,2,2-trifluoroethoxy)phenyl)pyrazin-2-yl)propan-2-ol (41);
2-(2,4-Difluorophenyl)-1,1-difluoro-3-(1H-tetrazol-1-yl)-1-(5-(4-(trifluoromethoxy)phenyl)pyrazin-2-yl)propan-2-ol (42);
1-(5-(4-Bromophenyl)pyrazin-2-yl)-2-(2,4-difluorophenyl)-1,1-difluoro-3-(1H-tetrazol-1-yl)propan-2-ol (43);
2-(2,4-Difluorophenyl)-1-(5-(3,4-difluorophenyl)pyrazin-2-yl)-1,1-difluoro-3-(1H-tetrazol-1-yl)propan-2-ol (44);
1,1-Difluoro-2-(4-fluorophenyl)-3-(1H-tetrazol-1-yl)-1-(5-(4-(trifluoromethoxy)phenyl)pyrazin-2-yl)propan-2-ol (45);
2-(2,4-Difluorophenyl)-1,1-difluoro-1-(5-(4-fluorophenyl)pyrazin-2-yl)-3-(1H-tetrazol-1-yl)propan-2-ol (46);
2-(2,4-Difluorophenyl)-1,1-difluoro-1-(5-(4-fluorophenyl)pyrazin-2-yl)-3-(2H-tetrazol-2-yl)propan-2-ol (47);
2-(2,4-Difluorophenyl)-1,1-difluoro-1-(5-(4-methoxyphenyl)pyrazin-2-yl)-3-(1H-tetrazol-1-yl)propan-2-ol (48);
1-(5-Chloropyrazin-2-yl)-2-(2,4-difluorophenyl)-1,1-difluoro-3-(1H-tetrazol-1-yl)propan-2-ol (49);
2-(2,4-Difluorophenyl)-1,1-difluoro-1-(5-((4-fluorophenyl)ethynyl)pyrazin-2-yl)-3-(1H-tetrazol-1-yl)propan-2-ol (50);
2-(2,4-Difluorophenyl)-1,1-difluoro-1-(5-((4-fluorophenyl)ethynyl)pyrazin-2-yl)-3-(2H-tetrazol-2-yl)propan-2-ol (51);
2-(2,4-Difluorophenyl)-1,1-difluoro-1-(5-(4-fluorophenethyl)pyrazin-2-yl)-3-(1H-tetrazol-1-yl)propan-2-ol (52);
2-(2,4-Difluorophenyl)-1,1-difluoro-1-(5-(4-fluorophenethyl)pyrazin-2-yl)-3-(2H-tetrazol-2-yl)propan-2-ol (53);
2-(2,4-Difluorophenyl)-1,1-difluoro-3-(1H-tetrazol-1-yl)-1-(6-(trifluoromethoxy)quinoxalin-2-yl)propan-2-ol (54);
2-(2,4-Difluorophenyl)-1,1-difluoro-1-(6-fluoroquinoxalin-2-yl)-3-(1H-tetrazol-1-yl)propan-2-ol (55);
2-(2,4-Difluorophenyl)-1,1-difluoro-3-(1H-tetrazol-1-yl)-1-(6-(4-(trifluoromethyl)phenyl)pyridazin-3-yl)propan-2-ol (56);
2-(2,4-Difluorophenyl)-1,1-difluoro-3-(1H-tetrazol-1-yl)-1-(6-(4-(trifluoromethoxy)phenyl)pyridazin-3-yl)propan-2-ol (57);
2-(2,4-Difluorophenyl)-1,1-difluoro-1-(6-(4-fluorophenyl)pyridazin-3-yl)-3-(1H-tetrazol-1-yl)propan-2-ol (58);
2-(2,4-Difluorophenyl)-1,1-difluoro-3-(1H-tetrazol-1-yl)-1-(6-vinylquinoxalin-2-yl)propan-2-ol (59);
2-(2,4-Difluorophenyl)-1,1-difluoro-3-(1H-tetrazol-1-yl)-1-(4'-(2,2,2-trifluoroethoxy)-[1,1'-biphenyl]-4-yl)propan-2-ol (60);
2-(2,4-Difluorophenyl)-1,1-difluoro-1-(4'-fluoro-[1,1'-biphenyl]-4-yl)-3-(1H-tetrazol-1-yl)propan-2-ol (61).

In another aspect, the invention provides an agricultural composition comprising the compound of Formula I and an agriculturally acceptable carrier.

In other aspects, the invention provides a compound of any of the formulae herein, wherein the compound inhibits (or is identified to inhibit) lanosterol demethylase (CYP51).

In other aspects, the invention provides a compound of any of the formulae herein, wherein the compound is identified as having an activity range against a target organism (e.g., *C. albicans* minimum inhibitory concentration (MIC)<0.25 micrograms per milliliter (µg/mL); *S. tritici* minimum inhibitory concentration (MIC)<0.5 micrograms per milliliter (µg/mL); e.g., *P. triticina* minimum inhibitory concentration (MIC)<0.5 micrograms per milliliter (µg/mL).

In another aspect, the invention provides a pharmaceutical composition comprising the compound of Formula I and a pharmaceutically acceptable carrier.

In other aspects, the invention provides a method of modulating metalloenzyme activity in a subject, comprising contacting the subject with a compound of Formula I, in an amount and under conditions sufficient to modulate metalloenzyme activity.

In one aspect, the invention provides a method of treating a subject suffering from or susceptible to a metalloenzyme-related disorder or disease, comprising administering to the subject an effective amount of a compound or pharmaceutical composition of Formula I.

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of Formula I, such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of Formula I, such that metalloenzyme activity in said subject is modulated (e.g., down regulated, inhibited).

The methods herein include those wherein the disease or disorder is mediated by any of 4-hydroxyphenyl pyruvate dioxygenase, 5-lipoxygenase, adenosine deaminase, alcohol dehydrogenase, aminopeptidase N, angiotensin converting enzyme, aromatase (CYP19), calcineurin, carbamoyl phosphate synthetase, carbonic anhydrase family, catechol-O-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesteraseIV, phosphodiesteraseV, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is mediated by any of 1-deoxy-D-xylulose-5-phosphate reductoisomerase (DXR), 17-alpha hydroxylase (CYP17), aldosterone synthase (CYP11B2), aminopeptidase P, anthrax lethal factor, arginase, beta-lactamase, cytochrome P450 2A6, D-Ala D-Ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesteraseVII, relaxase, retinoic acid hydroxylase (CYP26), TNF-alpha converting enzyme (TACE), UDP-(3-O-(R-3-hydroxymyristoyl))-N-acetylglucosamine deacetylase (LpxC), vascular adhesion protein-1 (VAP-1), or vitamin D hydroxylase (CYP24).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic fungal infection, skin structure fungal infection, mucosal fungal infection, or onychomycosis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Another aspect of the invention is a composition comprising a compound of a formulae herein (e.g., Formula I) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically or agriculturally effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 micrograms per kilogram (µg/kg) to about 200 milligrams per kilogram (mg/kg), preferably about 0.01 mg/kg to about 200 mg/kg, more preferably about 0.015 mg/kg to about 30 mg/kg of body weight. In other embodiments, the therapeutically effect amount may range from about 1.0 picomolar (pM) to about 10 micromolar (µM). The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per day for between about 1 to 10 weeks, preferably between about 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not minor images of one another.

The term "enantiomers" refers to two stereoisomers of a compound which are non-superimposable minor images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkyl-amino loweralkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of a metalloenzyme, as compared to the activity of a metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used throughout this specification, the term 'R' refers to the group consisting of $C_{1-8}$ alkyl, $C_{3-8}$ alkenyl or $C_{3-8}$ alkynyl, unless stated otherwise.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —OR substituent.

As used herein, the term "halogen", "hal" or "halo" means —F, —Cl, —Br or —I.

The term "haloalkoxy" refers to an —OR substituent where R is fully or partially substituted with Cl, F, I or Br or any combination thereof. Examples of haloalkoxy groups include trifluoromethoxy, and 2,2,2-trifluoroethoxy.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remaining ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd; Jahnisch, K. et al., *Angew. Chem. Int. Ed. Engl.* 2004, 43, 406; and references therein). Additional reaction schemes and protocols may be determined by the skilled artisan by use of commercially available structure-searchable database software, for instance, SciFinder® (Chemical Abstracts Service (CAS®) division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

In another aspect, the invention provides a method of synthesizing a compound of formula I (or any of the formulae herein) as described herein. Another embodiment is a method of making a compound of any of the formulae herein using any one, or combination of, reactions delineated herein. The method can include the use of one or more intermediates or chemical reagents delineated herein.

Methods of Treatment

In one aspect, the invention provides a method of modulating the metalloenzyme activity of a cell in a subject, comprising contacting the subject with a compound of any of the formulae herein (e.g., Formula I), in an amount and under conditions sufficient to modulate metalloenzyme activity.

In one embodiment, the modulation is inhibition.

In another aspect, the invention provides a method of treating a subject suffering from or susceptible to a metalloenzyme-mediated disorder or disease, comprising administering to the subject an effective amount of a compound of any of the formulae herein (e.g., Formula I) or pharmaceutical or agricultural composition thereof.

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound of any of the formulae herein (e.g., Formula I) or pharmaceutical or agricultural composition thereof, such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is prostate cancer, breast cancer, inflammatory bowel disease, psoriasis, systemic fungal infection, skin structure fungal infection, mucosal fungal infection, and onychomycosis.

In certain embodiments, the subject is a mammal, preferably a primate or human.

In another embodiment, the invention provides a method as described above, wherein the effective amount of the compound of any of the formulae herein (e.g., Formula I) is as described above.

In another embodiment, the invention provides a method as described above, wherein the compound of any of the formulae herein (e.g., Formula I) is administered intravenously, intramuscularly, subcutaneously, intracerebroventricularly, orally or topically.

In other embodiments, the invention provides a method as described above, wherein the compound of any of the formulae herein (e.g., Formula I) is administered alone or in combination with one or more other therapeutics. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, opthalmologic disease agent, central nervous system (CNS) disease agent, urologic disease agent, or gastrointestinal disease agent.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of any of the formulae herein (e.g., Formula I) and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, antiinflammatory agent, chemotherapeutic agent, an anti-angiogenesis agent, cytotoxic agent, an anti-proliferation agent, metabolic disease agent, opthalmologic disease agent, central nervous system (CNS) disease agent, urologic disease agent, or gastrointestinal disease agent.

In one aspect, the invention provides a kit comprising an effective amount of a compound of any of the formulae herein (e.g., Formula I), in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *J. Pharm. Sci.* 1977, 66, 1-19). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intracerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cottonseed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and Echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making, levigating, emulsifying, encapsulating, entrapping or lyophilization processes. The compositions can be formulated in a conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen-free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/mL); benzalkonium chloride (0.1-0.2 mg/mL); polysorbate 80 (TWEEN® 80; 0.5-5 mg/mL); carboxymethylcellulose sodium or microcrystalline cellulose (1-15 mg/mL); phenylethanol (1-4 mg/mL); and dextrose (20-50 mg/mL). The pH of the final suspension can be adjusted to range from about pH 5 to pH 7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in an in vitro assay, such as the in vitro fungal MIC or minimal fungicidal concentration (MFC) and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, 12th edition, McGraw-Hill Professional, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

Compounds of Formula I may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Compounds of Formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Suitable salts include those derived from alkali or alkaline earth metals and those derived from ammonia and amines. Preferred cations include sodium, potassium, magnesium, and aminium cations of the formula:

wherein $R^{10}$, $R^{11}$, $R^{12}$ and $R^{13}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{10}$, $R^{11}$, $R^{12}$ and $R^{13}$ are sterically compatible. Additionally, any two of $R^{10}$, $R^{11}$, $R^{12}$ and $R^{13}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide Amine salts are often preferred forms of the compounds of Formula I because they are water-soluble and lend themselves to the preparation of desirable aqueous based herbicidal compositions.

The compounds and compositions herein can be used in methods of modulating metalloenzyme activity in a microorganism on a plant comprising contacting a compound (or composition) herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

One aspect is a method of treating or preventing a fungal disease or disorder in or on a plant comprising contacting a compound (or composition) of any of the formulae herein with the plant. Another aspect is a method of treating or preventing fungi growth in or on a plant comprising contacting a compound (or composition) of any of the formulae herein with the plant. Another aspect is a method of inhibiting microorganisms in or on a plant comprising contacting a compound (or composition) of any of the formulae herein with the plant.

The compounds and compositions herein may be used in methods of preventing or controlling pathogen induced diseases on a plant comprising contacting a compound herein with the plant (e.g., seed, seedling, grass, weed, grain) or an area adjacent to the plant. The compounds and compositions herein may be used to treat a plant, field or other agricultural area by administering the compound or composition (e.g., contacting, applying, spraying, atomizing, dusting, etc.) to the subject plant, field or other agricultural area. The administration may be either pre- or post-emergence. The administration may be either as a treatment or preventative regimen. As such, the compounds, compositions and agricultural uses herein include lawn, turf, ornamental vegetation, home and garden, farming, range and pasture applications. The pathogen may be any on a plant and include those delineated herein.

One embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants.

The compounds herein can be used alone or in combination with other agriculturally active agents. The use of the compounds or compositions (and the compositions) herein can further comprise an additional active agent such as an azole fungicide selected from epoxiconazole, tebuconazole, fluquinconazole, flutriafol, metconazole, myclobutanil, cycproconazole, prothioconazole and propiconazole.

The use of the compounds or compositions (and the compositions) herein can further comprise an additional active agent such as an azole fungicide selected from the group trifloxystrobin, pyraclostrobin, orysastrobin, fluoxastrobin and azoxystrobin.

Preferably, the compounds of the present disclosure are applied in the form of a formulation, comprising one or more of the compounds of Formula I with an agriculturally or phytologically acceptable carrier. The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The present disclosure contemplates all vehicles by which one or more of the compounds may be formulated for delivery and use as a fungicide. Typically, formulations are applied as aqueous suspensions or emulsions. Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid, it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm A suitable solvent is a solvent in which the compound is substantially or completely soluble. Such formulations may also be prepared by making a dough or paste of the carrier and the compound and solvent, and crushing and drying to obtain the desired granular particle.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cottonseed, walnut, palm, castor, earth almond, hazelnut, avocado, sesame, croton tiglium, cacao, linseed, rapeseed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodium carboxymethylcellulose, ethyl cellulose, hydroxypropyl methyl cellulose, and mixtures thereof.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, laminarin, kasugamycin, kasugamycin hydrochloride hydrate, kresoxim-methyl, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hyprorene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, novifluron, ometheoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, B CPC, beflubutamid, benazolin, bencarbazone, benfluralin, benfuresate, bensulfuron, bensulide, bentazon, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vemolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

The compositions of Formula I may be effective against pathogen induced diseases where the plant fungal pathogen belonging to at least one genera selected from *Blumeria, Podosphaera, Sphaerotheca, Uncinula, Erysiphe, Puccinia, Phakopsora, Gymnosporangium, Hemileia, Uromyces, Alternaria, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminthosporium, Stagonospora, Exserohilum*, and *Pyricularia*. Pathogens such as *Venturia inaequalis, Septoria tritici, Cercospora beticola, Cercospora arachidicola, Colletotrichum lagenarium, Puccinia graminis* f. sp. *tritici, Puccinia recondita tritici, Uncinula necator, Blumeria graminis*, and *Mycosphaerella fijiensis* may be controlled by compositions of Formula I. Additionally, the compositions of Formula I may be effective in preventing or controlling diseases including apple scab, speckled leaf blotch of wheat, leaf spot of sugarbeets, leaf spot of peanut, cucumber anthracnose, wheat leaf rust, grape powdery mildew, wheat powdery mildew, and black sigatoka.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound of Formula I; such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

The compounds of the present disclosure may be effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Azole Targets

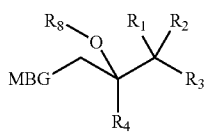

I

Syntheses of azole targets (Formula I) may be accomplished using the example synthesis that is shown below (Scheme 1). A broad range of heterocycles may be prepared starting from functionalized halo-aromatic starting materials (e.g. A). For the purpose of this example, $R_4$ is an aryl group further substituted with $R_6$. $R_3$ may be part of a fused or unfused bicyclic ring system.

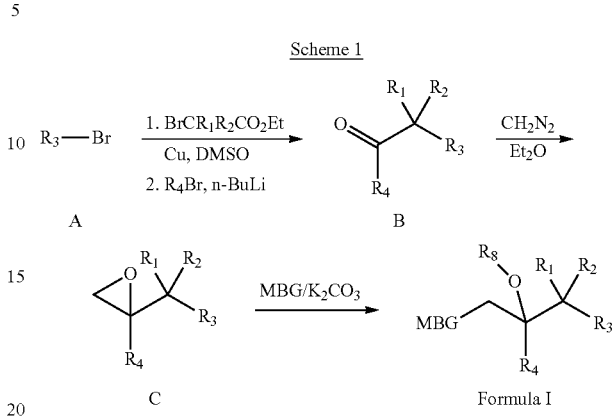

Scheme 1

Example 1

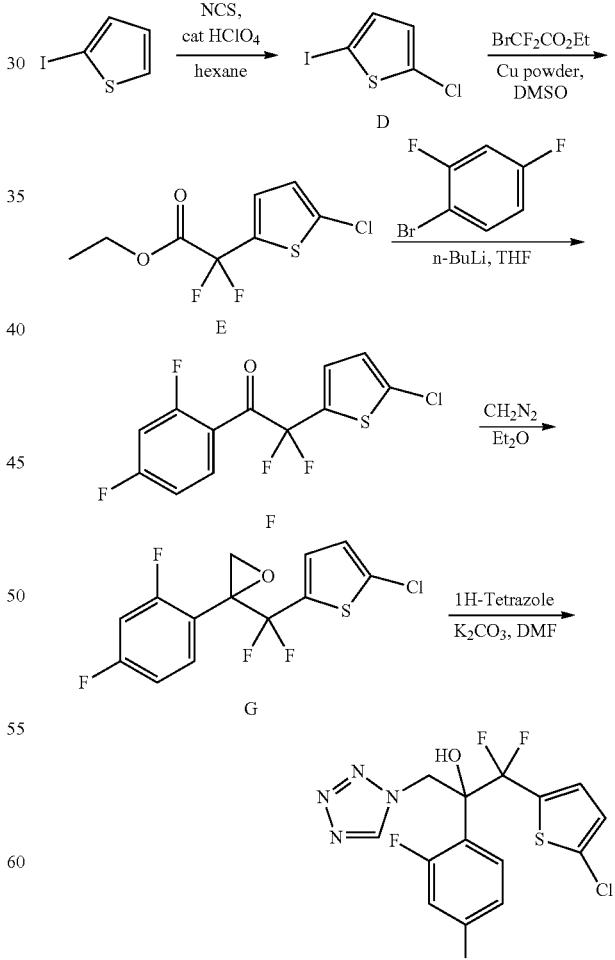

1-(5-Chlorothiophen-2-yl)-2-(2,4-difluorophenyl)-1,1-difluoro-3-(1H-tetrazol-1-yl)propan-2-ol (1)

To a stirred solution of 2-iodothiophene (2.5 grams (g), 11.9 millimoles (mmol)) in n-hexane (25 milliliters (mL)) was added N-chlorosuccinimide (NCS; 1.58 g, 11.9 mmol) followed by a catalytic (cat) amount of perchloric acid (HClO₄) at room temperature (RT), and stirring was continued for 24 hours (h) at RT. The reaction mixture was filtered, and the filtrate was washed with water (H₂O) and brine, dried over anhydrous sodium sulfate (Na₂SO₄) and concentrated in vacuo to afford D (1.7 g, 6.9 mmol, 58%) as a liquid. ¹H NMR (200 MHz, CDCl₃): δ 7.18 (d, J=4.2 Hz, 1 H), 6.69 (d, J=4.2 Hz, 1 H).

To a stirred solution of ethyl 2-bromo-2,2-difluoroacetate (1.6 mL, 13.9 mmol) in dimethyl sulfoxide (DMSO; 30 mL) was added copper powder (1.7 g, 27.9 mmol) at RT. After stirring for 1 h at RT, 2-chloro-5-iodothiophene D (1.7 g, 6.98 mmol) was added, and stirring was continued for another 12 h at RT. The progress of the reaction was monitored by thin layer chromatography (TLC). The reaction was quenched with a saturated (satd) ammonium chloride (NH₄Cl) solution and extracted with dichloromethane (CH₂Cl₂; 3×50 mL). The combined organic layers were washed with H₂O (2×50 mL) and brine, dried over anhydrous Na₂SO₄ and concentrated under reduced pressure to afford crude product which upon purification by column chromatography (eluting with EtOAc/hexane) afforded compound E (0.65 g, 2.7 mmol, 38%) as a liquid. ¹H NMR (200 MHz, CDCl₃): δ 7.19-7.17 (m, 1H), 6.89 (d, J=3.8 Hz, 1H), 4.37 (q, J=7.4 Hz, 2H), 1.36 (t, J=7.0 Hz, 3H).

To a stirred solution of 1-bromo-2,4-difluorobenzene (0.3 mL, 2.7 mmol) in ether (Et₂O; 20 mL) was added n-butyllithium (n-BuLi, 1.6 M in hexane; 1.77 mL, 2.7 mmol) at −78° C. under an inert atmosphere. After being stirred for 15 minutes (min) at −78° C., a solution of compound E (0.65 g, 2.7 mmol) in Et₂O (10 mL) was added to the reaction mixture, and stirring was continued for 1 h at −78° C. and for 1 h at RT. The progress of the reaction was monitored by TLC. The reaction was quenched with a satd NH₄Cl solution and extracted with ethyl acetate (EtOAc; 3×30 mL). The combined organic layers were washed with H₂O and brine, dried over anhydrous Na₂SO₄ and concentrated under reduced pressure to afford crude product which upon purification by column chromatography (eluting with EtOAc/hexane) afforded compound F (0.5 g, 1.62 mmol, 60%) as a solid. ¹H NMR (200 MHz, CDCl₃): δ 7.90-7.79 (m, 1H), 7.15-7.12 (m, 1H), 7.04-6.86 (m, 3H).

To a stirred solution of F (0.5 g, 1.62 mmol) in Et₂O (40 mL) was added freshly prepared diazomethane [Nitrosyl methyl urea (NMU; 0.9 g) in 10% potassium hydroxide (KOH; 40 mL)] at 0° C. and the reaction mixture was then warmed to RT. After stirring for 2 h at RT, the volatiles were evaporated under reduced pressure to afford crude product. The crude product was purified by column chromatography (eluting with EtOAc/hexane) to afford epoxide G (0.3 g, 0.93 mmol, 57%) as a solid. ¹H NMR (200 MHz, CDCl₃): δ 7.34-7.27 (m, 1H), 7.09-6.75 (m, 4H), 3.37 (d, J=4.8 Hz, 1H), 2.98 (m, 1H).

To a stirred solution of 1H-tetrazole (0.039 g, 0.55 mmol) in N,N-dimethylformamide (DMF; 5 mL) was added potassium carbonate (K₂CO₃; 0.064 g, 0.46 mmol) at RT under a nitrogen (N₂) atmosphere. After stirring for 10 min at RT, epoxide G (0.15 g, 0.46 mmol) was added to the reaction mixture, and the mixture was heated at 65° C. for 8 h. The reaction mixture was cooled to RT, diluted with H₂O (40 mL) and then extracted with EtOAc (2×50 mL). The combined organic phases were washed with H₂O (2×25 mL) and brine (25 mL), dried over anhydrous Na₂SO₄ and concentrated under reduced pressure. The crude material was purified by column chromatography (eluting with EtOAc/hexane) to afford 1 (30 mg, 0.13 mmol, 16%) as a solid. ¹H NMR (500 MHz, CDCl₃): δ 8.61 (s, 1H), 7.37-7.32 (m, 1H), 6.85 (d, J=3.5 Hz, 1H), 6.80-6.74 (m, 3H), 5.60 (d, J=14.5 Hz, 1H), 5.02 (d, J=14.5 Hz, 1H). HPLC: 94.1%. MS (ESI): m/z 393 [M⁺+1].

Compounds 12-16 in Table 1 were prepared using the same conditions as compound 1 from commercially available starting materials (given in Table 1).

Example 2

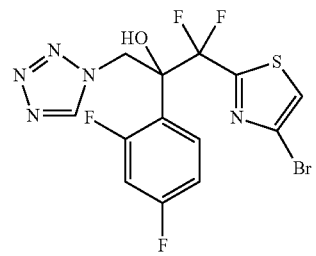 [SMILES: OC(Cn1cnnn1)(c1ccc(F)cc1F)C(F)(F)c1nc(Br)cs1]

1-(4-Bromothiazol-2-yl)-2-(2,4-difluorophenyl)-1,1-difluoro-3-(1H-tetrazol-1-yl)propan-2-ol (2)

Compound 2 was synthesized using the same conditions as compound 1. Yield: 47% (0.022 g). ¹H NMR (200 MHz, CDCl₃): δ 8.73 (s, 1H), 7.35 (m, 2H), 6.84-6.74 (m, 2H), 5.66 (d, J=15.0 Hz, 1H), 5.59 (br s, 1H), 5.19 (d, J=15.0 Hz, 1H). HPLC: 96.6%. MS (ESI): m/z 438, 440 [M⁺+1)+2].

Example 3

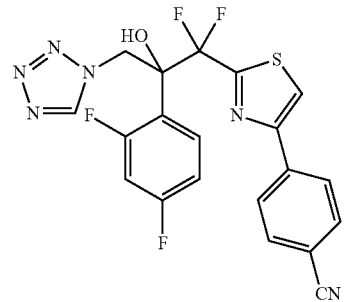 [SMILES: N#Cc1ccc(-c2csc(C(F)(F)C(O)(Cn3cnnn3)c3ccc(F)cc3F)n2)cc1]

4-(2-(2-(2,4-Difluorophenyl)-1,1-difluoro-2-hydroxy-3-(1H-tetrazol-1-yl)propyl)thiazol-4-yl)benzonitrile (3)

To a suspension of copper powder (1.04 g, 16.46 mmol) in DMSO (20 mL) was added ethyl 2-bromo-2,2-difluoroacetate (1.83 g, 9.0 mmol), and the mixture was stirred for 1 h at RT. Then 2,4-dibromothiazole (1.0 g, 4.11 mmol) was added, and stirring was continued for 16 h at RT. The progress of the reaction was monitored by TLC. The reaction was quenched with aqueous (aq) NH₄Cl (15 mL) and extracted with CH₂Cl₂ (3×50 mL). The combined organic layers were washed with H₂O and brine, dried over anhydrous Na₂SO₄ and concentrated under reduced pressure to afford a crude product. Silica gel column chromatography eluting with 6% EtOAc/hexane afforded the ester (0.35 g, 1.22 mmol, 37%) as a liquid. ¹H NMR (200 MHz, CDCl₃): δ 7.47 (s, 1H), 4.45-4.33 (m, 2H), 1.41-1.33 (m, 3H).

To a stirred solution of 1-bromo-2,4-difluorobenzene (0.20 mL, 1.83 mmol) in Et₂O (5 mL) was added n-BuLi (2.5 M solution in hexane; 0.7 mL, 1.83 mmol) at −78° C., and the mixture was stirred for 30 min. The ester from the previous step (0.35 g, 1.22 mmol) in Et₂O (10 mL) was added dropwise and the mixture was stirred for 1 h at −70° C. The temperature was raised gradually to ambient temperature, and stirring was continued for another 1 h. The reaction mixture was quenched with aq NH₄Cl and extracted with EtOAc (3×20 mL). The combined organic layers were washed with H₂O and brine, dried over anhydrous Na₂SO₄ and concentrated under reduced pressure. The crude compound was purified by silica gel column chromatography eluting with 4% EtOAc/Hexane to afford the ketone (0.13 g, 0.36 mmol, 30.09%) as a liquid. ¹H NMR (200 MHz, CDCl₃): δ 8.10-8.02 (m, 1H), 7.51 (s, 1H), 7.07-6.85 (m, 2H).

To a stirred solution of ketone (0.13 g, 0.36 mmol) in anhydrous Et₂O (30 mL) was added freshly prepared diazomethane [NMU (0.37 g) in 10% KOH (20 mL)] at 0° C., and the mixture was warmed to room temperature. After stirring for 1 h at RT, the solvent was evaporated under reduced pressure to afford a crude product. The crude product was purified by silica gel column chromatography eluting with 4% EtOAc/hexane to afford the epoxide (0.13 g, 0.36 mmol, 74%) as a liquid. ¹H NMR (200 MHz, CDCl₃): δ 7.51-7.30 (m, 2H), 6.94-6.75 (m, 2H), 3.58 (d, J=5.0 Hz, 1H), 3.05-3.03 (m, 1H).

To a stirred solution of epoxide (0.1 g, 0.27 mmol) and 4-cyanophenylboronic acid (0.059 g, 0.40 mmol) in tetrahydrofuran (THF)/H₂O (20 mL, 2:1) was added K₂CO₃ (0.112 g, 0.81 mmol) at RT under inert atmosphere. After purging with argon for a period of 10 min, 1,1'-Bis(diphenylphosphino)ferrocene]dichloropalladium(II) (Pd(dppf)₂Cl₂; 0.049 g, 0.06 mmol) was added to the reaction mixture under argon atmosphere. The resulting mixture was stirred for 16 h at 55° C. The reaction mixture was quenched with H₂O and extracted with EtOAc (3×50 mL). The combined organic phases were washed with H₂O and brine, dried over anhydrous Na₂SO₄ and concentrated. The crude material was purified by silica gel column chromatography eluting with 6% EtOAc/hexane to afford the coupled product (0.065 g, 0.16 mmol, 62%) as a solid. ¹H NMR (200 MHz, CDCl₃): δ 7.99 (d, J=6.6 Hz, 2H), 7.81-7.67 (m, 3H), 7.67-7.41 (m, 1H), 6.92-6.74 (m, 2H), 3.66 (d, J=5.0 Hz, 1H), 3.09-3.07 (m, 1H).

To a stirred solution of the coupled product (0.065 g, 0.16 mmol) in DMF (2 mL) was added 1H-tetrazole (0.013 g, 0.19 mmol) followed by K₂CO₃ (0.011 g, 0.08 mmol) at RT under inert atmosphere. The reaction mixture was stirred for 16 h at 70° C. The reaction mixture was cooled to RT, diluted with H₂O (5 mL) and extracted with EtOAc (2×20 mL). The organic layer was washed with H₂O and brine and dried over anhydrous Na₂SO₄. After filtering, the solvent was evaporated under reduced pressure to give crude compound. The crude compound was purified by silica gel column chromatography eluting with 30% EtOAc/hexane to afford 3 (15 mg, 0.03 mmol, 19%) as a solid. ¹H NMR (500 MHz, CDCl₃): δ 8.71 (s, 1H), 7.91 (d, J=8.0 Hz, 2H), 7.78 (s, 1H), 7.77 (d, J=8.5 Hz, 2H), 7.39-7.35 (m, 1H), 6.83-6.79 (m, 1H), 6.76- 6.73 (m, 1H), 5.87 (s, 1H), 5.67 (d, J=14.5 Hz, 1H), 5.24 (d, J=14.5 Hz, 1H). HPLC: 95.8%. MS (ESI): m/z 461 [M⁺+1].

Example 4

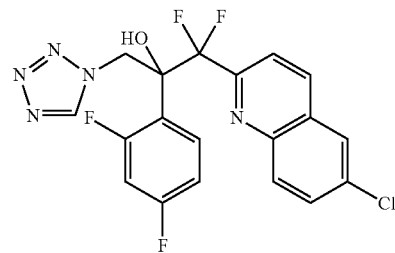 [SMILES: OC(Cn1cnnn1)(c1ccc(F)cc1F)C(F)(F)c1ccc2cc(Cl)ccc2n1]

1-(6-Chloroquinolin-2-yl)-2-(2,4-difluorophenyl)-1,1-difluoro-3-(1H-tetrazol-1-yl)propan-2-ol (4)

To a stirred suspension of copper powder (3.14 g, 47.4 mmol) in DMSO (50 mL) was added ethyl 2-bromo-2,2-difluoroacetate (4.99 g, 24.7 mmol) at RT under N₂ atmosphere. After stirring for 1 h at RT, 2-bromo-6-chloroquinoline (3.0 g, 12.3 mmol) was then added and stirring was continued for an additional 16 h at RT. The reaction mixture was quenched with satd NH₄Cl and extracted with CH₂Cl₂ (3×100 mL). The combined organic layers were washed with H₂O and brine, dried over anhydrous Na₂SO₄ and concentrated under reduced pressure. The crude material was purified by silica gel column chromatography eluting with 3% EtOAc/hexane to afford the 6-chloro-2-quinolinyl ethyl ester (2.6 g, 9.12 mmol, 73%) as a solid. ¹H NMR (500 MHz, CDCl₃): δ 8.26 (d, J=8.5 Hz, 1H), 8.08 (d, J=9.0 Hz, 1H), 7.87 (s, 1H), 7.82 (d, J=8.5 Hz, 1H), 7.71 (dd, J=9.0, 2.0 Hz, 1H), 4.44-4.39 (m, 2H), 1.38-1.34 (m, 3H). MS (ESI): m/z 286 [M⁺+1].

To a stirred solution of 1-bromo-2,4-difluorobenzene (0.15 mL, 1.40 mmol) in Et₂O (20 mL) was added n-BuLi (1.6 M in hexane; 0.87 mL, 1.40 mmol) at −70° C. under N₂ atmosphere. After being stirred for 15 min at −70° C., the ester (0.4 g, 1.40 mmol) in Et₂O (5 mL) was added to reaction mixture at −70° C. The reaction mixture was stirred for 1 h at 0° C., warmed to RT and stirred for another 1 h. The progress of the reaction was monitored by TLC. The reaction was quenched with a satd NH₄Cl solution and extracted with EtOAc (3×10 mL). The combined organic layers were washed with H₂O and brine, dried over anhydrous Na₂SO₄ and concentrated under reduced pressure. The crude compound was purified by silica gel column chromatography eluting with 3% EtOAc/hexane to afford the corresponding ketone (0.35 g, 0.98 mmol, 70%) as a liquid. ¹H NMR (500 MHz, CDCl₃): δ 8.30-8.23 (m, 1H), 8.14-8.07 (m, 1H), 7.96-7.87 (m, 2H), 7.76-7.65 (m, 2H), 7.01-6.98 (m, 1H), 6.80-6.76 (m, 1H). MS (ESI): m/z 354, 356 [(M⁺+1)+2].

To a stirred solution of the ketone (0.35 g, 0.98 mmol) in Et₂O (15 mL) was added freshly prepared diazomethane [NMU (0.8 g) in 10% KOH (50 mL)] drop-wise at −5° C. and the mixture was warmed to RT. After stirring for 1 h at RT, the volatiles were evaporated under reduced pressure to afford the crude product. The crude product was purified by column chromatography (1-3% EtOAc/hexane as a gradient) to afford the corresponding epoxide (0.14 g, 0.68 mmol, 39%) as semi-solid. ¹H NMR (200 MHz, CDCl₃): δ 8.16-8.06 (m, 2H), 7.88-7.85 (m, 1H), 7.74-7.58 (m, 2H), 7.43-7.28 (m, 1H), 6.87-6.68 (m, 2H), 3.50 (d, J=5.2 Hz, 1H), 3.01 (br s, 1H). MS (ESI): m/z 368 [M⁺+1].

To a stirred solution of epoxide (0.14 g, 0.38 mmol) in DMF (10 mL) was added 1H-tetrazole (0.026 g, 0.38 mmol) followed by $K_2CO_3$ (0.079 g, 0.57 mmol) at RT under inert atmosphere. The reaction mixture was stirred for 6 h at 70° C. The reaction mixture was cooled to RT, diluted with $H_2O$ (5 mL) and extracted with EtOAc (2×20 mL). The organic layer was washed with $H_2O$ and brine and dried over anhydrous $Na_2SO_4$. After filtering, the solvent was evaporated under reduced pressure to give crude compound. The crude compound was purified by silica gel column chromatography eluting with 30% EtOAc/hexane to afford 4 (0.085 g, 0.19 mmol, 51%) as a white solid and 1-(6-chloroquinolin-2-yl)-2-(2,4-difluorophenyl)-1,1-difluoro-3-(2H-tetrazol-2-yl)propan-2-ol (16; 0.04 g, 0.09 mmol, 24%) as white solid. ¹H NMR (500 MHz, CDCl₃): δ 8.76 (s, 1H), 8.22 (d, J=8.5 Hz, 1H), 8.03 (d, J=9.5 Hz, 1H), 7.87 (s, 1H), 7.79 (dd, J=9.0, 2.5 Hz, 1H), 7.67 (d, J=9.0 Hz, 2H), 7.32-7.27 (m, 1H), 6.78-6.73 (m, 1H), 6.60-6.57 (m, 1H), 5.64 (d, J=14.5 Hz, 1H), 5.19 (d, J=14.5 Hz, 1H). HPLC: 98.6%. MS (ESI): m/z 438 [M⁺+1]. Racemic 1-(6-Chloroquinolin-2-yl)-2-(2,4-difluorophenyl)-1,1-difluoro-3-(2H-tetrazol-2-yl)propan-2-ol (minor product, 16): ¹H NMR (500 MHz, CDCl₃): δ 8.26 (s, 1H), 8.20 (d, J=9.0 Hz, 1H), 7.99 (d, J=9.5 Hz, 1H), 7.85 (s, 1H), 7.75 (dd, J=8.5, 2.0 Hz, 1H), 7.68 (d, J=8.5 Hz, 1H), 7.41-7.36 (m, 1H), 6.98 (s, 1H), 6.81-6.77 (m, 1H), 6.65-6.61 (m, 1H), 5.85 (d, J=14.5 Hz, 1H), 5.49 (d, J=14.5 Hz, 1H). HPLC: 97.8%. MS (ESI): m/z 438 [M⁺+1].

Separation of 4 Enantiomers (+ and −)

The enantiomers of 4 were separated by high performance liquid chromatography (HPLC) using a CHIRALPAK IC® column (250×4.6 mm, 5μ) with mobile phase (A) n-hexane—(B) isopropyl alcohol (IPA) (Isocratic A:B=70:30) and flow rate 1.00 mL/min Diluent: IPA:Hexane (20:80)

Chiral preparative HPLC separation afforded 4-(−) ([α]$_D$−7.5° (c=0.1% in methyl alcohol (CH₃OH) and 4-(+) ([α]$_D$ 3.58° (c=0.1% in CH₃OH).

Compounds 17-33 in Table 1 were prepared using the same conditions as compound 4 from commercially available starting materials or prepared intermediates (given in Table 1).

Example 5

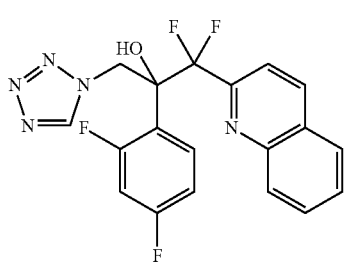 [SMILES: OC(Cn1cnnn1)(c1ccc(F)cc1F)C(F)(F)c1ccc2ccccc2n1]

2-(2,4-Difluorophenyl)-1,1-difluoro-1-(quinolin-2-yl)-3-(1H-tetrazol-1-yl)propan-2-ol (5)

Compound 5 was prepared using the conditions employed for 4 from 2-bromoquinoline: 0.020 g isolated as a cream solid. ¹H NMR (500 MHz, CDCl₃): δ 8.78 (s, 1H), 8.31 (d, J=8.5 Hz, 1H), 8.14 (s, 1H), 8.11 (d, J=8.5 Hz, 1H), 7.90-7.85 (m, 2H), 7.71-7.65 (m, 2H), 7.35-7.30 (m, 1H), 6.77-6.73 (m, 1H), 6.59-6.55 (m, 1H), 5.68 (d, J=14.0 Hz, 1H), 5.17 (d, J=14.0 Hz, 1H). HPLC: 97.65%. MS (ESI): m/z 404 [M⁺+1].

Example 6

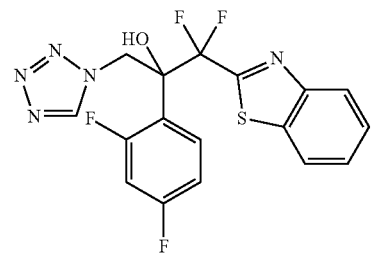 [SMILES: OC(Cn1cnnn1)(c1ccc(F)cc1F)C(F)(F)c1nc2ccccc2s1]

1-(Benzo[d]thiazol-2-yl)-2-(2,4-difluorophenyl)-1,1-difluoro-3-(1H-tetrazol-1-yl)propan-2-ol (6)

Compound 6 was prepared using the conditions employed for 4 from 2-bromobenzo[d]thiazole: 0.027 g as a tan solid. ¹H NMR (500 MHz, CDCl₃): δ 8.75 (s, 1H) 8.12 (d, J=8.5 Hz, 1H), 7.95 (d, J=8.0 Hz, 1H), 7.63-7.60 (m, 1H), 7.56-7.53 (m, 1H), 6.81-6.76 (m, 1H), 6.70-6.66 (m, 1H), 6.42 (s, 1H), 5.73 (d, J=14.5 Hz, 1H), 5.17 (d, J=14.5 Hz, 1H). HPLC: 96.1%. MS (ESI): m/z 410 [M⁺+1].

Example 7

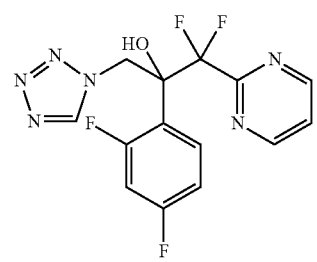 [SMILES: OC(Cn1cnnn1)(c1ccc(F)cc1F)C(F)(F)c1ncccn1]

2-(2,4-Difluorophenyl)-1,1-difluoro-1-(pyrimidin-2-yl)-3-(1H-tetrazol-1-yl)propan-2-ol (7)

Compound 7 was prepared using the conditions employed for 1 from 2-iodopyrimidine: 0.007 g as a tan solid. ¹H NMR (500 MHz, CDCl₃): δ 8.79 (d, J=4.5 Hz, 2H), 8.73 (s, 1H), 7.47-7.45 (m, 1H), 7.36-7.31 (m, 1H), 6.79-6.75 (m, 1H), 6.70-6.67 (m, 1H), 6.39 (s, 1H), 5.60 (d, J=14.5 Hz, 1H), 5.20 (d, J=14.5 Hz, 1H). HPLC: 98.8%. MS (ESI): m/z 355 [M⁺+1].

Example 8

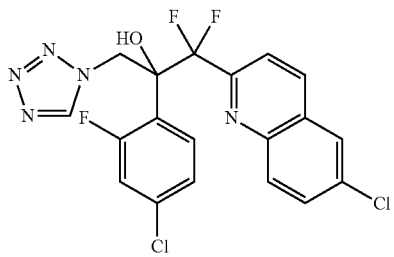 [SMILES: OC(Cn1cnnn1)(c1ccc(Cl)cc1F)C(F)(F)c1ccc2cc(Cl)ccc2n1]

2-(4-Chloro-2-fluorophenyl)-1-(6-chloroquinolin-2-yl)-1,1-difluoro-3-(1H-tetrazol-1-yl)propan-2-ol (8)

Compound 8 was prepared using the conditions employed for 4 from 2-bromo-6-chloroquinoline and 1-bromo-2-fluoro-4-chlorobenzene: 0.021 g isolated as a white solid. $^1$H NMR (500 MHz, CDCl$_3$): δ 8.76 (s, 1H), 8.23 (d, J=9.0 Hz, 1H), 8.04 (d, J=9.0 Hz, 1H), 7.88 (d, J=2.0 Hz, 1H), 7.79 (dd, J=9.0, 2.0 Hz, 1H), 7.72 (s, OH), 7.67 (d, J=9.0 Hz, 1H), 7.28-7.24 (m, 1H), 7.04 (dd, J=12.0, 2.0 Hz, 1H), 6.85 (dd, J=8.5, 2.0 Hz, 1H), 5.64 (d, J=14.5 Hz, 1H), 5.20 (d, J=14.5 Hz, 1H). HPLC: 99.4%. MS (ESI): m/z 456 [M$^+$+1].

Chiral Preparative HPLC Separation of Enantiomers of 8

The enantiomers of 8 (150 mg, 0.33 mmol) were separated by preparative HPLC using a CHIRALPAK IC® column (250×20 mm, 5μ; mobile phase (A) n-hexane—(B) ethyl alcohol (A:B=90:10) and flow rate 15 mL/min) to obtain 8-(−) (30 mg, 0.066 mmol, 20%) as an off-white solid.

Analytical Data:

Chiral HPLC: 99.88% ee, R$_t$=20.29 min (CHIRALPAK IC® column, 250×4.6 mm, 5μ; mobile phase (A) n-hexane—(B) ethyl alcohol (A:B=90:10); flow rate 1.00 mL/min). Optical rotation [α]$_D^{25}$: −29.44° (c=0.1% in CH$_3$OH). $^1$H NMR (500 MHz, CDCl$_3$): δ 8.76 (s, 1H), 8.23 (d, J=9.0 Hz, 1H), 8.04 (d, J=9.0 Hz, 1H), 7.88 (d, J=2.0 Hz, 1H), 7.79 (dd, J=9.0, 2.0 Hz, 1H), 7.72 (s, OH), 7.67 (d, J=9.0 Hz, 1H), 7.28-7.24 (m, 1H), 7.04 (dd, J=12.0, 2.0 Hz, 1H), 6.85 (dd, J=8.5, 2.0 Hz, 1H), 5.64 (d, J=14.5 Hz, 1H), 5.20 (d, J=14.5 Hz, 1H). MS (ESI): m/z 454 [M$^+$]. HPLC: 99.29%.

Example 9

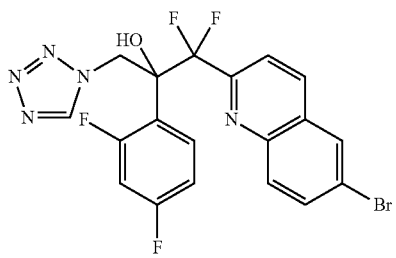 [SMILES: OC(Cn1cnnn1)(c1ccc(F)cc1F)C(F)(F)c1ccc2cc(Br)ccc2n1]

1-(6-Bromoquinolin-2-yl)-2-(2,4-difluorophenyl)-1,1-difluoro-3-(1H-tetrazol-1-yl)propan-2-ol (9)

Compound 9 was prepared using the conditions employed for 4 from 2,6-dibromoquinoline: 0.025 g isolated as a yellow solid. $^1$H NMR (500 MHz, CDCl$_3$): δ (8.76 (s, 1H), 8.21 (d, J=8.5 Hz, 1H), 8.06 (s, 1H), 7.97-7.91 (m, 2H), 7.67-7.65 (m, 2H), 7.32-7.27 (m, 1H), 6.77-6.73 (m, 1H), 6.60-6.57 (m, 1H), 5.63 (d, J=14.5 Hz, 1 H), 5.20 (d, J=14.5 Hz, 1H). HPLC: 93.3%. MS (ESI): m/z 482, 484 [M$^+$, M$^+$+2].

Chiral Preparative HPLC Separation of Enantiomers for 9-(+)

The enantiomers of 9 (150 mg, 0.31 mmol) were separated by preparative HPLC using a CHIRALPAK IC® column (250×20 mm, 5μ) with mobile phase (A) n-hexane—(B) [CH$_2$Cl$_2$-ethyl alcohol (80:20)] (A:B=75:25) and flow rate 12 mL/min to obtain 9-(+) (30 mg, 0.062 mmol, 20%) as an off-white solid.

Analytical Data:

Chiral HPLC: 99.90% ee, R$_t$=21.25 min (CHIRALPAK IC® column, 250×4.6 mm, 5μ; mobile phase (A) n-hexane—(B) ethyl alcohol (A:B=90:10); flow rate 1.00 mL/min). Optical rotation [α]$_D^{25}$: +5.80° (c=0.1% in CH$_3$OH). $^1$H NMR (500 MHz, CDCl$_3$): δ 8.76 (s, 1H), 8.21 (d, J=8.5 Hz, 1H), 8.06 (d, J=1.5 Hz, 1H), 7.97 (d, J=8.5 Hz, 1H), 7.92 (dd, J=9.0, 1.5 Hz, 1H), 7.67 (d, J=9.0 Hz, 1H), 7.66 (br s, OH), 7.32-7.27 (m, 1H), 6.77-6.73 (m, 1H), 6.60-6.57 (m, 1H), 5.64 (d, J=14.5 Hz, 1H), 5.20 (d, J=14.5 Hz, 1H). HPLC: 99.55%. MS (ESI): m/z 482 [M$^+$].

Example 10

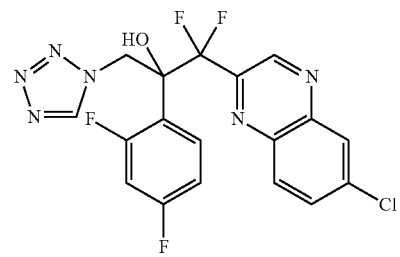 [SMILES: OC(Cn1cnnn1)(c1ccc(F)cc1F)C(F)(F)c1cnc2cc(Cl)ccc2n1]

1-(6-Chloroquinoxalin-2-yl)-2-(2,4-difluorophenyl)-1,1-difluoro-3-(1H-tetrazol-1-yl)propan-2-ol (10)

Compound 10 was synthesized using conditions employed for 4 from 2-bromo-6-chloroquinoxaline. 2-Bromo-6-chloroquinoxaline was prepared in the following manner. A mixture of 6-chloroquinoxalin-2(1H)-one (1.0 g, 5.5 mmol) and phosphorus tribromide (PBr$_3$; 3.5 mL, 36.1 mmol) was heated at 120° C. for 4 h. The reaction mass was cooled to RT, diluted with cold H$_2$O and extracted with CH$_2$Cl$_2$. The combined organic extracts were dried over Na$_2$SO$_4$, filtered and concentrated under vacuum to get crude product. The crude compound was purified by silica gel column chromatography (eluting with EtOAc/hexane) to afford 2-bromo-6-chloroquinoxaline (550 mg, 2.26 mmol, 42%) as a solid. $^1$H NMR (200 MHz, CDCl$_3$): δ 8.86 (s, 1H), 8.11 (s, 1H), 7.99 (d, J=8.8 Hz, 1H), 7.75 (dd, J=9.0, 2.4 Hz, H). MS (ESI): m/z 243 [M$^+$].

Compound 10 (25 mg, 0.056 mmol, 26%) was isolated as an off-white solid. $^1$H NMR (500 MHz, CDCl$_3$): δ 9.01 (s, 1H), 8.72 (s, 1H), 8.18 (s, 1H), 8.02 (d, J=9.0 Hz, 1H), 7.85 (dd, J=9.0, 2.0 Hz, 1H), 7.27 (s, 1H), 6.80-6.75 (m, 1H), 6.69-6.64 (m, 1H), 5.78 (s, 1H, OH), 5.70 (d, J=14.5 Hz, 1H), 5.20 (d, J=14.5 Hz, 1H). HPLC: 97.9%. MS (ESI): m/z 439 [M$^+$+1].

Chiral Preparative HPLC Separation of Enantiomers for 10-(−)

The enantiomers of 10 (70 mg, 0.16 mmol) were separated by preparative HPLC using a CHIRALPAK IA® column (250×20 mm, 5μ) with mobile phase (A) n-hexane—(B) ethyl alcohol (A:B=70:30) and flow rate 15 mL/min to obtain 10-(−) (20 mg, 0.046 mmol, 28%) as an off-white solid.

Analytical Data:

Chiral HPLC: 99.68% ee, $R_f$=10.31 min (CHIRALPAK IA® column, 250×4.6 mm, 5μ; mobile phase (A) n-hexane—(B) ethyl alcohol (A:B=85:15); flow rate: 1.00 mL/min). Optical rotation $[\alpha]_D^{25}$: −18.52° (c=0.1% in $CH_3OH$). $^1H$ NMR (500 MHz, $CDCl_3$): δ 9.01 (s, 1H), 8.72 (s, 1H), 8.18 (d, J=2.0 Hz, 1H), 8.01 (d, J=9.0 Hz, 1H), 7.84 (dd, J=9.0, 2.0 Hz, 1H), 7.29-7.26 (m, 1H), 6.81-6.77 (m, 1H), 6.68-6.65 (m, 1H), 5.77 (s, OH), 5.71 (d, J=14.5 Hz, 1H), 5.21 (d, J=14.5 Hz, 1H). HPLC: 99.06%. MS (ESI): m/z 439 $[M+H]^+$.

Compound 34 in Table 1 was prepared using the same conditions as compound 10 from commercially available starting materials (given in Table 1).

Example 11

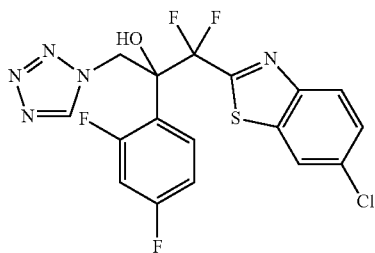 [SMILES: OC(Cn1cnnn1)(c1ccc(F)cc1F)C(F)(F)c1nc2ccc(Cl)cc2s1]

1-(6-Chlorobenzo[d]thiazol-2-yl)-2-(2,4-difluorophenyl)-1,1-difluoro-3-(1H-tetrazol-1-yl)propan-2-ol (11)

Compound 11 was prepared using the conditions employed for 4 from 2-bromo-6-chlorobenzo[d]thiazole: 0.017 g isolated as a cream colored solid. $^1H$ NMR (500 MHz, $CDCl_3$): δ 8.73 (s, 1H), 8.03 (d, J=9.0 Hz, 1H), 7.92 (s, 1H), 7.58 (dd, J=9.0, 2.5 Hz, 1H), 7.39-7.34 (m, 1H), 6.81-6.77 (m, 1H), 6.71-6.68 (m, 1H), 6.06 (s, 1H), 5.70 (d, J=14.5 Hz, 1H), 5.20 (d, J=14.5 Hz, 1H). HPLC: 96.6%. MS (ESI): m/z 444 $[M^++1]$.

Example 12

Preparation of Intermediates

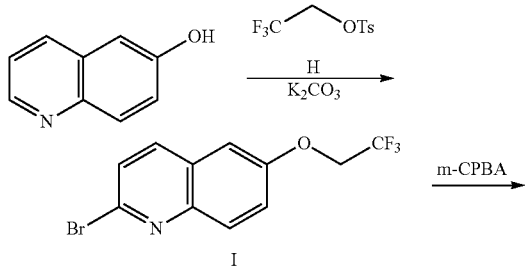

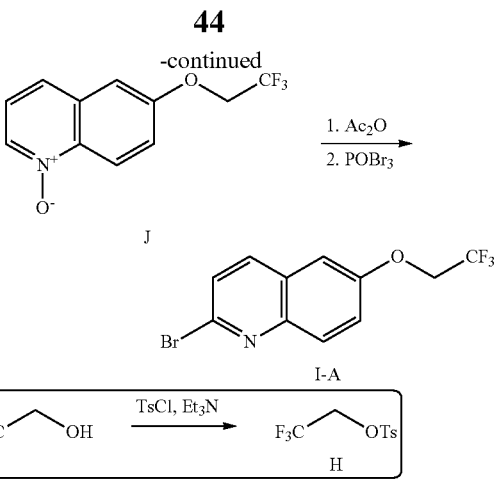

2-Bromo-6-(2,2,2-trifluoroethoxy)quinoline (I-A)

To a stirred solution of 2,2,2-trifluoroethanol (10.0 g, 100 mmol) in $CH_2Cl_2$ (100 mL) were added triethylamine ($Et_3N$, 27.8 mL, 200 mmol), p-toluenesulfonyl chloride (19.1 g, 100 mmol) and a catalytic amount of 4-dimethylaminopyridine (DMAP; 10 mg) at 0° C. under inert atmosphere. The reaction mixture was allowed to warm to RT and stirring was maintained for another 5 h. The reaction mixture was diluted with $H_2O$ (100 mL) and extracted with $CH_2Cl_2$ (3×200 mL). The combined organic extracts were washed with $H_2O$ (50 mL) and brine (50 mL), dried over anhydrous $Na_2SO_4$ and concentrated under reduced pressure to afford compound II (25.0 g, 98.42 mmol; crude) as a semi solid. $^1H$ NMR (200 MHz, $CDCl_3$): δ 7.81 (d, J=8.0 Hz, 2H), 7.38 (d, J=8.0 Hz, 2H), 4.35 (q, J=8.0 Hz, 2H), 2.47 (s, 3H). MS (ESI): m/z 256 $[M+2]^+$.

To a stirred solution of 6-hydroxyquinoline (2.0 g, 13.79 mmol) in DMF (15 mL) were added $K_2CO_3$ (5.71 g, 41.38 mmol) and compound II (7.01 g, 27.59 mmol) at RT. The reaction temperature was gradually increased to 80° C., at which point the reaction mixture was stirred for another 16 h. After completion of reaction (monitored by TLC), the reaction mixture was cooled to RT, diluted with $H_2O$ (25 mL) and extracted with EtOAc (3×40 mL). The combined organic extracts were washed with brine (30 mL), dried over anhydrous $Na_2SO_4$ and concentrated under reduced pressure. The crude material was purified by silica gel column chromatography (30-35% EtOAc gradient in hexanes) to afford compound I (2.7 g, 11.88 mmol, 86%). $^1H$ NMR (200 MHz, $CDCl_3$): δ 8.83 (dd, J=4.4, 1.8 Hz, 1H), 8.06-8.03 (m, 2H), 7.22-7.18 (m, 2H), 7.05 (d, J=3.0, 1H), 4.50 (q, J=8.0 Hz, 2H). MS (ESI): m/z 228 $[M+H]^+$.

To a stirred solution of I (0.6 g, 2.64 mmol) in EtOAc (25 mL) was added m-chloroperoxybenzoic acid (m-CPBA; 1.14 g, 6.63 mmol) at RT and under inert atmosphere. After completion of reaction (6 h, monitored by TLC), the reaction mixture was quenched with satd sodium bicarbonate ($NaHCO_3$) solution (30 mL) and extracted with EtOAc (3×40 mL). The combined organic extracts were washed with $H_2O$ (30 mL) and brine (30 mL), dried over anhydrous $Na_2SO_4$ and concentrated under reduced pressure. The crude material was purified by silica gel column chromatography (75-85% EtOAc gradient in hexanes) to afford compound J (0.5 g, 2.06 mmol, 77.8%). $^1H$ NMR (200 MHz, $CDCl_3$): δ 8.73 (d, J=9.4 Hz, 1H), 8.44 (d, J=6.2 Hz, 1H), 7.64 (d, J=8.2 Hz, 1H), 7.46 (dd, J=9.4, 2.8 Hz, 1H), 7.31 (dd, J=8.2, 6.2 Hz, 1H), 7.17 (d, J=2.8 Hz, 1H), 4.50 (q, J=8.0 Hz, 2H). MS (ESI): m/z 244 $[M+H]^+$.

A stirred solution of quinoline N-oxide J (1.0 g, 4.11 mmol) in acetic anhydride (Ac$_2$O; 7 mL) was heated at 130-140° C. for 5 h under inert atmosphere. The resultant mixture was cooled to RT, diluted with H$_2$O (25 mL) and extracted with EtOAc (3×30 mL). The combined organic extracts were washed with brine (40 mL), dried over anhydrous Na$_2$SO$_4$ and concentrated under reduced pressure. Phosphorus(III) oxybromide (POBr$_3$; 2.95 g, 10.28 mmol) was mixed with the obtained crude material and heated up to 130-140° C., and stirred for 4 h under inert atmospheric conditions. After completion of reaction (monitored by TLC), the reaction mixture was cooled to RT, quenched with ice-cold H$_2$O (30 mL) and extracted with EtOAc (3×30 mL). The combined organic extracts were washed with H$_2$O (30 mL) and brine (30 mL), dried over anhydrous Na$_2$SO$_4$ and concentrated under reduced pressure. The crude material was purified by silica gel column chromatography (10-15% EtOAc gradient in hexanes) to afford 2-bromo-6-(2,2,2-trifluoroethoxy)quinoline (I-A; 0.55 g, 1.79 mmol, 43.7%). $^1$H NMR (200 MHz, CDCl$_3$): δ 8.01 (d, J=9.2 Hz, 1H), 7.90 (d, J=8.6 Hz, 1H), 7.51 (d, J=8.6 Hz, 1H), 7.42 (dd, J=9.2, 2.8 Hz, 1H), 7.10 (d, J=2.8 Hz, 1H), 4.46 (q, J=8.0 Hz, 2H). MS (ESI): m/z 307 [M+H]$^+$.

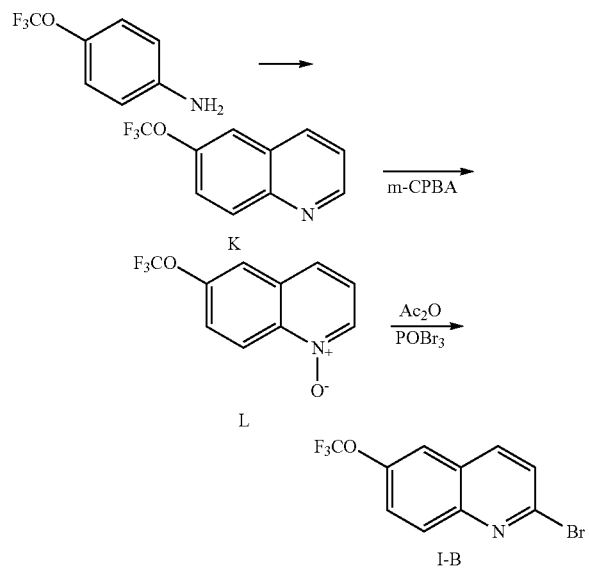

the quinoline K (0.95 g, 4.42 mmol, 79%) as a colorless liquid. $^1$H NMR (200 MHz, CDCl$_3$): δ 8.96-8.94 (m, 1H), 8.16 (d, J=8.2 Hz, 2H), 7.65-7.56 (m, 2H), 7.47 (dd, J=8.2, 4.2 Hz, 1H). MS (ESI): m/z 214 [M+H]$^+$.

To a stirred solution of K (0.95 g, 4.40 mmol) in EtOAc (10 mL) at 0° C. was added m-CPBA (1.5 g, 8.8 mmol) and the reaction mixture was stirred at RT for 6 h. After completion of the reaction (by TLC), the reaction mixture was quenched with satd NaHCO$_3$ solution and extracted with EtOAc (2×50 mL). The combined organic extracts were washed with H$_2$O (20 mL) and brine (20 mL), dried over anhydrous Na$_2$SO$_4$ and concentrated under reduced pressure to obtain the crude material. Purification by silica gel column chromatography (eluting with 10% CH$_3$OH/CH$_2$Cl$_2$ afforded L (0.72 g, 3.1 mmol, 70%) as a colorless liquid. $^1$H NMR (200 MHz, CDCl$_3$): δ 8.82 (d, J=9.4 Hz, 1H), 8.55 (d, J=6.2 Hz, 1H), 7.75-7.69 (m, 2H), 7.60 (dd, J=9.4, 1.6 Hz, 1H), 7.39 (dd, J=9.4, 6.2 Hz, 1H). MS (ESI): 230 [M+H]$^+$ A stirred solution of quinoline N-oxide L (1.0 g, 4.3 mmol) in Ac$_2$O (10 mL) was heated at 130-140° C. for 5 h under inert atmosphere. The resultant mixture was cooled to RT, diluted with H$_2$O (30 mL) and extracted with EtOAc (3×30 mL). The combined organic extracts were washed with brine (30 mL), dried over anhydrous Na$_2$SO$_4$ and concentrated under reduced pressure. POBr$_3$ (2.2 g, 7.7 mmol) was added to the obtained crude material, and the mixture was heated at 130-140° C. for 4 h under inert atmospheric conditions. After completion of reaction (monitored by TLC), the reaction mixture was cooled to RT, quenched with ice-cold H$_2$O (50 mL) and extracted with EtOAc (3×50 mL). The combined organic extracts were washed with H$_2$O (50 mL) and brine (50 mL), dried over anhydrous Na$_2$SO$_4$ and concentrated under reduced pressure. The crude material was purified by silica gel column chromatography (eluting with 10-15% EtOAc/hexanes) to afford compound I-B (0.55 g, 1.79 mmol, 43.7%) as a colorless liquid. $^1$H NMR (200 MHz, CDCl$_3$): δ 8.09 (d, J=9.0 Hz, 1H), 8.00 (d, J=9.0 Hz, 1H), 7.64-7.59 (m, 3H). MS (ESI): 292 [M+H]$^+$.

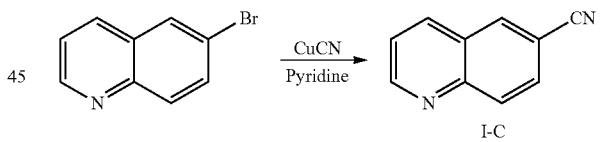

2-Bromo-6-(trifluoromethoxy)quinoline (I-B)

Quinoline-6-carbonitrile (I-C)

To a stirred solution of 4-(trifluoromethoxy)aniline (1.0 g, 5.6 mmol), sodium-3-nitrobenzene sulfonate (1.89 g, 8.4 mmol), boric acid (0.55 g, 8.9 mmol) and iron(II) sulfate heptahydrate (FeSO$_4$.7H$_2$O; 0.31 g, 1.1 mmol) in glycerol (14 mL) was added concentrated sulfuric acid (H$_2$SO$_4$; 3.4 mL) dropwise at 0° C. The reaction mixture was gradually heated to 150° C. and stirred for 5 h. After completion of the reaction (monitored by TLC), the reaction mixture was poured into ice-cold H$_2$O (100 mL), made basic with 50% aq sodium hydroxide (NaOH) solution (10 mL) and extracted with Et$_2$O (4×25 mL). The separated organic layer was washed with H$_2$O (50 mL) and brine (50 mL), dried over anhydrous Na$_2$SO$_4$ and concentrated under reduced pressure to obtain the crude material. Purification by silica gel column chromatography (eluting with 12% EtOAc/hexane) afforded To a stirred solution of 6-bromoquinoline (2.0 g, 9.61 mmol) in pyridine (30 mL) was added CuCN (3.0 g, 33.6 mmol) at RT under inert atmosphere. The reaction mixture was gradually heated to 200° C. and stirred for 8 h. After complete consumption of the starting material (by TLC), the reaction mixture was cooled to RT, diluted with ice-cold H$_2$O (100 mL) and extracted with EtOAc (3×100 mL). The combined organic extracts were washed with H$_2$O (50 mL) and brine (50 mL), dried over anhydrous Na$_2$SO$_4$ and concentrated under reduced pressure to obtain the crude material. Purification by silica gel column chromatography (eluting with 30% EtOAc/hexane) afforded compound I-C (1.25 g, 8.0 mmol, 83%) as white solid. $^1$H NMR (200 MHz, CDCl$_3$): δ 9.08-9.05 (m, 1H), 8.25-8.19 (m, 3H), 7.86 (dd, J=8.6, 1.8 Hz, 1H), 7.55 (dd, J=8.6, 1.8 Hz, 1H). MS (ESI): 155 [M+H]$^+$.

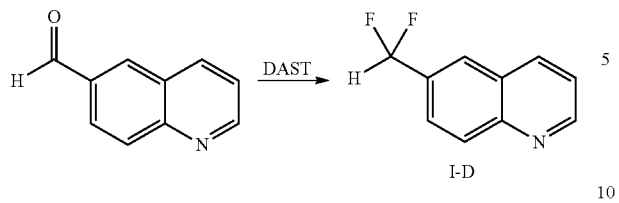
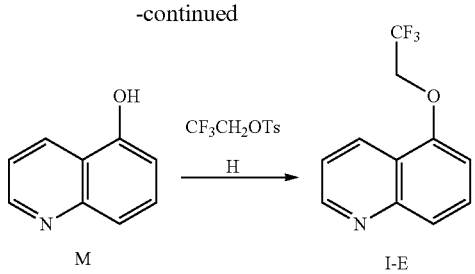

6-(Difluoromethyl)quinoline (I-D)

5-(2,2,2-Trifluoroethoxy)quinoline (I-E)

To a stirred solution of quinoline-6-carbaldehyde (200 mg, 1.27 mmol) in CH$_2$Cl$_2$ (10 mL) at 0° C. was added (diethylamino)sulfur trifluoride (DAST; 0.2 mL, 1.53 mmol) under inert atmosphere. The reaction mixture was allowed to warm to RT and stirred for 16 h. After complete consumption of the starting material (by TLC), the reaction mixture was diluted with CH$_2$Cl$_2$ (20 mL) and then quenched with satd NaHCO$_3$ solution (40 mL). The separated organic layer was washed with ice-cold H$_2$O (20 mL) and brine (20 mL), dried over anhydrous Na$_2$SO$_4$ and concentrated under reduced pressure to obtain I-D (100 mg, crude) as a yellow liquid. The product was characterized by $^1$H NMR spectroscopy and directly taken to the next step without purification. $^1$H NMR (200 MHz, CDCl$_3$): δ 9.00 (dd, J=4.2, 1.4 Hz, 1H), 8.25-8.18 (m, 2H), 7.98 (s, 1H), 7.84 (dd, J=8.8, 1.4 Hz, 1H), 7.48 (dd, J=8.8, 4.2 Hz, 1H), 6.84 (t, J$_{F,H}$=74.0 Hz, 1H). MS (ESI): 180 [M+H]$^+$.

To a stirred solution of amine 5-aminoquinoline (5.0 g, 34.67 mmol) in H$_2$O (100 mL) was added sodium bisulfate (NaHSO$_3$; 25.2 g, 242.1 mmol) at RT, and the mixture was stirred at reflux temperature for 36 h. The resulting solution was cooled to RT, NaOH (9.7 g, 242.5 mmol) was added, and the mixture was stirred at reflux temperature for 8 h. After completion of the reaction (monitored by TLC), the reaction mixture was cooled to RT and the pH was adjusted to 7.0 with 6 Normal (N) hydrochloride acid (HCl). The precipitate was filtered, washed with H$_2$O, and dried under high vacuum to obtain the desired alcohol M (3.2 g, 22.04 mmol, 64%) as pale-yellow solid. $^1$H NMR (500 MHz, CDCl$_3$): δ 8.92 (s, 1H), 8.58 (d, J=8.5 Hz, 1H), 7.71 (d, J=8.5 Hz, 1H), 7.53 (t, J=8.0 Hz, 1H), 7.41 (dd, J=8.5, 4.5 Hz, 1H), 6.88 (d, J=7.5 Hz, 1H), 6.10 (br s, 1H). MS (ESI): m/z 146 [M+H]$^+$.

A stirred solution of alcohol M (3.2 g, 22.04 mmol), 2,2,2-trifluoroethyl-4-methylbenzenesulfonate (5.6 g, 22.04 mmol) and K$_2$CO$_3$ (9.12 g, 66.08 mmol) in DMF (40 mL) was heated at 120° C. under an inert atmosphere. After completion of reaction (16 h, monitored by TLC), the reaction mixture was cooled to RT, diluted with H$_2$O (30 mL) and then extracted with EtOAc (3×40 mL). The combined organic extracts were washed with brine (40 mL), dried over anhydrous Na$_2$SO$_4$ and concentrated under reduced pressure to obtain the crude material. Purification by silica gel column chromatography (eluting with a 3-8% EtOAc gradient in hexanes) provided compound I-E (3.2 g, 14.08 mmol, 63.9%) as a white solid. $^1$H NMR (500 MHz, CDCl$_3$): δ 8.94 (d, J=6.0 Hz, 1H), 8.59 (d, J=8.5 Hz, 1H), 7.80 (d, J=9.0 Hz, 1H), 7.63-7.60 (m, 1H), 7.44 (dd, J=8.5, 4.5 Hz, 1H), 6.86 (d, J=8.0 Hz, 1H), 4.57-4.52 (m, 2H). MS (ESI): m/z 228.0 [M+H]$^+$.

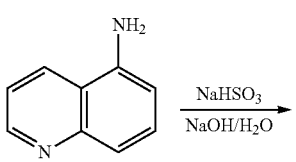

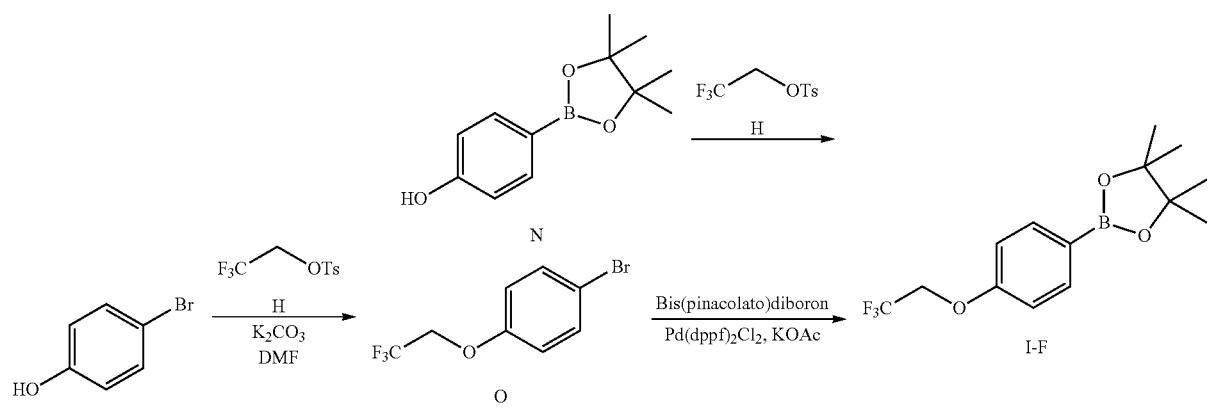

4,4,5,5-Tetramethyl-2-(4-(2,2,2-trifluoroethoxy)phenyl)-1,3,2-dioxaborolane (I-F)

To a stirred solution of boronate ester N (300 mg, 1.36 mmol) in DMF (10 mL) was added $K_2CO_3$ (940 mg, 6.81 mmol) followed by compound II (342 mg, 1.36 mmol) at RT under inert atmosphere. The reaction mixture was gradually heated to 120° C. and stirred for 24 h. Progress of the reaction was monitored by TLC. The reaction mixture was allowed to cool to RT and diluted with $H_2O$ (50 mL). The aqueous layer was extracted with EtOAc (2×50 mL). The combined organic layer was washed with $H_2O$ (50 mL) and brine (50 mL), dried over anhydrous $Na_2SO_4$ and concentrated in vacuo. The crude material was purified by silica gel column chromatography (eluting with 4% EtOAc/Hexane) to afford I-F (40 mg, 13.2 mmol, 9.7%) as a semi-solid. $^1$H NMR (200 MHz, $CDCl_3$): δ 7.78 (d, J=8.5 Hz, 2H), 6.93 (d, J=8.5 Hz, 2H), 4.37 (q, J=8.2 Hz, 2H), 1.36 (s, 12H).

I-F may also be synthesized in a two-step procedure. To a stirred solution of p-bromo phenol (1.5 g, 8.67 mmol) in DMF (15 mL) was added $K_2CO_3$ (6.0 g, 43.3 mmol) followed by tosyl compound II (2.2 g, 8.67 mmol) at RT under inert atmosphere. The reaction mixture was gradually heated to 110° C. for 4 h. After complete consumption of the starting material (by TLC), the reaction mixture was allowed to cool to RT, diluted with $H_2O$ (100 mL) and the aqueous layer was extracted with EtOAc (2×100 mL). The combined organic layer was washed with $H_2O$ (50 mL) and brine (50 mL), dried over anhydrous $Na_2SO_4$ and concentrated in vacuo. The crude material was purified by silica gel column chromatography (eluting with 3% EtOAc/hexane) to afford O (1.7 g, 6.66 mmol, 76%) as semi-solid. $^1$H NMR (200 MHz, $CDCl_3$): δ 7.45-7.38 (m, 2H), 6.87-6.79 (m, 2H), 4.32 (q, J=8.2 Hz, 2H).

To a stirred solution of O (0.5 g, 1.96 mmol) in 1,4-dioxane (50 mL) was added bis(pinacolato) diboron (0.54 g, 2.15 mmol) followed by potassium acetate (KOAc; 0.576 g, 5.88 mmol) at RT under inert atmosphere. After purging with $N_2$ for 10 min, $Pd(dppf)_2Cl_2$ (72 mg, 0.09 mmol) was added to the reaction mixture under $N_2$ atmosphere. The mixture was gradually heated to 110° C. and stirred for 2 h. After complete consumption of the starting material (by TLC), the volatiles were evaporated under reduced pressure; the obtained residue was dissolved in $H_2O$ (100 mL) and extracted with EtOAc (3×50 mL). The combined organic extracts were washed with $H_2O$ (50 mL) and brine (50 mL), dried over anhydrous $Na_2SO_4$ and concentrated in vacuo. The crude material was purified by silica gel column chromatography (eluting with 3-4% EtOAc/hexane) to afford I-F (0.28 g, 0.92 mmol, 47%) as a yellow syrup. $^1$H NMR (200 MHz, $CDCl_3$): δ 7.78 (d, J=8.5 Hz, 2H), 6.93 (d, J=8.5 Hz, 2H), 4.37 (q, J=8.2 Hz, 2H), 1.36 (s, 12H).

Example 13

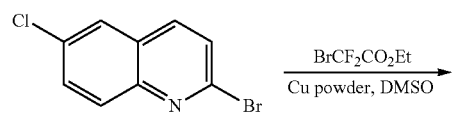

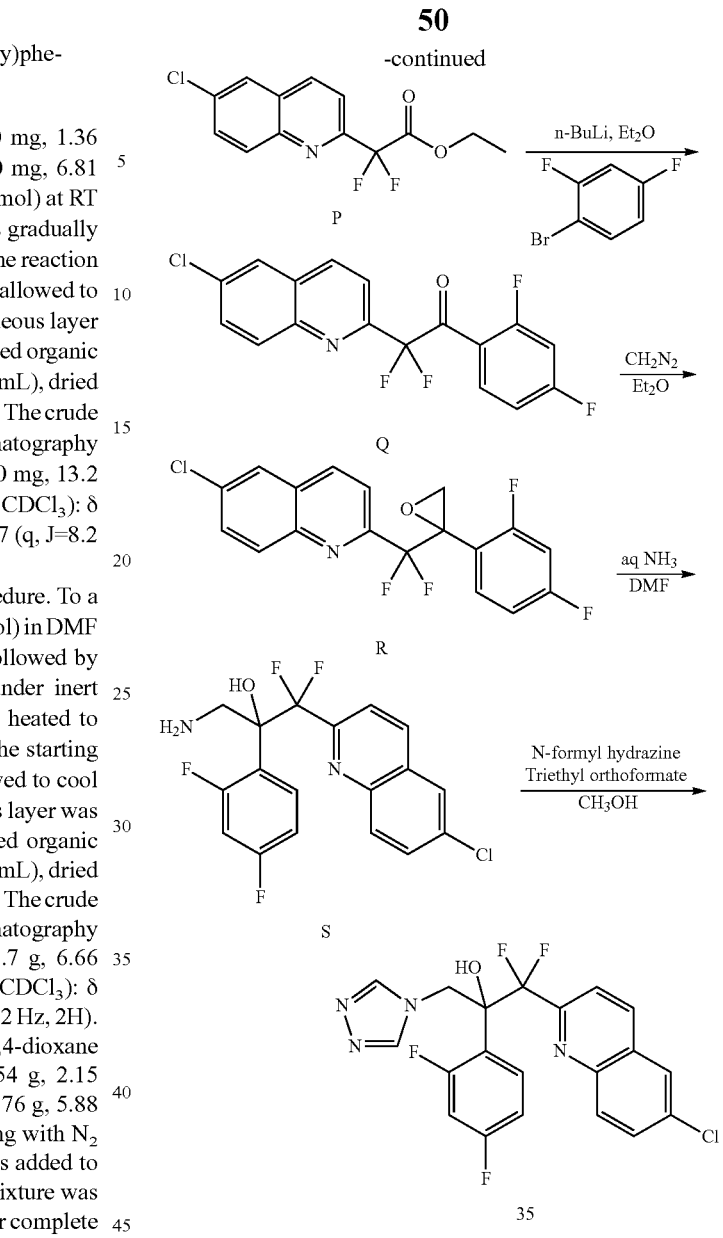

1-(6-Chloroquinolin-2-yl)-2-(2,4-difluorophenyl)-1,1-difluoro-3-(4H-1,2,4-triazol-4-yl)propan-2-ol (35)

To a stirred suspension of copper powder (2.6 g, 41.23 mmol) in DMSO (25 mL) was added ethyl 2-bromo-2,2-difluoroacetate (2.6 mL, 20.62 mmol) at RT under $N_2$ atmosphere. After being stirred for 1 h at RT, 2-bromo-6-chloroquinoline (2.5 g, 10.31 mmol) was added to the reaction mixture, and stirring was continued for another 16 h at RT. After completion of reaction (by TLC), the reaction mixture was quenched with satd $NH_4Cl$ solution and extracted with EtOAc (2×200 mL). The combined organic extracts were washed with $H_2O$ (50 mL) and brine (50 mL), dried over anhydrous $Na_2SO_4$ and concentrated under reduced pressure to obtain the crude material. Purification by silica gel column chromatography (eluting with 3% EtOAc/Hexane) afforded P (2.7 g, 9.47 mmol, 91%) as a white solid. $^1$H NMR (500 MHz, $CDCl_3$): δ 8.26 (d, J=8.5 Hz, 1H), 8.08 (d, J=9.0 Hz, 1H), 7.87 (s, 1H), 7.82 (d, J=8.5 Hz, 1H), 7.71 (dd, J=9.0, 2.0 Hz, 1H), 4.44-4.39 (m, 2H), 1.38-1.34 (m, 3H). MS (ESI): m/z 286 [M+1]$^+$.

To a stirred solution of 1-bromo-2,4-difluorobenzene (0.6 mL, 4.89 mmol) in Et$_2$O (20 mL) was added n-BuLi (2.5 M in hexane; 2 mL, 4.89 mmol) at −78° C. under N$_2$ atmosphere. After being stirred for 15 min, ester P (0.7 g, 2.44 mmol) in Et$_2$O (10 mL) was added at −78° C., and stirring was continued for another 2 h. The progress of the reaction was monitored by TLC. The reaction was quenched with satd NH$_4$Cl solution and extracted with CH$_2$Cl$_2$ (2×50 mL). The combined organic extracts were washed with H$_2$O (50 mL) and brine (50 mL), dried over anhydrous Na$_2$SO$_4$ and concentrated under reduced pressure to afford ketone Q (0.5 g, crude). The crude mixture was taken to the next step without purification. $^1$H NMR (500 MHz, CDCl$_3$): δ 8.30-8.23 (m, 1H), 8.14-8.07 (m, 1H), 7.96-7.87 (m, 2H), 7.76-7.65 (m, 2H), 7.01-6.98 (m, 1H), 6.80-6.76 (m, 1H). MS (ESI): m/z 354 [M+1]$^+$.

To a stirred solution of ketone Q (0.5 g, crude) in Et$_2$O (50 mL) was added freshly prepared diazomethane [prepared by dissolving NMU (2 g) in 1:1 mixture of 10% KOH solution (50 mL) and Et$_2$O (50 mL) at −5° C. followed by separation and drying of the organic layer using KOH pellets]. After being stirred for 1 h at RT, the volatiles were evaporated under reduced pressure to obtain the crude material. The crude product was purified by silica gel column chromatography (eluting with 1-3% EtOAc/Hexane) to afford compound R (0.35 g, 0.95 mmol) as white solid. $^1$H NMR (200 MHz, CDCl$_3$): δ 8.16-8.06 (m, 2H), 7.88-7.85 (m, 1H), 7.74-7.58 (m, 2H), 7.43-7.28 (m, 1H), 6.87-6.68 (m, 2H), 3.50 (d, J=5.2 Hz, 1H), 3.03-3.01 (m, 1H). MS (ESI): m/z 368 [M+1]$^+$.

To a stirred solution of epoxide R (300 mg, 0.817 mmol) in DMF (5 mL) was added aq ammonia (NH$_3$; 5 mL) at RT. The reaction mixture was gradually heated up to 80° C. and stirred for 3 h. The progress of the reaction was monitored by TLC. The volatiles were evaporated under reduced pressure, and the residue was diluted with EtOAc. The organic layer was then washed with H$_2$O (25 mL) and brine (25 mL), dried over anhydrous Na$_2$SO$_4$ and concentrated under reduced pressure to obtain the crude material. Purification by silica gel column chromatography (eluting with 3% CH$_3$OH/CH$_2$Cl$_2$) afforded amine S (100 mg, 0.26 mmol, 31%) as a syrup. $^1$H NMR (200 MHz, CDCl$_3$): δ 8.14-8.01 (m, 2H), 7.85 (s, 1H), 7.70 (dd, J=9.0, 2.2 Hz, 1H), 7.58-7.45 (m, 2H), 6.82-6.70 (m, 2H), 3.85 (dd, J=14.0, 4.8 Hz, 1H), 3.30 (d, J=14.0 Hz, 1H). MS (ESI): m/z 385 [M+1]$^+$.

To a stirred solution of N-formyl hydrazine (16 mg, 0.26 mmol) in CH$_3$OH (5 mL) was added triethyl orthoformate (0.1 mL, 0.26 mmol) at RT under inert atmosphere. The reaction mixture was then heated at 80° C. for 3 h; progress of the reaction was monitored by TLC. The reaction mixture was cooled to 40° C., S (50 mg, 0.13 mmol) was added and stirring was continued for another 3 h at 80° C. The volatiles were evaporated under reduced pressure, and the residue was diluted with EtOAc (25 mL). The organic layer was washed with H$_2$O (25 mL) and brine (25 mL), dried over Na$_2$SO$_4$ and concentrated under reduced pressure to obtain the crude product. The crude material was purified by silica gel column chromatography (eluting with 7% CH$_3$OH/CH$_2$Cl$_2$) to afford 35 (25 mg, 0.05 mmol, 44%) as colorless semi-solid. $^1$H NMR (500 MHz, CDCl$_3$): δ 8.21 (d, J=9.0 Hz, 1H), 8.16 (s, 2H), 8.08 (d, J=9.0 Hz, 1H), 7.87 (s, 1H), 7.82-7.78 (m, 2H), 7.64 (d, J=8.5 Hz, 1H), 7.32-7.29 (m, 1H), 6.77-6.72 (m, 1H), 6.58-6.55 (m, 1H), 5.14 (d, J=14.0 Hz, 1H), 4.75 (d, J=14.0 Hz, 1H). HPLC: 85.3%. MS (ESI): m/z 437 [M+1]$^+$.

Example 14

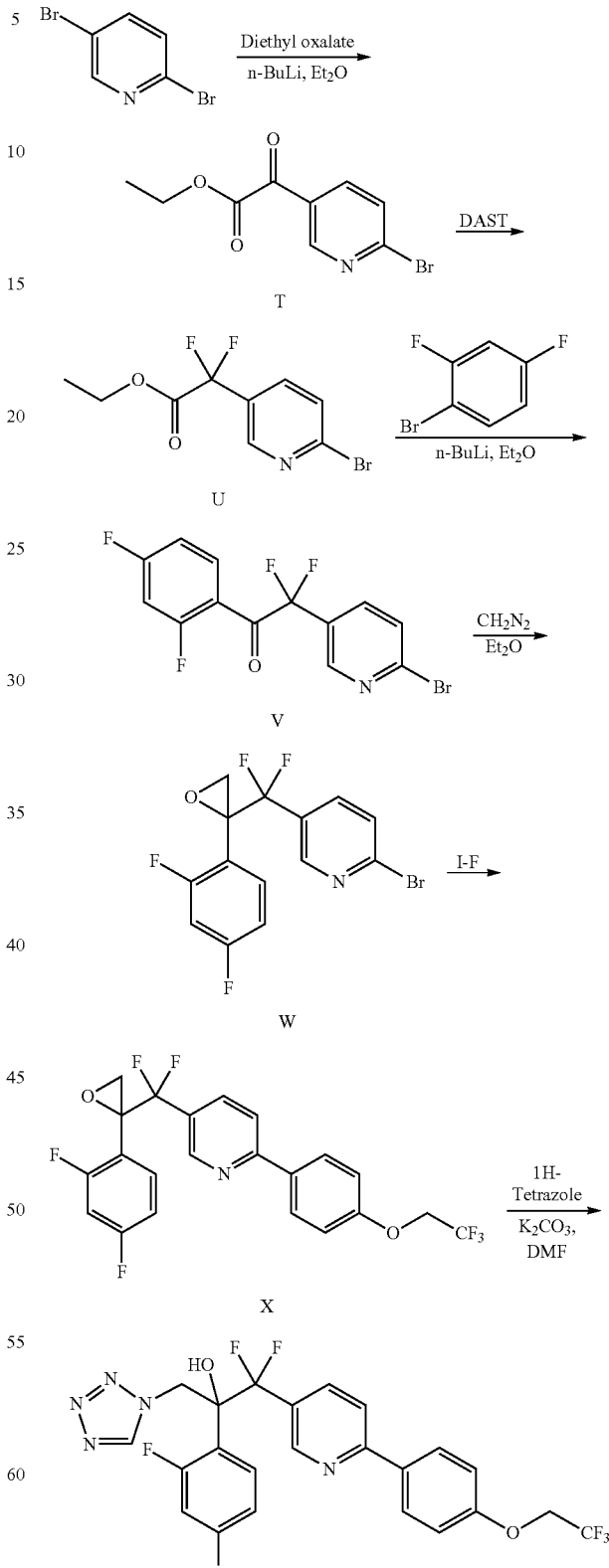

2-(2,4-Difluorophenyl)-1,1-difluoro-3-(1H-tetrazol-1-yl)-1-(6-(4-(2,2,2-trifluoroethoxy)phenyl)pyridin-3-yl)propan-2-ol (36)

To a stirred solution of 2,5-dibromopyridine (5.0 g, 21.09 mmol) in Et$_2$O (200 mL) was added n-BuLi (2.4 M in hexane; 10.5 mL, 25.3 mmol) at −78° C., and the reaction mixture was stirred for 1 h under inert atmosphere. Diethyl oxalate (4.0 mL, 25.3 mmol) was added to the reaction mixture at −78° C., and stirring was continued for another 10 min. The reaction mixture was allowed to warm to 0° C. and stirred for 2 h. After complete consumption of the starting material (by TLC), the reaction mixture was quenched with satd NH$_4$Cl solution and extracted with CH$_2$Cl$_2$ (2×100 mL). The combined organic extracts were washed with H$_2$O (40 mL) and brine (40 mL), dried over anhydrous Na$_2$SO$_4$ and concentrated under reduced pressure to obtain the crude. The crude material was purified by silica gel column chromatography (eluting with 8% EtOAc/hexane) to afford compound T (0.87 g, 3.37 mmol 16%) as a pale-yellow liquid. $^1$H NMR (500 MHz, CDCl$_3$): δ 9.09 (s, 1H), 8.34 (d, J=7.5 Hz, 1H), 7.49 (d, J=8.5 Hz, 1H), 4.46 (q, J=7.0 Hz, 2H), 1.44 (t, J=7.0 Hz, 3H). MS (ESI): m/z 259.2 [M+H]$^+$.

To a stirred solution of compound T (180 mg, 0.69 mmol) in CH$_2$Cl$_2$ (10 mL) was added DAST (140 mg, 0.87 mmol) at 0° C. under inert atmosphere. The resultant reaction mixture was allowed to warm to RT and stirred for 16 h. After complete consumption of the starting material (by TLC), the reaction mixture was diluted with CH$_2$Cl$_2$ (50 mL) and washed with ice-cold H$_2$O (50 mL) and brine (50 mL), dried over anhydrous Na$_2$SO$_4$ and concentrated under reduced pressure to obtain the crude material. Purification by silica gel column chromatography (eluting with 6% EtOAc/hexane) afforded ester U (105 mg, 0.37 mmol, 54%) as a yellow liquid. $^1$H NMR (500 MHz, CDCl$_3$): δ 8.62 (d, J=2.0 Hz, 1H), 7.77 (dd, J=8.0 Hz, 2.0 Hz, 1H), 7.60 (d, J=8.0 Hz, 1H), 4.33 (q, J=7.0 Hz, 2H), 1.29 (t, J=7.0 Hz, 3H). MS (ESI): m/z 282 [M+2]$^+$.

To a stirred solution of 1-bromo-2,4-difluorobenzene (0.1 mL, 0.38 mmol) in Et$_2$O (5 mL) was added n-BuLi (2.3 M in hexane; 0.16 mL, 0.38 mmol) at −78° C., and the reaction mixture was stirred for 30 min under inert atmosphere. A solution of ester U (90 mg, 0.32 mmol) in Et$_2$O (5 mL) was added to the reaction mixture at −78° C., and stirring was continued for another 2 h. After complete consumption of the starting material (by TLC), the reaction was quenched with satd NH$_4$Cl solution, and the reaction mixture was extracted with EtOAc (2×30 mL). The combined organic extracts were washed with H$_2$O (30 mL) and brine (30 mL), dried over anhydrous Na$_2$SO$_4$ and concentrated under reduced pressure to afford ketone V (0.37 g, crude). This was used in the next step without any further purification. $^1$H NMR (500 MHz, CDCl$_3$): δ 8.60 (s, 1H), 7.91-7.87 (m, 1H), 7.77-7.75 (m, 1H), 7.62 (d, J=7.0 Hz, 1H), 7.05-7.01 (m, 1H), 6.93-6.88 (m, 1H). MS (ESI): m/z 348 [M+H]$^+$.

To a stirred solution of ketone V (80 mg, crude) in Et$_2$O (10 mL) was added freshly prepared diazomethane [prepared by dissolving NMU (200 mg, 2.06 mmol) in a 1:1 mixture of 10% KOH solution (20 mL) and Et$_2$O (20 mL) at 0° C. followed by separation and drying of the organic layer using KOH pellets] at −5° C., and the reaction mixture was stirred for 2 h. The resulting reaction mixture was allowed to warm to RT, and stirring was continued for another 16 h. After complete consumption of the starting material (by TLC), the reaction mixture was concentrated under reduced pressure to obtain crude epoxide W (54 mg). The crude product was confirmed by $^1$H-NMR analysis and was used in the next reaction without further purification. $^1$H NMR (500 MHz, CDCl$_3$): δ 8.37 (s, 1H), 7.57-7.52 (m, 2H), 7.28-7.2 (m, 1H), 6.87-6.78 (m, 2H), 3.28 (d, J=5.0 Hz, 1H), 2.97-2.91 (m, 1H). MS (ESI): m/z 364 [M+2]$^+$.

To a stirred solution of epoxide W (120 mg, 0.33 mmol) in THF/H$_2$O (20 mL, 8:2) was added K$_2$CO$_3$ (137 mg, 0.99 mmol) followed by boronate I-F (110 mg, 0.363 mmol) at RT under inert atmosphere. After purging with N$_2$ for 45 min, Pd(dppf)$_2$Cl$_2$ (12 mg, 0.016 mmol) was added to the reaction mixture under an inert atmosphere, and the resulting mixture was stirred at 70° C. for 2 h. After complete consumption of the starting material (by TLC), the reaction mixture was allowed to cool to RT, diluted with H$_2$O (100 mL) and the aqueous layer was extracted with EtOAc (2×200 mL). The combined organic extracts were washed with H$_2$O (100 mL) and brine (100 mL), dried over anhydrous Na$_2$SO$_4$ and concentrated in vacuo. The crude material was purified by silica gel column chromatography (eluting with 5-6% EtOAc/hexane) to afford X (115 mg, 0.25 mmol, 75%) as a white solid. $^1$H NMR (200 MHz, CDCl$_3$): δ 8.63 (s, 1H), 8.03 (d, J=8.5 Hz, 2H), 7.75-7.69 (m, 2H), 7.31-7.28 (m, 1H), 7.06 (d, J=9.0 Hz, 2H), 6.86-6.83 (m, 1H), 6.81-6.77 (m, 1H), 4.42 (q, J=8.2 Hz, 2H), 3.32 (d, J=5.0 Hz, 1H), 2.98-2.97 (m, 1H). MS (ESI): m/z 456 [M−H]$^-$.

To a stirred solution of epoxide X (115 mg, 0.25 mmol) in dry DMF (10 mL) was added 1H-tetrazole (28 mg, 0.37 mmol) followed by K$_2$CO$_3$ (52 mg, 0.25 mmol) at RT under inert atmosphere. The reaction mixture was gradually heated up to 65° C. and stirred for 20 h. After complete consumption of the starting material (by TLC), the reaction mixture was diluted with ice-cold H$_2$O (30 mL) and extracted with EtOAc (2×50 mL). The separated organic layer was washed with H$_2$O (30 mL) and brine (30 mL), dried over anhydrous Na$_2$SO$_4$ and concentrated under reduced pressure to obtain crude product. The crude material was purified by silica gel column chromatography (eluting with 45% EtOAc/Hexane) to afford 36 (48 mg, 0.09 mmol, 36%) as an off-white solid. $^1$H NMR (500 MHz, CD$_3$OD): δ 8.66 (s, 1H), 8.42 (s, 1H), 7.99 (d, J=7.5 Hz, 2H), 7.63 (d, J=7.5 Hz, 1H), 7.55 (d, J=7.0 Hz, 1H), 7.10-7.03 (m, 3H), 6.81-6.79 (m, 1H), 6.68-6.64 (m, 1H), 5.73 (d, J=14.5 Hz, 1H), 5.14 (d, J=14.5 Hz, 1H), 4.44 (q, J=8.2 Hz, 2H), 4.35 (s, OH). HPLC: 96.1%. MS (ESI): m/z 528 [M+H]$^+$.

Example 15

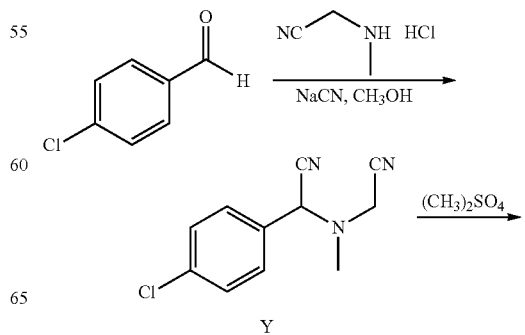

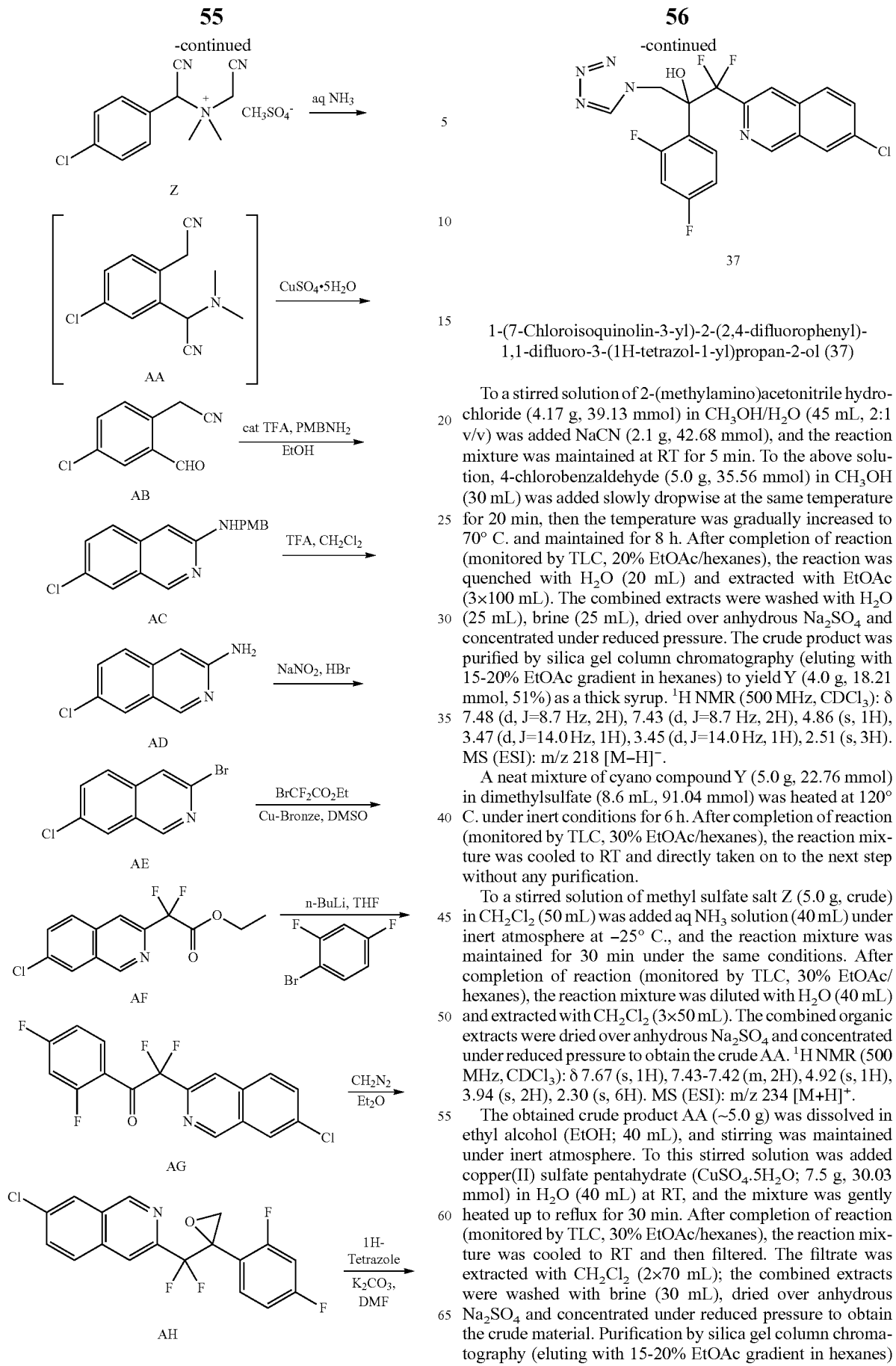

1-(7-Chloroisoquinolin-3-yl)-2-(2,4-difluorophenyl)-1,1-difluoro-3-(1H-tetrazol-1-yl)propan-2-ol (37)

To a stirred solution of 2-(methylamino)acetonitrile hydrochloride (4.17 g, 39.13 mmol) in $CH_3OH/H_2O$ (45 mL, 2:1 v/v) was added NaCN (2.1 g, 42.68 mmol), and the reaction mixture was maintained at RT for 5 min. To the above solution, 4-chlorobenzaldehyde (5.0 g, 35.56 mmol) in $CH_3OH$ (30 mL) was added slowly dropwise at the same temperature for 20 min, then the temperature was gradually increased to 70° C. and maintained for 8 h. After completion of reaction (monitored by TLC, 20% EtOAc/hexanes), the reaction was quenched with $H_2O$ (20 mL) and extracted with EtOAc (3×100 mL). The combined extracts were washed with $H_2O$ (25 mL), brine (25 mL), dried over anhydrous $Na_2SO_4$ and concentrated under reduced pressure. The crude product was purified by silica gel column chromatography (eluting with 15-20% EtOAc gradient in hexanes) to yield Y (4.0 g, 18.21 mmol, 51%) as a thick syrup. $^1$H NMR (500 MHz, $CDCl_3$): δ 7.48 (d, J=8.7 Hz, 2H), 7.43 (d, J=8.7 Hz, 2H), 4.86 (s, 1H), 3.47 (d, J=14.0 Hz, 1H), 3.45 (d, J=14.0 Hz, 1H), 2.51 (s, 3H). MS (ESI): m/z 218 [M−H]$^−$.

A neat mixture of cyano compound Y (5.0 g, 22.76 mmol) in dimethylsulfate (8.6 mL, 91.04 mmol) was heated at 120° C. under inert conditions for 6 h. After completion of reaction (monitored by TLC, 30% EtOAc/hexanes), the reaction mixture was cooled to RT and directly taken on to the next step without any purification.

To a stirred solution of methyl sulfate salt Z (5.0 g, crude) in $CH_2Cl_2$ (50 mL) was added aq $NH_3$ solution (40 mL) under inert atmosphere at −25° C., and the reaction mixture was maintained for 30 min under the same conditions. After completion of reaction (monitored by TLC, 30% EtOAc/hexanes), the reaction mixture was diluted with $H_2O$ (40 mL) and extracted with $CH_2Cl_2$ (3×50 mL). The combined organic extracts were dried over anhydrous $Na_2SO_4$ and concentrated under reduced pressure to obtain the crude AA. $^1$H NMR (500 MHz, $CDCl_3$): δ 7.67 (s, 1H), 7.43-7.42 (m, 2H), 4.92 (s, 1H), 3.94 (s, 2H), 2.30 (s, 6H). MS (ESI): m/z 234 [M+H]$^+$.

The obtained crude product AA (~5.0 g) was dissolved in ethyl alcohol (EtOH; 40 mL), and stirring was maintained under inert atmosphere. To this stirred solution was added copper(II) sulfate pentahydrate ($CuSO_4.5H_2O$; 7.5 g, 30.03 mmol) in $H_2O$ (40 mL) at RT, and the mixture was gently heated up to reflux for 30 min. After completion of reaction (monitored by TLC, 30% EtOAc/hexanes), the reaction mixture was cooled to RT and then filtered. The filtrate was extracted with $CH_2Cl_2$ (2×70 mL); the combined extracts were washed with brine (30 mL), dried over anhydrous $Na_2SO_4$ and concentrated under reduced pressure to obtain the crude material. Purification by silica gel column chromatography (eluting with 15-20% EtOAc gradient in hexanes)

afforded AB (1.2 g, 6.68 mmol, 29% overall yield from Y in three sequential steps). $^1$H NMR (500 MHz, CDCl$_3$): δ 10.03 (s, 1H), 7.82 (d, J=2.0 Hz, 1H), 7.65-7.62 (m, 2H), 4.23 (s, 2H). MS (ESI): m/z 178 [M–H]$^-$.

To a stirred solution of benzaldehyde AB (2.0 g, 11.13 mmol) in EtOH (25 mL) were added 4-methoxybenzylamine (PMBNH$_2$; 1.91 g, 13.92 mmol) and a catalytic amount of trifluoroacetic acid (TFA; 5 mol %) at RT, and the mixture was gradually heated to reflux temperature under inert atmosphere. After completion of reaction (8 h, monitored by TLC), the reaction mixture was cooled to RT and concentrated under reduced pressure. The obtained solid residue was subjected to crystallization (50% CH$_2$Cl$_2$/pentane) to afford colorless crystalline isoquinoline derivative AC (2.0 g, 6.69 mmol, 60%). $^1$H NMR (500 MHz, CDCl$_3$): δ 8.75 (s, 1H), 7.72 (s, 1H), 7.45 (d, J=8.5 Hz, 1H), 7.38 (d, J=8.5 Hz, 1H), 7.32 (d, J=9.0 Hz, 2H), 6.89 (d, J=9.0 Hz, 2H), 6.46 (s, 1H), 5.02 (br s, 1H), 4.43 (s, 2H), 3.80 (s, 3H). MS (ESI): m/z 299 [M+H]$^+$.

To a stirred solution of compound AC (2.0 g, 6.69 mmol) in CH$_2$Cl$_2$ (40 mL) was added TFA (20 mL) at RT and refluxed for 3 h under inert condition. After completion of reaction (monitored by TLC), the reaction mixture was cooled to RT, quenched with satd NaHCO$_3$ solution (40 mL) and extracted with CH$_2$Cl$_2$ (3×40 mL). The combined extracts were washed with brine (25 mL), dried over anhydrous Na$_2$SO$_4$ and evaporated in vacuo. The obtained crude material was purified by silica gel column chromatography (eluting with EtOAc/hexane) to afford amine AD (1.11 g, 6.21 mmol, 93%) as a yellowish solid. $^1$H NMR (500 MHz, CDCl$_3$): δ 8.78 (s, 1H), 7.75 (s, 1H), 7.48 (d, J=9.0 Hz, 1H), 7.42 (d, J=9.0 Hz, 1H), 6.70 (s, 1H), 4.48 (br s, 2H). MS (ESI): m/z 179 [M+H]$^+$.

To a stirred solution of amine AD (1.0 g, 5.60 mmol) in 48% aq hydrobromic acid (HBr) solution (4.8 mL) was added sodium nitrite (NaNO$_2$; 0.58 g, 8.40 mmol) in H$_2$O (20 mL) dropwise at 0° C. for 15 min, and the reaction mixture was maintained at the same temperature for 1 h. After completion of reaction (monitored by TLC, 40% EtOAc/hexanes), the reaction mixture was diluted with H$_2$O (20 mL), made basic (pH 8-9) with 2 N aq NaOH solution and then extracted with Et$_2$O (3×30 mL). The combined organic extracts were washed with brine (30 mL), dried over anhydrous Na$_2$SO$_4$ and evaporated in vacuo. The crude material was purified by silica gel column chromatography (eluting with 5-10% EtOAc gradient in hexanes) to afford compound AE (0.3 g, 1.23 mmol, 22%) as an off-white solid. $^1$H NMR (500 MHz, CDCl$_3$): δ 8.97 (s, 1H), 7.95 (s, 1H), 7.89 (s, 1H), 7.72 (d, J=8.5 Hz, 1H), 7.66 (d, J=8.5 Hz, 1H). MS (ESI): m/z 242 [M$^+$].

To a stirred suspension of Copper-Bronze (1.52 g, 8.25 mmol) in DMSO (10 mL) was added ethyl 2-bromo-2,2-difluoroacetate (0.55 mL, 4.13 mmol) at RT. After being stirred at RT for 1 h, compound AE (0.5 g, 2.06 mmol) was added portionwise, and the mixture was stirred for 16 h under inert atmosphere. After completion of reaction (by TLC), the reaction mixture was quenched with satd NH$_4$Cl solution (50 mL), filtered through a Celite® pad and washed with CH$_2$Cl$_2$ (3×50 mL). The separated organic layer was washed with brine (50 mL), dried over anhydrous Na$_2$SO$_4$ and concentrated under reduced pressure. The crude material was purified by silica gel column chromatography (eluting with 5-10% EtOAc in hexanes) to afford ester AF (0.25 g, 0.87 mmol, 42%) as a thick syrup. $^1$H NMR (500 MHz, CDCl$_3$): δ 9.20 (s, 1H), 8.12 (s, 1H), 8.03 (s, 1H), 7.91 (d, J=8.5 Hz, 1H), 7.75 (d, J=8.5 Hz, 1H), 4.38 (q, J=7.0 Hz, 2H), 1.33 (t, J=7.0 Hz, 3H). MS (ESI): m/z 286 [M+H]$^+$.

To a stirred solution of 1-bromo-2,4-difluorobenzene (68 mg, 0.35 mmol) in Et$_2$O (6 mL) was added n-BuLi (1.6 M in hexanes; 0.22 mL, 0.35 mmol) dropwise at −78° C. under inert atmosphere, and the mixture was stirred for 20 min. A solution of ester AF (100 mg, 0.35 mmol) in Et$_2$O (5 mL) was added to the reaction mixture at −78° C., and stirring was continued at the same temperature for 1 h and then at RT for 15 min. Progress of the reaction was monitored by TLC. The reaction was quenched with satd NH$_4$Cl solution, and the mixture was extracted with EtOAc (2×25 mL). The combined organic extracts were washed with H$_2$O (20 mL) and brine (20 mL), dried over anhydrous Na$_2$SO$_4$ and concentrated under reduced pressure to afford ketone AG (100 mg, crude). The crude material was taken on to the next step without further purification. MS (ESI): m/z 354 [M+H]$^+$.

To a stirred solution of ketone AG (500 mg, crude) in Et$_2$O (25 mL) was added freshly prepared diazomethane [prepared by dissolving NMU (1.0 g, 9.71 mmol) in a mixture of 10% aq KOH solution (50 mL) and Et$_2$O (25 mL) at 0° C. followed by separation and drying of the organic layer using KOH pellets] at 0° C., and the reaction mixture was maintained at 0° C.—RT for 4 h. The progress of the reaction was monitored by TLC (20% EtOAc/hexanes). The reaction mixture was concentrated under reduced pressure to afford crude product. The crude material was purified by silica gel column chromatography (eluting with 10-15% EtOAc gradient in hexanes) followed by preparative HPLC to afford the epoxide AH (70 mg, 0.19 mmol, 13% from ester AF in two steps). $^1$H NMR (500 MHz, CDCl$_3$): δ 9.21 (s, 1H), 8.02 (s, 1H), 7.85 (s, 1H), 7.82 (d, J=9.0 Hz, 1H), 7.71 (d, J=9.0 Hz, 1H), 7.43-7.26 (m, 1H), 6.79-6.62 (m, 1H), 6.72-6.68 (m, 1H), 3.53 (d, J=5.0 Hz, 1H), 3.01 (d, J=5.0 Hz, 1H). HPLC: 99.9%. MS (ESI): m/z 368 [M+H]$^+$.

To a stirred solution of epoxide AH (70 mg, 0.19 mmol) in dry DMF (5 mL) was added 1H-tetrazole (20 mg, 0.28 mmol) followed by K$_2$CO$_3$ (26.3 mg, 0.19 mmol) at RT under inert atmosphere. The resulting reaction mixture was gradually heated up to 65° C. and stirred for 16 h; progress of the reaction was monitored by TLC. The reaction mixture was then diluted with ice-cold H$_2$O and extracted with EtOAc (2×30 mL). The combined organic extracts were dried over anhydrous Na$_2$SO$_4$ and concentrated under reduced pressure. The obtained crude material was purified by silica gel column chromatography (eluting with 40-45% EtOAc gradient in hexanes) to afford 37 (32 mg, 0.07 mmol, 38%) as off-white solid. $^1$H NMR (500 MHz, CDCl$_3$): δ 9.08 (s, 1H), 8.77 (s, 1H), 8.04 (s, 1H), 7.97 (s, 1H), 7.85 (d, J=8.5 Hz, 1H), 7.77-7.75 (m, 2H), 7.39-7.34 (m, 1H), 6.77-6.72 (m, 1H), 6.63-6.59 (m, 1H), 5.62 (d, J=14.5 Hz, 1H), 5.13 (d, J=14.5 Hz, 1H). HPLC: 99.9%. MS (ESI): m/z 438 [M+H]$^+$.

Example 16

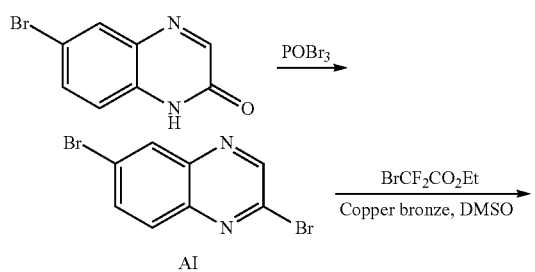

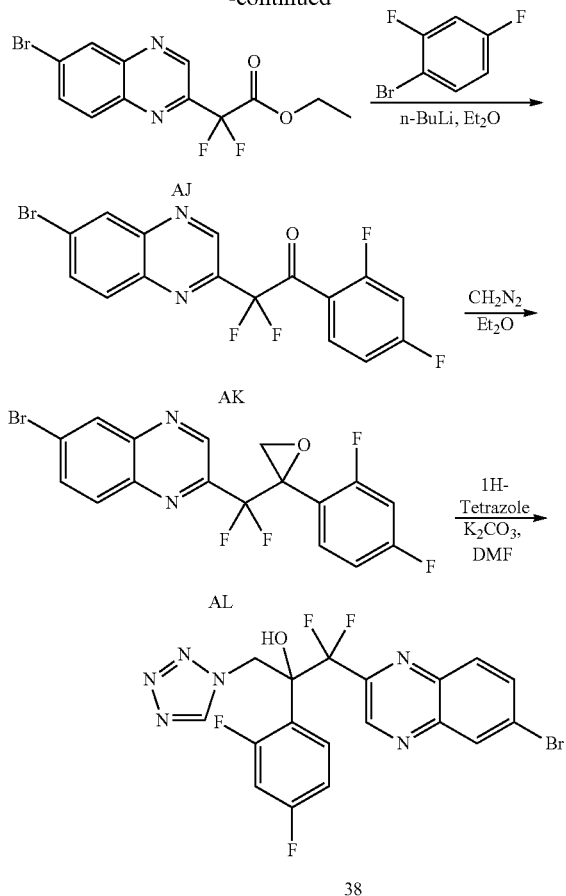

1-(6-Bromoquinoxalin-2-yl)-2-(2,4-difluorophenyl)-1,1-difluoro-3-(1H-tetrazol-1-yl)propan-2-ol (38)

To 6-bromoquinoxalin-2(1H)-one (250 mg, 1.11 mmol) was added $POBr_3$ (500 mg, 2.61 mmol) at RT. The reaction mixture was gradually heated to 130° C. and stirred for 2 h. After completion of reaction (by TLC), the reaction mixture was cooled to 0° C., neutralized with satd $NaHCO_3$ solution (50 mL) and extracted with EtOAc (2×50 mL). The combined organic extracts were washed with $H_2O$ (50 mL) and brine (50 mL), dried over anhydrous $Na_2SO_4$ and concentrated under reduced pressure to obtain the crude material. Purification by silica gel column chromatography (eluting with 10% EtOAc/hexane) afforded compound AI (160 mg, 0.55 mmol, 50%) as an off-white solid. $^1$H NMR (200 MHz, $CDCl_3$): δ 8.84 (s, 1H), 8.30 (d, J=9.0 Hz, 1H), 7.96-7.82 (m, 2H).

To a stirred suspension of copper-bronze (380 mg, 2.08 mmol) in DMSO (2 mL) was added ethyl 2-bromo-2,2-difluoroacetate (0.15 mL, 1.04 mmol) at RT, and the mixture was stirred for 1 h. A solution of compound AI (150 mg, 0.52 mmol) in DMSO (3 mL) was added to the reaction mixture, and the stirring was continued for another 16 h at RT. After completion of reaction (by TLC), the reaction mixture was quenched with satd $NH_4Cl$ solution (100 mL) and extracted with EtOAc (2×150 mL). The combined organic extracts were washed with $H_2O$ (100 mL) and brine (100 mL), dried over anhydrous $Na_2SO_4$ and concentrated under reduced pressure to obtain the crude material. Purification by silica gel column chromatography (eluting with 20% EtOAc/hexane) afforded ester AJ (120 mg, 0.34 mmol, 69%) as an off-white solid. $^1$H NMR (200 MHz, $CDCl_3$): δ 9.22 (s, 1H), 8.34 (dd, J=8.0, 1.5 Hz, 1H), 8.02-7.94 (m, 2H), 4.40 (q, J=7.0 Hz, 2H), 1.36 (t, J=7.0 Hz, 3H). MS (ESI): m/z 331 [M]$^+$.

To a stirred solution of 1-bromo-2,4-difluorobenzene (0.1 mL, 0.36 mmol) in $Et_2O$ (5 mL) was added n-BuLi (1.6 M solution in hexane; 0.22 mL, 0.36 mmol) at −78° C., and the mixture was stirred for 30 min under inert atmosphere. A solution of ester AJ (0.31 g, 0.94 mmol) in $Et_2O$ (5 mL) was added to the reaction mixture at −78° C., and stirring was continued for another 5 min. Progress of the reaction was monitored by TLC. The reaction was quenched with satd $NH_4Cl$ solution (40 mL), and the reaction mixture was extracted with EtOAc (2×50 mL). The combined organic extracts were washed with $H_2O$ (40 mL) and brine (40 mL), dried over anhydrous $Na_2SO_4$ and concentrated under reduced pressure to obtain the crude material. Purification by silica gel column chromatography (eluting with 20% EtOAc/hexane) afforded ketone AK (0.1 g, 0.65 mmol, 69%) as an off-white solid. $^1$H NMR (200 MHz, $CDCl_3$): δ 9.31 (s, 1H), 8.40 (s, 1H), 8.22-7.88 (m, 3H), 7.10-6.92 (m, 1H), 6.83-6.78 (m, 1H). MS (ESI): m/z 399 [M]$^+$.

To a stirred solution of ketone AK (0.35 g, 0.87 mmol) in $Et_2O$ (15 mL) was added freshly prepared diazomethane [prepared by dissolving NMU (1.27 g, 12.5 mmol) in a 1:1 mixture of 10% KOH solution (10 mL) and $Et_2O$ (10 mL) at 0° C. followed by separation and drying of the organic layer using KOH pellets] at 0° C. and stirred for 30 min. The reaction mixture was allowed to warm to RT, and stirring was continued for another 4 h. Progress of the reaction was monitored by TLC. The reaction mixture was concentrated under reduced pressure to afford the crude product. Purification by silica gel column chromatography (eluting with 10% EtOAc/Hexane) afforded the epoxide AL (0.24 g, 0.74 mmol, 85%) as a yellow syrup. $^1$H NMR (500 MHz, $CDCl_3$): δ 8.99 (s, 1H), 8.18 (s, 1H), 8.10-8.05 (m, 1H), 7.96-7.85 (m, 1H), 7.49-7.41 (m, 1H), 6.88-6.82 (m, 1H), 6.79-6.75 (m, 1H), 3.46 (d, J=5.0 Hz, 1H), 3.03 (d, J=5.0 Hz, 1H). MS (ESI): m/z 414 [M+H]$^+$.

To a stirred solution of epoxide AL (140 mg, 0.34 mmol) in dry DMF (5 mL) was added 1H-tetrazole (36 mg, 0.61 mmol) followed by $K_2CO_3$ (56 mg, 0.45 mmol) at RT under inert atmosphere. The resulting reaction mixture was gradually heated up to 65° C. and stirred for 16 h. Progress of the reaction was monitored by TLC. The reaction mixture was diluted with ice-cold $H_2O$ (40 mL) and extracted with EtOAc (2×50 mL). The combined organic extracts were washed with $H_2O$ (40 mL) and brine (40 mL), dried over anhydrous $Na_2SO_4$ and concentrated under reduced pressure to obtain the crude material. Purification by silica gel column chromatography (eluting with 40% EtOAc/Hexane) to afford 38 (30 mg, 0.06 mmol, 18.4%) as a colorless thick gum. $^1$H NMR (500 MHz, $CDCl_3$): δ 9.00 (s, 1H), 8.73 (s, 1H), 8.37 (s, 1H), 8.06-7.93 (m, 2H), 7.25-7.24 (m, 1H), 6.81-6.77 (m, 1H), 6.67-6.65 (m, 1H), 5.81 (s, OH), 5.72 (d, J=14.5 Hz, 1H), 5.21 (d, J=14.5 Hz, 1H). HPLC: 96.5%. MS (ESI): m/z 485 [M+2]$^+$.

Example 17

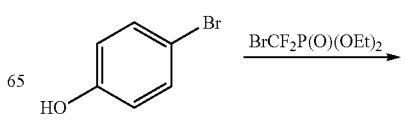

1-(5-(4-(Difluoromethoxy)phenyl)pyrazin-2-yl)-2-(2, 4-difluorophenyl)-1,1-difluoro-3-(1H-tetrazol-1-yl) propan-2-ol (39)

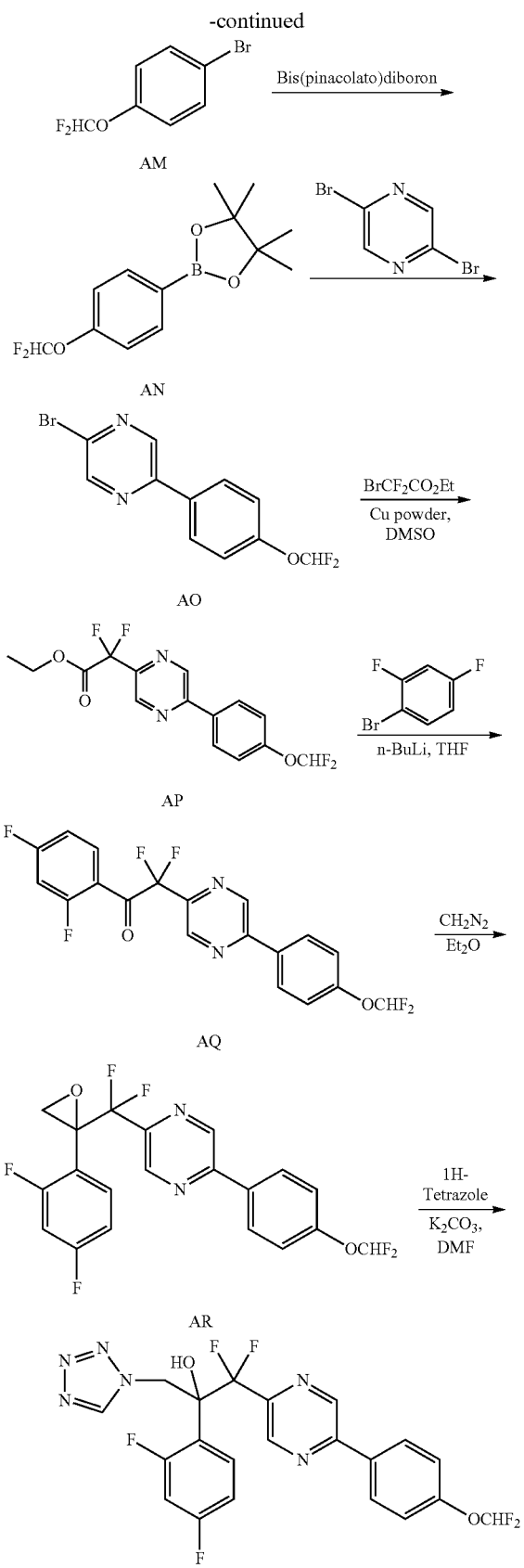

To a stirred solution of 4-bromophenol (5 g, 28.90 mmol) in acetonitrile (350 mL) was added a solution of KOH (32.5 g, 580.35 mmol) in H$_2$O (350 mL) at 0° C., and the mixture was maintained for 5 min. To this mixture, diethyl (bromodifluoromethyl)phosphonate (9.25 mL, 52.02 mmol) was added slowly at same temperature over 15 min (exothermic reaction), and the mixture was allowed to stir at RT. After being stirred for 10 h at RT, the reaction mixture was diluted with EtOAc (100 mL), and the organic layer was separated. The organic layer was washed with H$_2$O (40 mL) and brine (40 mL), dried over anhydrous Na$_2$SO$_4$ and concentrated under reduced pressure to obtain the crude material. Purification by silica gel column chromatography (eluting with 5-10% EtOAc gradient in hexanes) afforded AM (3.0 g, 13.45 mmol, 46%). $^1$H NMR (500 MHz, CDCl$_3$): δ 7.48 (d, J=8.5 Hz, 2H), 7.01 (d, J=8.5 Hz, 2H), 6.48 (t, J$_{F-H}$=74.0 Hz, 1H).

To a stirred solution of bromophenol derivative AM (2.0 g, 8.97 mmol) in 1,4-dioxane (40 mL) were added bis(pinacolato)diboron (2.28 g, 8.97 mmol) and KOAc (2.64 g, 26.90 mmol) at RT under inert atmosphere, and the mixture was degassed for 20 min by purging with argon. To this solution, Pd(dppf)$_2$Cl$_2$ (0.33 g, 0.45 mmol) was added, and the mixture was degassed for a further 10 min. The reaction mixture was then heated to 80° C. and stirred for 3 h at this temperature. Progress of the reaction was monitored by TLC. The reaction mixture was then cooled to RT and diluted with EtOAc (30 mL). The resultant solution was filtered through a Celite® pad, and the filtrate was then concentrated in vacuo. The crude compound was purified by silica gel column chromatography (eluting with 5-10% EtOAc gradient in hexanes) to afford AN (1.72 g, 6.37 mmol, 71%). $^1$H NMR (500 MHz, CDCl$_3$): δ 7.81 (d, J=8.5 Hz, 2H), 7.09 (d, J=8.5 Hz, 2H), 6.54 (t, J$_{F-H}$=74.0 Hz, 1H), 1.34 (s, 12H). A stirring solution of 2,5-dibromopyrazine (1.32 g, 5.55 mmol), boronate AN (1.5 g, 5.55 mmol) and K$_2$CO$_3$ (2.27 g, 16.45 mmol) in THF-H$_2$O (4:1; 25 mL) at RT was degassed by purging with argon for 20 min. To this solution, Pd(dppf)$_2$Cl$_2$ (0.4 g, 0.55 mmol) was added, and the mixture was degassed further for 10 min. The resultant reaction mixture was maintained at the same temperature for 18 h; progress of the reaction was monitored by TLC. The reaction mixture was diluted with EtOAc (30 mL). The organic layer was separated and the aqueous layer was extracted with EtOAc (2×20 mL). The combined organic layers were washed with brine (30 mL), dried over anhydrous Na$_2$SO$_4$ and concentrated under reduced pressure to obtain the crude compound. Purification by silica gel column chromatography (eluting with 5-10% EtOAc gradient in hexanes) afforded AO (0.9 g, 2.99 mmol, 54%). $^1$H NMR (500 MHz, CDCl$_3$): δ 8.75 (s, 1H), 8.71 (s, 1H), 8.01 (d, J=9.0 Hz, 2H), 7.28 (d, J=9.0 Hz, 2H), 6.58 (t, J$_{F-H}$=74.0 Hz, 1H).

To a stirred suspension of copper powder (770 mg, 12.12 mmol) in DMSO (8 mL) was added ethyl 2-bromo-2,2-difluoroacetate (0.77 mL, 6.0 mmol) at RT, and the mixture was stirred for 1 h. A solution of compound AO (900 mg, 2.99 mmol) in DMSO (2 mL) was added to the reaction mixture and stirring was continued for another 18 h at RT. After completion of reaction (by TLC), the reaction mixture was quenched with satd NH$_4$Cl solution and filtered through a Celite® pad. The Celite® pad was washed with CH$_2$Cl$_2$ (3×50 mL). The separated organic layer was washed with brine, dried over anhydrous Na$_2$SO$_4$ and concentrated under reduced pressure. The crude material was purified by silica gel column chromatography (eluting with 8% EtOAc in hexanes) to afford ester AP (600 mg, 1.74 mmol, 58%). $^1$H NMR (500 MHz, CDCl$_3$): δ 9.02 (s, 1H), 9.01 (s, 1H), 8.09 (d, J=9.0 Hz, 2H), 7.28 (d, J=9.0 Hz, 2H), 6.60 (t, J$_{F-H}$=73.0 Hz, 1H), 4.40 (q, J=7.0 Hz, 2H), 1.35 (t, J=7.0 Hz, 3H). MS (ESI): m/z 345 [M+H]$^+$.

To a stirred solution of 1-bromo-2,4-difluorobenzene (196 mg, 1.01 mmol) in Et$_2$O (10 mL) was added n-BuLi (2.5 M in hexanes; 0.43 mL, 1.01 mmol) dropwise at −78° C. under inert atmosphere, and the mixture was stirred for 40 min. A solution of ester AP (350 mg, 1.01 mmol) in THF (5 mL) was added to the reaction mixture at −78° C., and stirring was continued for another 10 min. The progress of the reaction was monitored by TLC. The reaction was quenched with satd NH$_4$Cl solution, and the mixture was extracted with EtOAc (2×25 mL). The combined organic extracts were washed with brine, dried over anhydrous Na$_2$SO$_4$ and concentrated under reduced pressure to afford ketone AQ (350 mg, crude). The crude product AQ was confirmed by $^1$H-NMR analysis and was taken to the next step without any further purification. $^1$H NMR (500 MHz, CDCl$_3$): δ 9.10 (s, 1H), 8.95 (s, 1H), 8.11-8.07 (m, 3H), 7.29-7.26 (m, 2H), 7.04-7.01 (m, 1H), 6.87-6.85 (m, 1H), 6.60 (t, J$_{F-H}$=73.0 Hz, 1H). MS (ESI): m/z 413 [M+H]$^+$.

To a stirred solution of ketone AQ (350 mg, crude) in Et$_2$O (15 mL) was added freshly prepared diazomethane [prepared by using dissolving NMU (438 mg, 4.25 mmol) in a mixture of 10% aq KOH solution (50 mL) and Et$_2$O (25 mL) at 0° C. followed by separation and drying of the organic layer using KOH pellets] at 0° C., and the mixture was stirred for 3 h. The resulting reaction mixture was allowed to stir at RT for another 30 min. The progress of the reaction was monitored by TLC. The reaction mixture was concentrated under reduced pressure to afford the crude product. Purification by silica gel column chromatography (eluting with 15-20% EtOAc gradient in hexanes) afforded the epoxide AR (160 mg, 0.37 mmol, 37% from ester AP in two steps). $^1$H NMR (500 MHz, CDCl$_3$): δ 9.02 (s, 1H), 8.75 (s, 1H), 8.09 (d, J=9.0 Hz, 2H), 7.45-7.42 (m, 1H), 7.28 (d, J=9.0 Hz, 2H), 6.89-6.83 (m, 1H), 6.78-6.75 (m, 1H), 6.60 (t, J$_{F-H}$=73.0 Hz, 1H), 3.47 (d, J=5.0 Hz, 1H), 3.03 (d, J=5.0 Hz, 1H).

To a stirred solution of epoxide AR (160 mg, 0.37 mmol) in dry DMF (5 mL) was added 1H-tetrazole (40 mg, 0.57 mmol) followed by K$_2$CO$_3$ (52 mg, 0.37 mmol) at RT under an inert atmosphere. The resulting reaction mixture was gradually heated up to 65° C. and stirred for 18 h. The progress of the reaction was monitored by TLC. The reaction mixture was diluted with ice-cold H$_2$O and extracted with EtOAc (2×30 mL). The combined organic extracts were dried over anhydrous Na$_2$SO$_4$ and concentrated under reduced pressure. The obtained crude material was purified by silica gel column chromatography (eluting with 45-50% EtOAc gradient in hexanes) to afford 39 (60 mg, 0.12 mmol, 32%) as a white solid. $^1$H NMR (500 MHz, CDCl$_3$): δ 8.89 (s, 1H), 8.81 (s, 1H), 8.72 (s, 1H), 8.07 (d, J=9.0 Hz, 2H), 7.35-7.31 (m, 1H), 7.28 (d, J=9.0 Hz, 2H), 6.81-6.77 (m, 1H), 6.75-6.69 (m, 1H), 6.60 (t, J$_{F-H}$=73.0 Hz, 1H), 6.01 (s, OH), 5.64 (d, J=15.0 Hz, 1H), 5.18 (d, J=15.0 Hz, 1H). HPLC: 95.07%. MS (ESI): m/z 497 [M+H]$^+$.

Compounds 40-48 in Table 1 were prepared using the same conditions as compound 39 from commercially available starting materials or prepared intermediates (given in Table 1).

Example 18

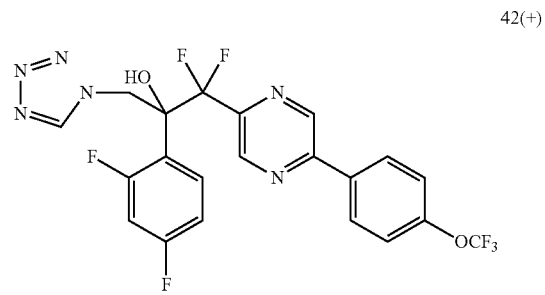 [SMILES: N=N/N=C\NCC(O)(c1ccc(F)cc1F)C(F)(F)c1cnc(-c2ccc(OC(F)(F)F)cc2)cn1]

42(+)

Chiral Preparative HPLC Separation of Enantiomers of 42

The enantiomers of 42 (300 mg, 0.58 mmol) were separated by preparative HPLC using a CHIRALPAK IC® column (250×20 mm, 5μ) with mobile phase (A) n-hexane—(B) EtOH (A:B=90:10) and flow rate 15 mL/min to obtain 42(+) (90 mg, 0.17 mmol, 30%) as a white solid.

Analytical Data:

Chiral HPLC: 100% ee, R$_t$=15.22 min (CHIRALPAK IC® column, 250×4.6 mm, 5μ; mobile phase (A) n-hexane—(B) EtOH (A:B=90:10); flow rate: 1.00 mL/min). Optical rotation [α]$_D^{25}$: +33.04° (c=0.1% in CH$_3$OH). $^1$H NMR (500 MHz, CDCl$_3$): δ 8.90 (s, 1H), 8.82 (s, 1H), 8.72 (s, 1H), 8.09 (d, J=9.0 Hz, 2H), 7.38 (d, J=9.0 Hz, 2H), 7.35-7.31 (m, 1H), 6.82-6.77 (m, 1H), 6.73-6.69 (m, 1H), 5.97 (s, OH), 5.64 (d, J=15.0 Hz, 1H), 5.20 (d, J=15.0 Hz, 1H). HPLC: 99.78%. MS (ESI): m/z 515 [M+H]$^+$.

Example 19

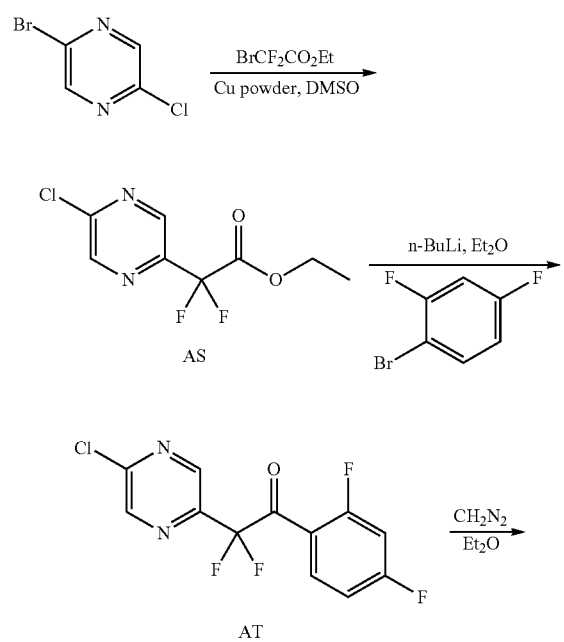

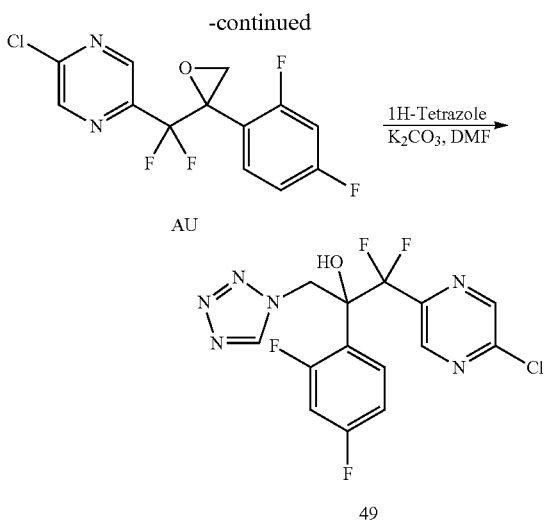

1-(5-Chloropyrazin-2-yl)-2-(2,4-difluorophenyl)-1,1-difluoro-3-(1H-tetrazol-1-yl)propan-2-ol (49)

To a stirred suspension of copper powder (3.0 g, 46.51 mmol) in DMSO (10 mL) was added ethyl 2-bromo-2,2-difluoroacetate (4.7 g, 23.15 mmol) at RT, and the mixture was stirred at RT for 1 h under inert atmosphere. A solution of 2-bromo-5-chloropyrazine (3.0 g, 15.54 mmol) in DMSO (20 mL) was added to the reaction mixture, and stirring was continued for another 16 h at RT. After the consumption of starting material (by TLC), the reaction mixture was diluted with aq NH₄Cl solution (40 mL), filtered through a Celite® pad and washed with CH₂Cl₂ (3×25 mL). The collected filtrate was washed with H₂O (30 mL) and brine (30 mL), dried over anhydrous Na₂SO₄ and concentrated under reduced pressure to obtain the crude material. Purification by column chromatography (eluting with 20% EtOAc/hexane) afforded ester AS (1.12 g, 4.73 mmol, 31%) as a liquid. $^1$H NMR (500 MHz, CDCl₃): δ 8.78 (s, 1H), 8.62 (s, 1H), 4.38 (q, J=7.0 Hz, 2H), 1.37 (t, J=7.0 Hz, 3H).

To a stirred solution of 1-bromo-2,4-difluorobenzene (0.98 g, 5.08 mmol) in Et₂O (20 mL) was added n-BuLi (1.6 M in hexane; 3.2 mL, 5.08 mmol) dropwise at −78° C., and the mixture was stirred for 30 min A solution of compound AS (0.6 g, 2.54 mmol) in Et₂O (8 mL) was added to the reaction mixture at −78° C., and stirring was continued for another 5 min. After consumption of the starting material (by TLC), the reaction mixture was quenched with satd NH₄Cl solution (20 mL) and extracted with EtOAc (2×50 mL). The combined organic extracts were washed with H₂O (40 mL) and brine (40 mL), dried over anhydrous Na₂SO₄ and concentrated under reduced pressure to afford ketone AT (0.7 g, crude), which was taken on to the next reaction without further purification. $^1$H NMR (500 MHz, CDCl₃): δ 8.87 (s, 1H), 8.57 (s, 1H), 8.07-8.02 (m, 1H), 7.06-7.02 (m, 1H), 6.90-6.84 (m, 1H).

To a stirred solution of ketone AT (0.6 g, crude) in Et₂O (10 mL) was added freshly prepared diazomethane [prepared by dissolving NMU (1.0 g, 9.70 mmol) in 10% aq KOH (50 mL) and Et₂O (50 mL) at 0° C. followed by separation and drying of the organic layer using KOH pellets] at 0° C., and stirring was continued for 30 min at 0° C. The resulting reaction mixture was allowed to warm to RT and stirred for 16 h. The progress of the reaction was monitored by TLC. The reaction mixture was concentrated under reduced pressure. The crude material was purified by silica gel column chromatography (eluting with 20% EtOAc/hexane) to afford the epoxide AU (0.27 g, 0.84 mmol, 33% over two steps from compound AS) as a semi solid. $^1$H NMR (500 MHz, CDCl₃): δ 8.62 (s, 1H), 8.51 (s, 1H), 7.42-7.37 (m, 1H), 6.89-6.86 (m, 1H), 6.79-6.77 (m, 1H), 3.43 (d, J=5.0 Hz, 1H), 3.00 (d, J=5.0 Hz, 1H).

To a stirred solution of epoxide AU (200 mg, 0.62 mmol) in dry DMF (6 mL) were added 1H-tetrazole (65 mg, 0.93 mmol) and K₂CO₃ (86 mg, 0.62 mmol) at RT under inert atmosphere. The resulting reaction mixture was gradually heated up to 70° C. and stirred for 16 h. After consumption of the starting material (by TLC), the reaction mixture was cooled to RT, diluted with H₂O (30 mL) and extracted with EtOAc (2×25 mL). The combined organic extracts were washed with H₂O (30 mL) and brine (30 mL), dried over anhydrous Na₂SO₄ and concentrated under reduced pressure to get crude mixture. The crude material was purified by silica gel column chromatography (eluting with 45% EtOAc/hexane) to afford 49 (15 mg, 0.038 mmol, 6.2%) as an off-white solid. $^1$H NMR (500 MHz, CDCl₃): δ 8.65 (s, 1H), 8.59 (s, 1H), 8.56 (s, 1H), 7.28-7.25 (m, 1H), 6.81-6.74 (m, 2H), 5.63 (d, J=14.0 Hz, 1H), 5.23 (s, OH), 5.15 (d, J=14.0 Hz, 1H). HPLC: 95.27%. MS (ESI): m/z 390[M+2]⁺.

Example 20

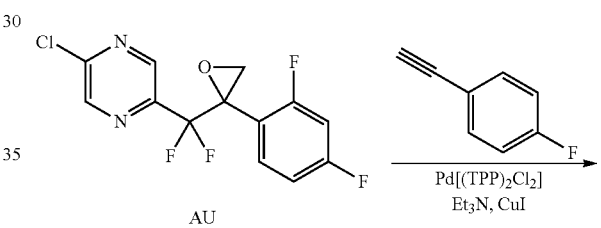

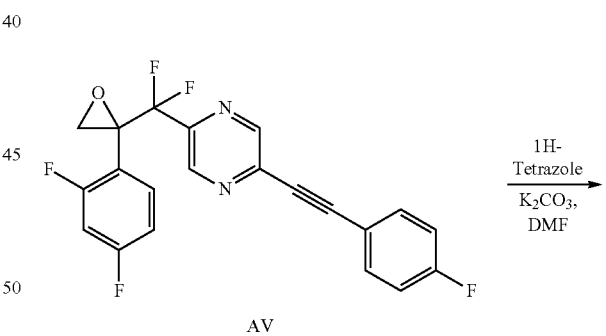

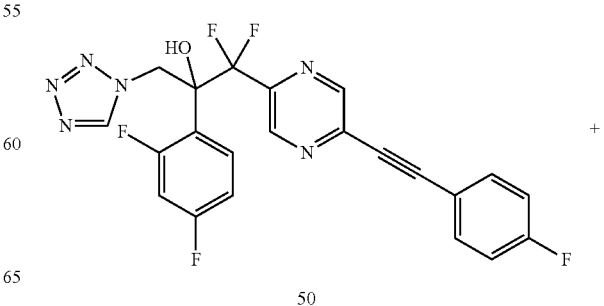

-continued

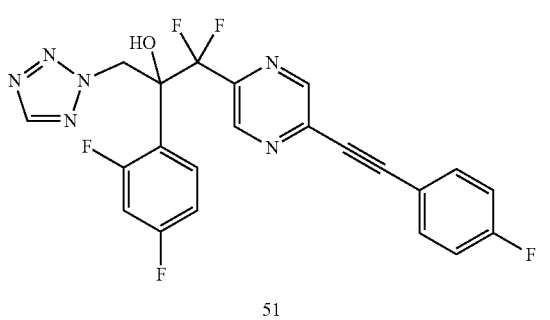

51

2-(2,4-Difluorophenyl)-1,1-difluoro-1-(5-((4-fluorophenyl)ethynyl)pyrazin-2-yl)-3-(1H-tetrazol-1-yl)propan-2-ol (50) and 2-(2,4-difluorophenyl)-1,1-difluoro-1-(5-((4-fluorophenyl)ethynyl)pyrazin-2-yl)-3-(2H-tetrazol-2-yl)propan-2-ol (51)

To a stirred solution of epoxide AU (94 mg, 0.29 mmol), 1-ethynyl-4-fluorobenzene (57 mg, 0.47 mmol), Et$_3$N (0.1 mL, 0.72 mmol) in THF (15 mL) was added copper(I) iodide (CuI; 3 mg, 0.015 mmol) at RT. After purging with inert gas for 10 min, dichlorobis(triphenylphosphine)palladium(II) (Pd (PPh$_3$)$_2$Cl$_2$; 10.4 mg, 0.15 mmol) was added to the reaction mixture under inert atmosphere. The reaction mixture was gradually heated up to 70° C. and stirred for 3 h. After consumption of the starting material (by TLC), the reaction mixture was filtered through a pad of Celite® and washed with EtOAc (4×15 mL). The filtrate was washed with H$_2$O (50 mL), dried over anhydrous Na$_2$SO$_4$ and concentrated under reduced pressure. The crude material was purified by silica gel column chromatography (eluting with 20% EtOAc/Hexane) to afford compound AV (40 mg, 0.099 mmol, 33%) as a pale-yellow solid. $^1$H NMR (500 MHz, CDCl$_3$): δ 8.74 (s, 1H), 8.69 (s, 1H), 7.63 (dd, J=9.0, 5.5 Hz, 2H), 7.42-7.38 (m, 1H), 7.12-7.09 (m, 2H), 6.89-6.86 (m, 1H), 6.79-6.75 (m, 1H), 3.46 (d, J=4.5 Hz, 1H), 3.01 (d, J=4.5 Hz, 1H).

To a stirred solution of epoxide AV (260 mg, 0.65 mmol) in dry DMF (10 mL) were added sequentially K$_2$CO$_3$ (90 mg, 0.65 mmol) and 1H-tetrazole (70 mg, 0.97 mmol) at RT under an inert atmosphere. The reaction mixture was gradually heated up to 65° C. and stirred for 16 h. After consumption of the starting material (by TLC), the reaction mixture was cooled to RT, diluted with H$_2$O (50 mL) and extracted with EtOAc (2×50 mL). The separated organic layer was dried over anhydrous Na$_2$SO$_4$ and concentrated under reduced pressure to obtain the crude material. Purification by silica gel column chromatography afforded 51 (15 mg, 0.03 mmol, 4.6%) (eluting with 25% EtOAc/hexane) as an off-white solid and 50 (30 mg, 0.06 mmol, 9.2%) (eluting with 35% EtOAc/hexane) as a light brown solid. 50: $^1$H NMR (500 MHz, CDCl$_3$): δ 8.74 (s, 1H), 8.71 (s, 1H), 8.62 (s, 1H), 7.63-7.60 (dd, J=13.5, 7.5 Hz, 2H), 7.30-7.28 (m, 1H), 7.13-7.09 (m, 2H), 6.81-6.77 (m, 1H), 6.74-6.70 (m, 1H), 5.64 (d, J=14.5 Hz, 1H), 5.61 (s, OH), 5.17 (d, J=14.5 Hz, 1H). HPLC: 93.5%. MS (ESI): m/z 472 [M−H]$^-$. 51: $^1$H NMR (500 MHz, CDCl$_3$): δ 8.72 (s, 1H), 8.62 (s, 1H), 8.38 (s, 1H), 7.64-7.62 (m, 2H), 7.30-7.27 (m, 1H), 7.12-7.09 (m, 2H), 6.81-6.77 (m, 1H), 6.72-6.69 (m, 1H), 6.02 (d, J=14.5 Hz, 1H), 5.37 (d, J=14.5 Hz, 1H), 5.10 (s, OH). HPLC: 98.3%. MS (ESI): m/z 472 [M−H]$^-$.

Example 21

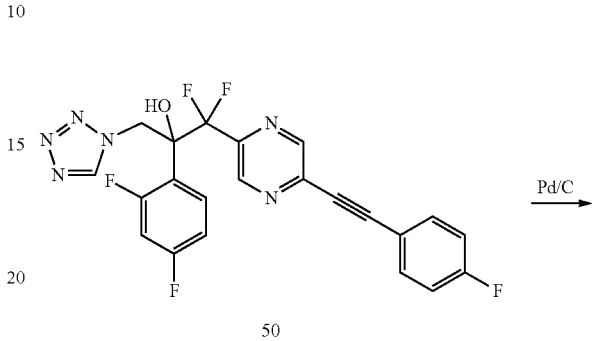

50

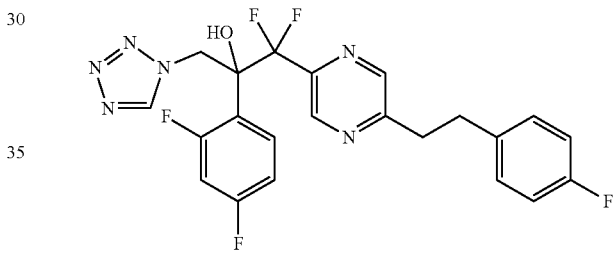

52

2-(2,4-Difluorophenyl)-1,1-difluoro-1-(5-(4-fluorophenethyl)pyrazin-2-yl)-3-(1H-tetrazol-1-yl)propan-2-ol (52)

To a stirred solution of 50 (25 mg, 0.053 mmol) in EtOAc (10 mL) was added 10% palladium on carbon (Pd/C; 5 mg) under inert atmosphere, and the mixture was stirred at RT for 2 h under H$_2$ atmosphere (balloon pressure). After consumption of the starting material (by TLC), the reaction mixture was filtered through a pad of Celite® and washed with EtOAc (3×10 mL). The filtrate was concentrated under reduced pressure to obtain the crude material. Purification by silica gel column chromatography (eluting with 30% EtOAc/hexane) afforded 52 (22 mg, 0.046 mmol, 88%) as a brown semi-solid. $^1$H NMR (500 MHz, CDCl$_3$): δ 8.72 (s, 1H), 8.70 (s, 1H), 8.18 (s, 1H), 7.28-7.24 (m, 1H), 7.07-7.05 (m, 2H), 6.96-6.93 (m, 2H), 6.80-6.76 (m, 1H), 6.70-6.67 (m, 1H), 6.08 (s, OH), 5.59 (d, J=14.5 Hz, 1H), 5.15 (d, J=14.5 Hz, 1H), 3.15 (t, J=7.0 Hz, 2H), 3.05 (t, J=7.0 Hz, 2H). HPLC: 88.8%. MS (ESI): m/z 477 [M+H]$^+$.

Example 22

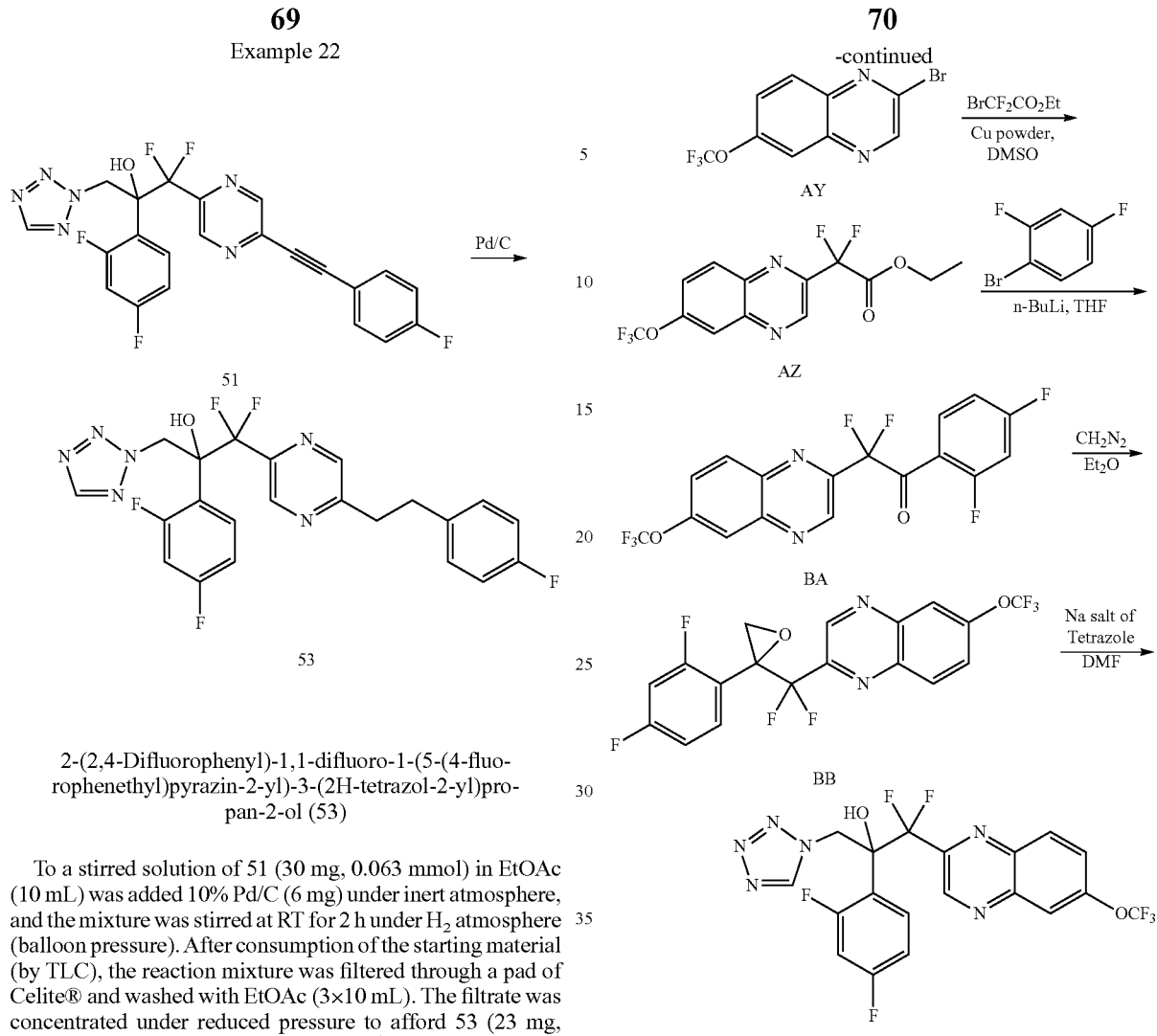

2-(2,4-Difluorophenyl)-1,1-difluoro-1-(5-(4-fluorophenethyl)pyrazin-2-yl)-3-(2H-tetrazol-2-yl)propan-2-ol (53)

To a stirred solution of 51 (30 mg, 0.063 mmol) in EtOAc (10 mL) was added 10% Pd/C (6 mg) under inert atmosphere, and the mixture was stirred at RT for 2 h under $H_2$ atmosphere (balloon pressure). After consumption of the starting material (by TLC), the reaction mixture was filtered through a pad of Celite® and washed with EtOAc (3×10 mL). The filtrate was concentrated under reduced pressure to afford 53 (23 mg, 0.05 mmol, 76%) as a brown semi-solid. $^1$H NMR (500 MHz, $CDCl_3$): δ 8.69 (s, 1H), 8.34 (s, 1H), 8.22 (s, 1H), 7.29-7.27 (m, 1H), 7.09-7.07 (m, 2H), 6.97-6.93 (m, 2H), 6.80-6.76 (m, 1H), 6.69-6.66 (m, 1H), 5.95 (d, J=14.5 Hz, 1H), 5.34 (d, J=14.5 Hz, 1H), 5.32 (s, OH), 3.15 (t, J=7.5 Hz, 2H), 3.05 (t, J=7.5 Hz, 2H). HPLC: 91.7%. MS (ESI): m/z 477 [M+H]$^+$.

Example 23

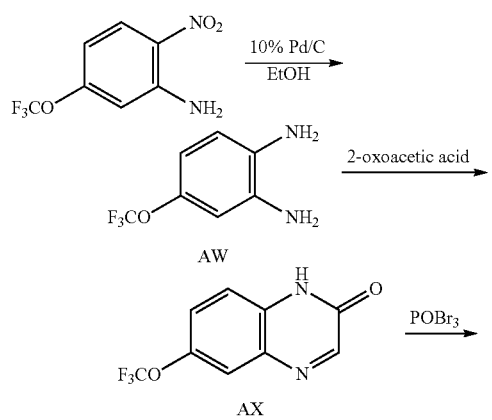

2-(2,4-Difluorophenyl)-1,1-difluoro-3-(1H-tetrazol-1-yl)-1-(6-(trifluoromethoxy)quinoxalin-2-yl)propan-2-ol (54)

To a stirred solution of 2-nitro-5-(trifluoromethoxy)aniline (5.0 g, 22.5 mmol) in EtOH (50 mL) was added 10% Pd/C (1.2 g) under inert atmosphere. The resulting reaction mixture was stirred for 16 h at RT under $H_2$ atmosphere. After consumption of the starting material (by TLC), the reaction mixture was filtered through a pad of Celite® and washed with EtOAc (3×50 mL). The filtrate was concentrated under reduced pressure to afford compound AW (4.0 g, 20.83 mmol, 93%) as an orange syrup. $^1$H NMR (500 MHz, DMSO-$d_6$): δ 6.50-6.45 (m, 2H), 6.29 (d, J=8.0 Hz, 1H), 4.76-4.75 (br s, 4H). MS (ESI): m/z 194 [M+2]$^+$.

To a stirred solution of compound AW (4.0 g, 20.83 mmol) in $CH_3OH$ (40 mL) was added 2-oxoacetic acid (2.3 mL, 20.83 mmol) at 0° C. The resulting reaction mixture was allowed to warm to RT and stirred for 24 h. After the consumption of starting material (by TLC), the reaction mixture was diluted with $H_2O$ (50 mL) and stirred for 5 min. The solid precipitated was filtered and washed with $H_2O$ (3×50 mL). The crude solid was purified by silica gel column chromatography (eluting with 30% EtOAc/hexane) to afford compound AX (1.4 g, 6.08 mmol, 29.8%) as pale-yellow solid. $^1$H NMR (500 MHz, DMSO-d$_6$): δ 12.6 (br s, 1H), 8.25 (s, 1H), 7.78 (s, 1H), 7.60 (d, J=7.0 Hz, 1H), 7.04 (d, J=8.5 Hz, 1H). MS (ESI): m/z 230 [M+H]$^+$.

To compound AX (0.85 g, 3.69 mmol) was added POBr$_3$ (2.1 g, 7.34 mmol) at RT. The reaction mixture was gradually heated to 130° C. and stirred for 2 h. After complete consumption of the starting material (by TLC), the reaction mixture was cooled to RT, diluted with ice cold H$_2$O (30 mL), made basic (pH ~8) using satd NaHCO$_3$ solution (25 mL) and extracted with EtOAc (2×50 mL). The combined organic extracts were washed with H$_2$O (50 mL) and brine (50 mL), dried over anhydrous Na$_2$SO$_4$ and concentrated under reduced pressure to obtain the crude material. Purification by silica gel column chromatography (eluting with 2% EtOAc/hexane) to afford compound AY (0.65 g, 2.22 mmol, 65%) as an off-white solid. $^1$H NMR (500 MHz, CDCl$_3$): δ 8.89 (s, 1H), 8.09 (d, J=9.0 Hz, 1H), 7.94 (s, 1H), 7.65 (dd, J=9.0, 2.0 Hz, 1H). MS (ESI): m/z 295.9 [M+2]$^+$.

To a stirred suspension of copper powder (0.56 g, 0.89 mmol) in DMSO (10 mL) was added ethyl 2-bromo-2,2-difluoroacetate (0.9 g, 4.45 mmol), and the mixture was stirred at RT for 1 h. To the resulting reaction mixture was added compound AY (0.65 g, 2.22 mmol), and stirring was continued for 16 h at RT. After complete consumption of the starting material (by TLC), the reaction mixture was quenched with satd NH$_4$Cl solution (100 mL) and extracted with EtOAc (3×30 mL). The combined organic extracts were washed with H$_2$O (50 mL) and brine (50 mL), dried over anhydrous Na$_2$SO$_4$ and concentrated under reduced pressure to obtain the crude material. Purification by silica gel column chromatography (eluting with 2% EtOAc/hexane) to afford ester AZ (0.55 g, 1.63 mmol, 73.6%) as a pale-yellow syrup. $^1$H NMR (500 MHz, CDCl$_3$): δ 9.26 (s, 1H), 8.21 (d, J=9.5 Hz, 1H), 8.02 (s, 1H), 7.71 (d, J=9.5 Hz, 1H), 4.42 (q, J=7.0 Hz, 2H), 1.36 (t, J=7.0 Hz, 3H).

To a stirred solution of 1-bromo-2,4-difluorobenzene (0.27 mL, 2.45 mmol) in Et$_2$O (5 mL) was added n-BuLi (1.6 M in hexane; 1.5 mL, 2.45 mmol) at −78° C., and the mixture was stirred for 30 min under inert atmosphere. A solution of ester AZ (0.55 g, 1.63 mmol) in THF (5 mL) was added to the reaction mixture at −78° C., and stirring was continued for another 1 h. After complete consumption of the starting material (by TLC), the reaction mixture was quenched with satd NH$_4$Cl solution (50 mL) and extracted with EtOAc (2×25 mL). The combined organic extracts were washed with H$_2$O (25 mL) and brine (25 mL), dried over anhydrous Na$_2$SO$_4$ and concentrated under reduced pressure to obtain the crude product. Purification by silica gel column chromatography (eluting with 5% EtOAc/hexane) to afford ketone BA (0.4 g, 0.98 mmol, 60%) as a yellow syrup. $^1$H NMR (500 MHz, CDCl$_3$): δ 9.34 (s, 1H), 8.12-8.11 (m, 2H), 8.03 (s, 1H), 7.67-7.65 (m, 1H), 7.07-7.05 (m, 1H), 6.83-6.79 (m, 1H). MS (ESI): 405 [M+H]$^+$.

To a stirred solution of ketone BA (0.4 g, 0.99 mmol) in Et$_2$O (15 mL) was added freshly prepared diazomethane [prepared by dissolving NMU (509 mg, 4.95 mmol) in a 1:1 mixture of 10% KOH solution (40 mL) and Et$_2$O (40 mL) at 0° C. followed by separation and drying of the organic layer using KOH pellets] at 0° C. and stirred for 30 min. The resulting reaction mixture was allowed to warm to RT, and stirring was continued for another 4 h. After complete consumption of the starting material (by TLC), the volatiles were evaporated under reduced pressure. The crude material was purified by silica gel column chromatography (eluting with 2% EtOAc/hexane) to afford epoxide BB (0.29 g, 0.69 mmol, 70%) as a yellow syrup. $^1$H NMR (500 MHz, CDCl$_3$): δ 9.02 (s, 1H), 8.22 (d, J=9.5 Hz, 1H), 8.00 (s, 1H), 7.70 (dd, J=9.5, 2.5 Hz, 1H), 7.46-7.43 (m, 1H), 6.89-6.85 (m, 1H), 6.78-6.74 (m, 1H), 3.46 (d, J=5.0 Hz, 1H), 3.03 (d, J=5.0 Hz, 1H). MS (ESI): 419 [M+H]$^+$.

To a stirred solution of epoxide BB (0.29 g, 0.69 mmol) in dry DMF (5 mL) was added the sodium salt of tetrazole (95 mg, 1.03 mmol) at RT under inert atmosphere. The resulting reaction mixture was gradually heated up to 65° C. and stirred for 16 h. After complete consumption of the starting material (by TLC), the reaction mixture was diluted with ice cold H$_2$O (30 mL) and extracted with EtOAc (2×25 mL). The combined organic extracts were dried over anhydrous Na$_2$SO$_4$ and concentrated under reduced pressure. The obtained crude material was purified by silica gel column chromatography (eluting with 30% EtOAc/hexane) to afford 54 (140 mg, 0.28 mmol, 41.4%) as an off-white solid. $^1$H NMR (500 MHz, CDCl$_3$): δ 9.04 (s, 1H), 8.72 (s, 1H), 8.13 (d, J=9.5 Hz, 1H), 8.00 (s, 1H), 7.73 (dd, J=9.5, 2.0 Hz, 1H), 7.30-7.28 (m, 1H), 6.80-6.78 (m, 1H), 6.69-6.68 (m, 1H), 5.73 (d, J=14.5 Hz, 1H), 5.67 (s, OH), 5.21 (d, J=14.5 Hz, 1H). HPLC: 98.3%. MS (ESI): m/z 489 [M+H]$^+$.

Compound 55 in Table 1 was prepared using the same conditions as compound 54 from commercially available starting materials or prepared intermediates (given in Table 1).

Example 24

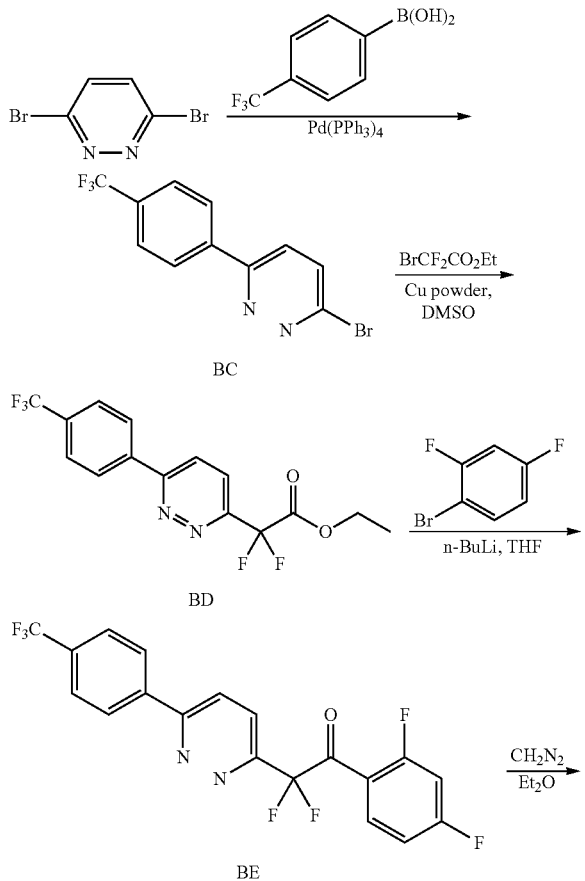

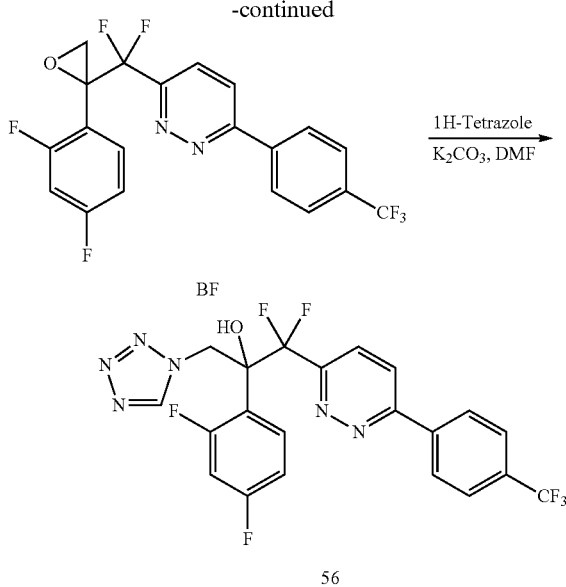

2-(2,4-Difluorophenyl)-1,1-difluoro-3-(1H-tetrazol-1-yl)-1-(6-(4-(trifluoromethyl)phenyl)pyridazin-3-yl)propan-2-ol (56)

To a stirred solution of 3,6-dibromopyridazine (200 mg, 0.84 mmol) and 4-(trifluoromethyl)phenylboronic acid (159.7 mg, 0.84 mmol) in 1,2-dimethoxyethane (DME; 12 mL) was added 1M sodium carbonate (Na$_2$CO$_3$; 1.2 mL, 1.26 mmol) at RT, and the mixture was degassed by purging with argon for 30 min. To the resulting reaction mixture was added tetrakis(triphenylphosphine)palladium(0) (Pd(PPh$_3$)$_4$; 29.1 mg, 0.025 mmol), and the mixture was further degassed for 5 min at RT. The reaction mixture was stirred at reflux for 18 h. After complete consumption of the starting material (by TLC), the reaction mixture was cooled to RT, diluted with H$_2$O (50 mL) and extracted with EtOAc (2×50 mL). The combined organic extracts were washed with H$_2$O (40 mL) and brine (40 mL), dried over anhydrous Na$_2$SO$_4$ and concentrated under reduced pressure to obtain the crude material. Purification by silica gel column chromatography (eluting with 12% EtOAc/hexane) afforded a mixture of mono and bis-coupled products BC (150 mg, 2:1 ratio), which was taken to the next step without separation. (Note: Both compounds eluted at same R$_f$; all the characteristic protons were seen in the $^1$H NMR spectrum.) MS (ESI): 303 [M+H]$^+$.

To a stirred suspension of copper powder (0.75 g, 11.81 mmol) in DMSO (3 mL) was added ethyl 2-bromo-2,2-difluoroacetate (1.2 g, 5.92 mmol) at RT, and the mixture was stirred for 1 h. A solution of compound BC (0.9 g, mixture) in DMSO (7 mL) was added to the reaction mixture, and stirring was continued for another 18 h at RT. After completion of reaction (by TLC), the reaction mixture was quenched with satd NH$_4$Cl solution (100 mL) and extracted with EtOAc (2×200 mL). The combined organic extracts were washed with H$_2$O (50 mL) and brine (50 mL), dried over anhydrous Na$_2$SO$_4$ and concentrated under reduced pressure to obtain the crude product. Purification by silica gel column chromatography (eluting with 15% EtOAc/hexane) afforded crude BD (0.7 g, as a mixture) which was taken for the next step without separation. (Note: All the characteristic protons were seen in the $^1$H NMR spectrum.) LC-MS: 347.8 [M+H]$^+$ at 4.99 RT (73.75% purity).

To a stirred solution of 1-bromo-2,4-difluorobenzene (83.67 mg, 0.43 mmol) in THF (5 mL) was added n-BuLi (1.6 M in hexane; 0.27 mL, 0.43 mmol) at −78° C. and stirred for 1 h under inert atmosphere. A solution of ester BD (100 mg, crude) in THF (3 mL) was added to the reaction mixture at −78° C., and stirring was continued for another 2 h. The progress of the reaction was monitored by TLC. The reaction was quenched with satd NH$_4$Cl solution (50 mL) and extracted with EtOAc (2×50 mL). The combined organic extracts were washed with H$_2$O (50 mL) and brine (50 mL), dried over anhydrous Na$_2$SO$_4$ and concentrated under reduced pressure to afford ketone BE (100 mg, crude). The mixture was taken on to the next step without purification.

(Note: All the characteristic protons were seen in $^1$H NMR spectrum.) MS (ESI): 415 [M+H]$^+$. To a stirred solution of ketone BE (100 mg, crude) in Et$_2$O (20 mL) was added freshly prepared diazomethane [prepared by dissolving NMU (240 mg, 2.41 mmol) in a 1:1 mixture of 10% KOH solution (40 mL) and Et$_2$O (40 mL) at 0° C. followed by separation and drying of the organic layer using KOH pellets] at 0° C., and the mixture was stirred for 1 h. The resulting reaction mixture was allowed to warm to RT, and stirring was continued for another 5 h. The progress of the reaction was monitored by TLC. The reaction mixture was concentrated under reduced pressure to afford BF (60 mg, crude). The obtained crude mixture was taken to the next step without purification. (Note: All the characteristic protons were seen in the $^1$H NMR spectrum.) MS (ESI): 429.9 [M+H]$^+$.

To a stirred solution of epoxide BF (60 mg, crude) in dry DMF (4 mL) was added 1H-tetrazole (19.25 mg, 0.27 mmol) followed by K$_2$CO$_3$ (19.25 mg, 0.14 mmol) at RT under an inert atmosphere. The resulting reaction mixture was gradually heated up to 65° C. and stirred for 20 h. The progress of the reaction was monitored by TLC. The reaction mixture was diluted with ice cold H$_2$O (50 mL) and extracted with EtOAc (2×50 mL). The combined organic extracts were washed with H$_2$O (50 mL) and brine (50 mL), dried over anhydrous Na$_2$SO$_4$ and concentrated under reduced pressure. The obtained crude material was purified by preparative TLC (eluting with 40% EtOAc/hexane; R$_f$=0.2) to afford 56 (11.5 mg, 0.02 mmol) as a colorless semi-solid. $^1$H NMR (500 MHz, CDCl$_3$): δ 8.80 (s, 1H), 8.19-8.17 (m, 2H), 8.01 (d, J=8.5 Hz, 1H), 7.83-7.81 (m, 3H), 7.41-7.37 (m, 1H), 6.80-6.68 (m, 3H), 5.70 (d, J=14.5 Hz, 1H), 5.28 (d, J=14.5 Hz, 1H). HPLC: 97.6%. MS (ESI): m/z 499.4 [M+H]$^+$.

Compounds 57 and 58 in Table 1 were prepared using the same conditions as compound 56 from commercially available starting materials (given in Table 1).

Example 25

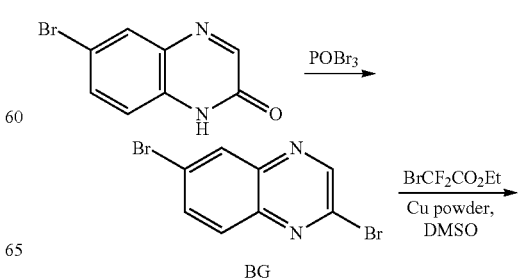

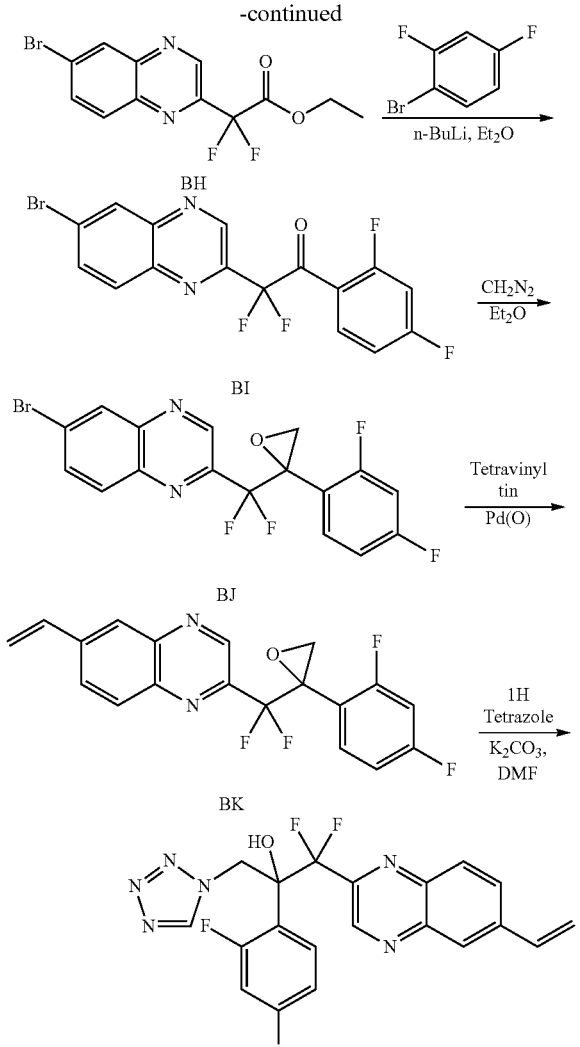

2-(2,4-Difluorophenyl)-1,1-difluoro-3-(1H-tetrazol-1-yl)-1-(6-vinylquinoxalin-2-yl)propan-2-ol (59)

To 6-bromoquinoxalin-2(1H)-one (1.0 g, 4.44 mmol) was added POBr$_3$ (2.54 g, 8.88 mmol) at RT. The reaction mixture was gradually heated to 130° C. and stirred for 2 h. After complete consumption of the starting material (by TLC), the reaction mixture was cooled to RT, neutralized with satd NaHCO$_3$ solution at 0° C. and extracted with EtOAc (2×100 mL). The combined organic extracts were washed with H$_2$O (100 mL) and brine (100 mL), dried over anhydrous Na$_2$SO$_4$ and concentrated under reduced pressure to obtain the crude product. Purification by silica gel column chromatography (eluting with 10% EtOAc/hexane) afforded compound BG (2.5 g, 9.0 mmol, 40%) as an off-white solid. $^1$H NMR (500 MHz, CDCl$_3$): δ 8.84 (s, 1H), 8.30 (d, J=9.0 Hz, 1H), 7.96-7.82 (m, 2H).

To a stirred suspension of copper powder (0.77 g, 12.1 mmol) in DMSO (15 mL) was added ethyl 2-bromo-2,2-difluoroacetate (1.23 g, 6.09 mmol) at RT, and the reaction mixture was stirred for 1 h. A solution of compound BG (0.85 g, 3.04 mmol) in DMSO (5 mL) was added to the reaction mixture, and stirring was continued for another 16 h at RT. After complete consumption of the starting material (by TLC), the reaction mixture was quenched with satd NH$_4$Cl solution (50 mL) and extracted with EtOAc (2×25 mL). The combined organic extracts were washed with H$_2$O (50 mL) and brine (50 mL), dried over anhydrous Na$_2$SO$_4$ and concentrated under reduced pressure to obtain the crude material. Purification by silica gel column chromatography (eluting with 20% EtOAc/hexane) afforded ester BH (0.53 g, 1.6 mmol, 53%) as an off-white solid. $^1$H NMR (500 MHz, CDCl$_3$): δ 9.22 (s, 1H), 8.34 (dd, J=8.0, 1.5 Hz, 1H), 8.02-7.94 (m, 2H), 4.40 (q, J=7.0 Hz, 2H), 1.36 (t, J=7.0 Hz, 3H). MS (ESI): m/z 332 [M+H]$^+$.

To a stirred solution of 1-bromo-2,4-difluorobenzene (0.32 g, 1.66 mmol) in Et$_2$O (30 mL) was added n-BuLi (1.6 M in hexane; 0.1 mL, 1.66 mmol) at −78° C., and the reaction mixture was stirred for 30 min under inert atmosphere. A solution of ester BH (0.55 g, 1.66 mmol) in Et$_2$O (10 mL) was added to the reaction mixture at −78° C., and stirring was continued for another 5 min. After complete consumption of the starting material (by TLC), the reaction mixture was quenched with satd NH$_4$Cl solution (50 mL) and extracted with EtOAc (2×25 mL). The combined organic extracts were washed with H$_2$O (25 mL) and brine (25 mL), dried over anhydrous Na$_2$SO$_4$ and concentrated under reduced pressure to obtain the crude product. Purification by silica gel column chromatography (eluting with 20% EtOAc/hexane) afford ketone BI (0.58 g, 1.46 mmol, 88%) as an off-white solid. $^1$H NMR (500 MHz, CDCl$_3$): δ 9.31 (s, 1H), 8.40 (s, 1H), 8.22-7.88 (m, 3H), 7.10-6.92 (m, 1H), 6.83-6.78 (m, 1H). MS (ESI): m/z 400 [M+H]$^+$.

To a stirred solution of ketone BI (0.59 g, 1.46 mmol) in Et$_2$O (10 mL) was added freshly prepared diazomethane [prepared by dissolving NMU (0.75 g, 7.3 mmol) in a 1:1 mixture of 10% KOH solution (20 mL) and Et$_2$O (20 mL) at 0° C. followed by separation and drying of the organic layer using KOH pellets] at 0° C., and the mixture was stirred for 30 min. The resulting reaction mixture was allowed to warm to RT, and stirring was continued for another 4 h. After complete consumption of the starting material (by TLC), the reaction mixture was concentrated under reduced pressure to afford the crude product. Purification by silica gel column chromatography (eluting with 10% EtOAc/hexane) afforded the epoxide BJ (0.53 g, 1.28 mmol, 88%) as a yellow syrup. $^1$H NMR (500 MHz, CDCl$_3$): δ 8.99 (s, 1H), 8.18 (s, 1H), 8.10-8.05 (m, 1H), 7.96-7.85 (m, 1H), 7.49-7.41 (m, 1H), 6.88-6.82 (m, 1H), 6.79-6.75 (m, 1H), 3.46 (d, J=5.0 Hz, 1H), 3.03 (d, J=5.0 Hz, 1H). MS (ESI): m/z 414 [M+H]$^+$.

A stirred solution of compound BJ (0.32 g, 0.72 mmol) and tetravinyltin (0.115 g, 0.72 mmol) in 1,4-dioxane (20 mL) was degassed by purging with inert gas for 10 min at RT. To the reaction mixture was added Pd(PPh$_3$)$_4$ (0.08 g, 0.073 mmol), and the mixture was degassed for another 10 min at RT. The reaction mixture was then stirred for 3 h at 70° C. After complete consumption of the starting material (by TLC), the reaction mixture was cooled to RT, filtered through a pad of Celite® and the filtrate was concentrated under reduced pressure to obtain the crude material. Purification by silica gel column chromatography (eluting with 7% EtOAc/hexane) afforded compound BK (0.15 g, 0.41 mmol, 57%) as a colorless liquid. This material contained some tin impurities and was used in the next step without further purification. $^1$H NMR (500 MHz, CDCl$_3$): δ 8.95 (s, 1H), 8.11-8.09 (m, 2H), 8.10 (d, J=9.5 Hz, 1H), 7.99-7.97 (m, 1H), 7.45-7.43 (m, 1H), 6.87-6.84 (m, 1H), 6.77-6.74 (m, 1H), 6.04 (d, J=17.5 Hz, 1H), 5.55 (d, J=11.5 Hz, 1H), 3.46 (d, J=5.0 Hz, 1H), 3.03 (d, J=5.0 Hz, 1H). MS (ESI): m/z 361 [M+H]$^+$.

To a stirred solution of epoxide BK (150 mg, 0.41 mmol) in dry DMF (10 mL) was added 1H-tetrazole (43 mg, 0.61 mmol) followed by K$_2$CO$_3$ (57 mg, 0.41 mmol) at RT under an inert atmosphere. The resulting reaction mixture was gradually heated up to 65° C. and stirred for 16 h. After complete consumption of the starting material (by TLC), the reaction mixture was diluted with ice-cold H$_2$O (30 mL) and extracted with EtOAc (2×30 mL). The combined organic extracts were washed with H$_2$O (30 mL) and brine (30 mL), dried over anhydrous Na$_2$SO$_4$ and concentrated under reduced pressure to obtain the crude product. Purification by silica gel column chromatography (eluting with 40% EtOAc/hexane) afforded 59 (35 mg, 0.08 mmol, 20%) as a colorless thick syrup. $^1$H NMR (500 MHz, CDCl$_3$): δ 8.98 (s, 1H), 8.74 (s, 1H), 8.06 (s, 1H), 8.02 (d, J=9.5 Hz, 2H), 7.31-7.29 (m, 1H), 6.96-6.93 (m, 1H), 6.80-6.76 (m, 1H), 6.65-6.63 (m, 1H), 6.22 (s, 1H), 6.06 (d, J=17.5 Hz, 1H), 5.71 (d, J=14.5 Hz, 1H), 5.60 (d, J=11 Hz, 1H) 5.21 (d, J=14.5 Hz, 1H). HPLC: 94%. MS (ESI): m/z 431 [M+H]$^+$.

Example 26

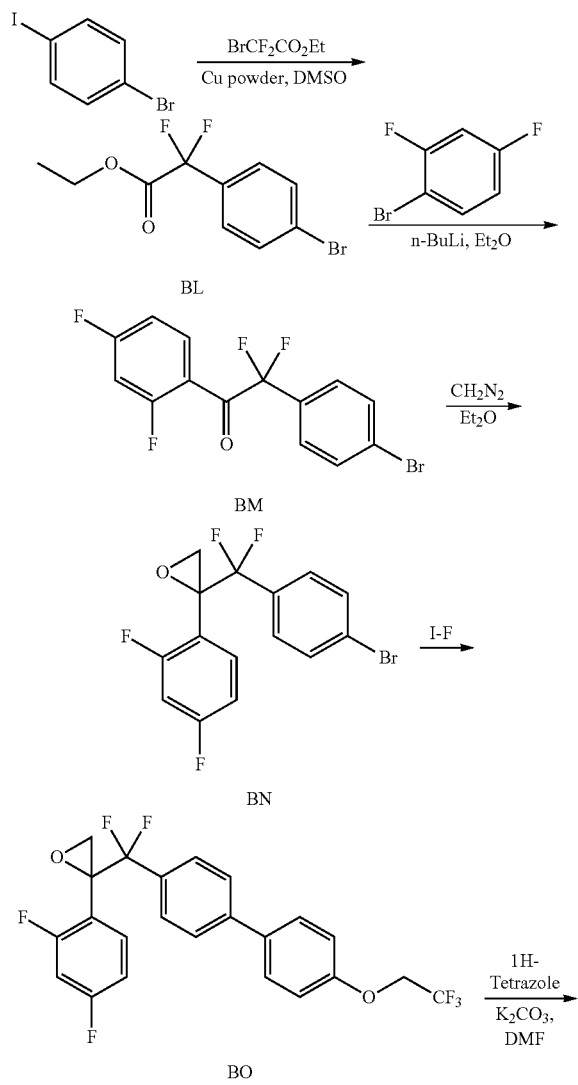

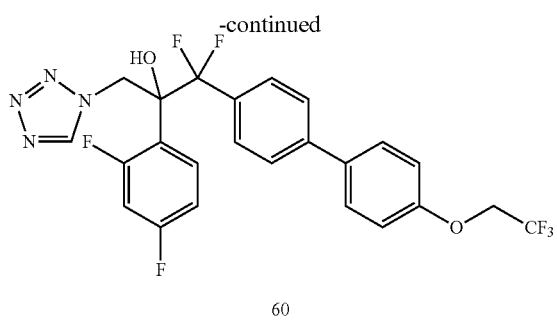

2-(2,4-Difluorophenyl)-1,1-difluoro-3-(1H-tetrazol-1-yl)-1-(4'-(2,2,2-trifluoroethoxy) biphenyl-4-yl) propan-2-ol (60)

To a suspension of copper powder (1.8 g, 28.3 mmol) in DMSO (20 mL) was added ethyl 2-bromo-2,2-difluoroacetate (1.8 mL, 14.13 mmol), and the mixture was stirred for 1 h at RT under an inert atmosphere. To the resulting solution was added 1-bromo-4-iodobenzene (2.0 g, 7.07 mmol), and stirring was continued for 10 h at RT. After complete consumption of the starting material (by TLC), the reaction mixture was quenched with satd NH$_4$Cl solution (30 mL) and extracted with CH$_2$Cl$_2$ (3×50 mL). The combined organic extracts were washed with H$_2$O (30 mL) and brine (30 mL), dried over anhydrous Na$_2$SO$_4$ and concentrated under reduced pressure to obtain the crude product. Purification by silica gel column chromatography (eluting with 2.5% EtOAc/hexane) afforded the ester BL (2.1 g, 7.53 mmol, 72%) as a liquid. $^1$H NMR (500 MHz, CDCl$_3$): δ 7.59 (d, J=9.0 Hz, 2H), 7.48 (d, J=9.0 Hz, 2H), 4.30 (q, J=7.0 Hz, 2H), 1.30 (t, J=7.0 Hz, 3H).

To a stirred solution of 1-bromo-2,4-difluorobenzene (0.2 mL, 1.79 mmol) in Et$_2$O (5 mL) was added n-BuLi (1.6 M in hexanes; 1.1 mL, 1.79 mmol) at −78° C., and the mixture was stirred for 30 min under inert atmosphere. A solution of ester BL (500 mg, 1.79 mmol) in Et$_2$O (5 mL) was added to the reaction mixture at −78° C., and stirring was continued for another 2 h. After complete consumption of the starting material (by TLC), the reaction mixture was quenched with satd NH$_4$Cl solution and extracted with CH$_2$Cl$_2$ (2×50 mL). The combined organic extracts were washed with H$_2$O (30 mL) and brine (30 mL), dried over anhydrous Na$_2$SO$_4$ and concentrated under reduced pressure to obtain the crude product. Purification by silica gel column chromatography (eluting with 3% EtOAc/hexane) afforded the ketone BM (400 mg, 1.15 mmol, 64%) as a pale-yellow liquid. $^1$H NMR (500 MHz, CDCl$_3$): δ 7.85-7.80 (m, 1H), 7.61 (d, J=8.5 Hz, 2H), 7.47 (d, J=8.5 Hz, 2H), 6.99-6.96 (m, 1H), 6.89-6.85 (m, 1H).

To a stirred solution of ketone BM (1.7 g, 4.91 mmol) in Et$_2$O (15 mL) was added freshly prepared diazomethane [prepared by dissolving NMU (2.5 g, 24.56 mmol) in a 1:1 mixture of 10% KOH solution (25 mL) and Et$_2$O (25 mL) at 0° C. followed by separation and drying of the organic layer using KOH pellets] at −5° C., and the mixture was stirred for 2 h. The resulting reaction mixture was allowed to warm to RT, and stirring was continued for another 16 h. Progress of the reaction was monitored by TLC. The reaction mixture was then concentrated under reduced pressure to obtain the crude product. Purification by silica gel column chromatography (eluting with 2-3% EtOAc/hexane) afforded the epoxide BN (1.5 g, 4.9 mmol, 88%) as a semi-solid. $^1$H NMR (200 MHz, CDCl₃): δ 7.55-7.51 (m, 2H), 7.29-7.21 (m, 3H), 7.86-6.71 (m, 2H), 3.25 (d, J=5.0 Hz, 1H), 2.97-2.91 (m, 1H).

To a stirred solution of epoxide BN (100 mg, 0.33 mmol) in THF-H₂O (15 mL, 8:2 v/v) were added sequentially Na₂CO₃ (90 mg, 0.83 mmol) and boronate I-F (120 mg, 0.33 mmol) at RT under an inert atmosphere. After purging with nitrogen for 10 min, Pd(dppf)₂Cl₂ (68 mg, 0.083 mmol) was added to reaction mixture under an inert atmosphere, and the resulting mixture was stirred at 70° C. for 4 h. The reaction mixture was allowed to cool to RT, diluted with H₂O (15 mL) and extracted with EtOAc (2×50 mL). The combined organic extracts were washed with H₂O (20 mL) and brine (20 mL), dried over anhydrous Na₂SO₄ and concentrated in vacuo. The crude material was purified by silica gel column chromatography (eluting with 3-4% EtOAc/hexane) to afford BO (110 mg, 0.26 mmol, 86%) as white solid. ¹H NMR (200 MHz, CDCl₃): δ 7.62-7.43 (m, 5H), 7.28-7.22 (m, 3H), 7.04-7.00 (m, 1H), 6.84-6.76 (m, 2H), 4.40 (q, J=8.0 Hz, 2H), 3.28 (dd, J=5.6, 2.0 Hz, 1H), 2.95-2.92 (m, 1H). MS (ESI): m/z 455 [M−H]⁻.

To a stirred solution of epoxide BO (120 mg, 0.26 mmol) in dry DMF (5 mL) was added 1H-tetrazole (28 mg, 0.39 mmol) followed by K₂CO₃ (73 mg, 0.52 mmol) at RT under an inert atmosphere. The resulting reaction mixture was gradually heated up to 65° C. and stirred for 8 h; progress of the reaction was monitored by TLC. The reaction mixture was then diluted with ice-cold H₂O and extracted with EtOAc (3×20 mL). The separated organic layer was washed with H₂O (50 mL) and brine (50 mL), dried over anhydrous Na₂SO₄ and concentrated under reduced pressure. The crude material was purified by silica gel column chromatography (eluting with 30% EtOAc/hexane) to afford 60 (20 mg, 0.04 mmol, 15%) as a pale-yellow solid. ¹H NMR (500 MHz, CDCl₃): δ 8.65 (s, 1H), 7.53 (d, J=9.0 Hz, 2H), 7.49 (d, J=7.5 Hz, 2H), 7.25 (d, J=8.0 Hz, 1H), 7.17-7.12 (m, 1H), 7.07-7.01 (m, 3H), 6.78-6.75 (m, 1H), 6.68-6.66 (m, 1H), 5.70 (d, J=14.5 Hz, 1H), 5.07 (d, J=14.5 Hz, 1H), 4.42-4.37 (q, J=8.0 Hz, 2H). MS (ESI): m/z 527 [M+H]⁺.

Compound 61 in Table 1 was prepared using the same conditions as compound 60 from commercially available starting materials (given in Table 1).

HPLC Method A Specifications
Column: Aquity BEH C-18 (50×2.1 mm, 1.7μ)
Mobile Phase: A) Acetonitrile; B) 0.025% aq TFA
Flow Rate: 0.50 mL/min
Time (min)/% B: 0.01/90, 0.5/90, 3/10, 6/10

TABLE 1

Structures for Example Compounds

| Compound Number | Structure | Starting Material |
|---|---|---|
| 1 | (structure) | See Example 1 |
| 2 | (structure) | See Example 2 |
| 3 | (structure) | See Example 3 |

TABLE 1-continued

Structures for Example Compounds

| Compound Number | Structure | Starting Material |
|---|---|---|
| 4 | 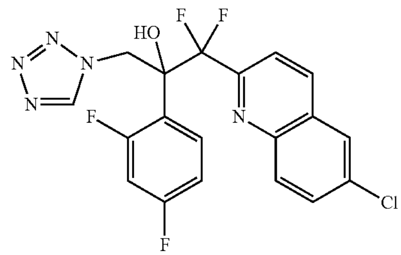 [SMILES: OC(Cn1cnnn1)(c1ccc(F)cc1F)C(F)(F)c1ccc2cc(Cl)ccc2n1] | See Example 4 |
| 5 | 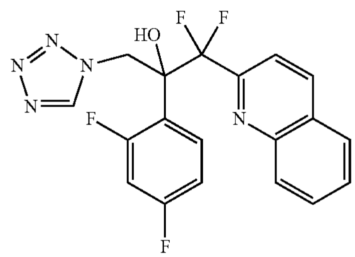 [SMILES: OC(Cn1cnnn1)(c1ccc(F)cc1F)C(F)(F)c1ccc2ccccc2n1] | See Example 5 |
| 6 | 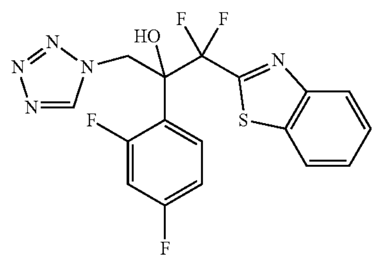 [SMILES: OC(Cn1cnnn1)(c1ccc(F)cc1F)C(F)(F)c1nc2ccccc2s1] | See Example 6 |
| 7 | 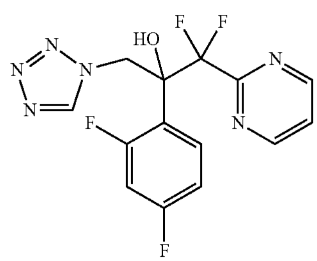 [SMILES: OC(Cn1cnnn1)(c1ccc(F)cc1F)C(F)(F)c1ncccn1] | See Example 7 |
| 8 | 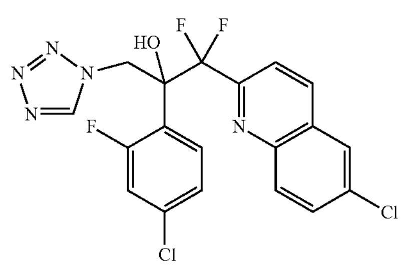 [SMILES: OC(Cn1cnnn1)(c1ccc(Cl)cc1F)C(F)(F)c1ccc2cc(Cl)ccc2n1] | See Example 8 |
| 9 | 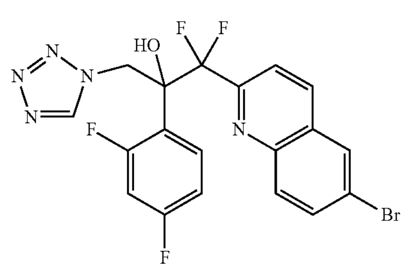 [SMILES: OC(Cn1cnnn1)(c1ccc(F)cc1F)C(F)(F)c1ccc2cc(Br)ccc2n1] | See Example 9 |

TABLE 1-continued
Structures for Example Compounds
| Compound Number | Structure | Starting Material |
|---|---|---|
| 10 | 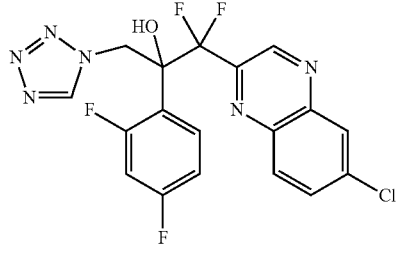 [SMILES: OC(Cn1cnnn1)(c1ccc(F)cc1F)C(F)(F)c1cnc2cc(Cl)ccc2n1] | See Example 10 |
| 11 | 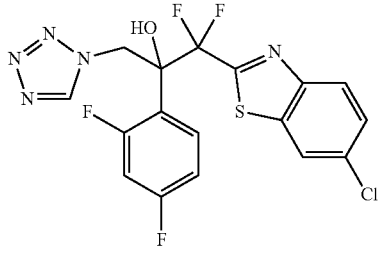 [SMILES: OC(Cn1cnnn1)(c1ccc(F)cc1F)C(F)(F)c1nc2ccc(Cl)cc2s1] | See Example 11 |
| 12 | 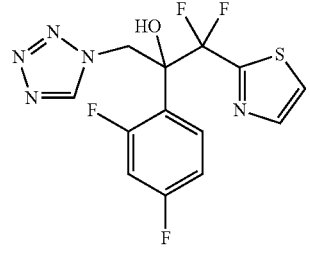 [SMILES: OC(Cn1cnnn1)(c1ccc(F)cc1F)C(F)(F)c1nccs1] | 2-bromothiazole |
| 13 | 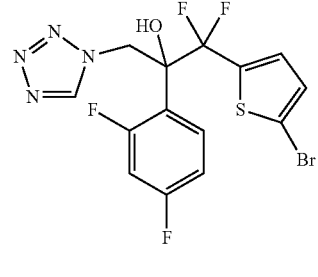 [SMILES: OC(Cn1cnnn1)(c1ccc(F)cc1F)C(F)(F)c1ccc(Br)s1] | 2,5-dibromothiophene |
| 14 | 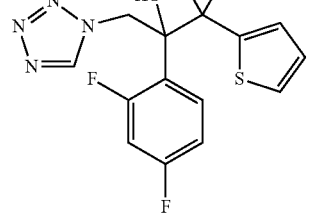 | 2-iodothiophene |

TABLE 1-continued

Structures for Example Compounds

| Compound Number | Structure | Starting Material |
|---|---|---|
| 15 | 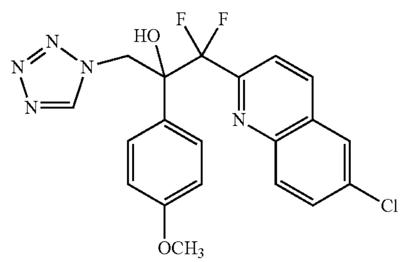 [SMILES: COc1ccc(C(O)(Cn2cnnn2)C(F)(F)c2ccc3cc(Cl)ccc3n2)cc1] | 1-bromo-4-methoxybenzene |
| 16 | 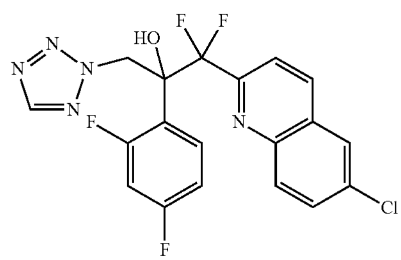 [SMILES: OC(Cn1ncnn1)(c1ccc(F)cc1F)C(F)(F)c1ccc2cc(Cl)ccc2n1] | 2-bromo-6-chloroquinoline; 2-bromo-6-chloroquinoline |
| 17 | 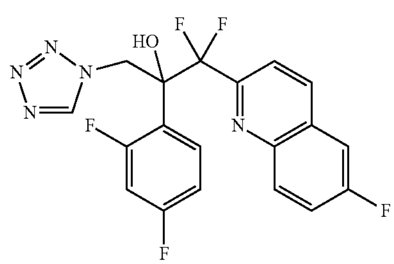 [SMILES: OC(Cn1cnnn1)(c1ccc(F)cc1F)C(F)(F)c1ccc2cc(F)ccc2n1] | 6-fluoroquinoline |
| 18 | 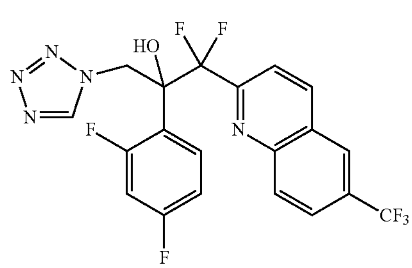 [SMILES: OC(Cn1cnnn1)(c1ccc(F)cc1F)C(F)(F)c1ccc2cc(C(F)(F)F)ccc2n1] | 6-(trifluoromethyl)quinoline |
| 19 | 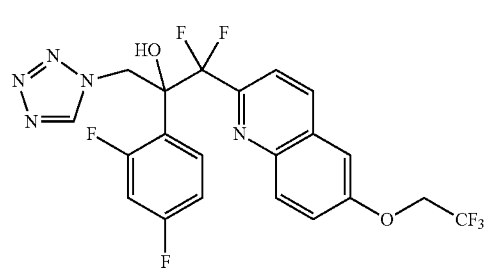 [SMILES: OC(Cn1cnnn1)(c1ccc(F)cc1F)C(F)(F)c1ccc2cc(OCC(F)(F)F)ccc2n1] | 2-bromo-6-(2,2,2-trifluoroethoxy)quinoline (I-A, Example 12) |

TABLE 1-continued

Structures for Example Compounds

| Compound Number | Structure | Starting Material |
|---|---|---|
| 20 | 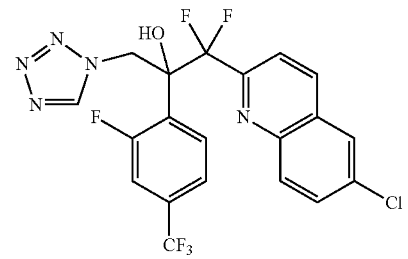 [SMILES: OC(Cn1cnnn1)(c1ccc(C(F)(F)F)cc1F)C(F)(F)c1ccc2cc(Cl)ccc2n1] | 1-bromo-2-fluoro-4-(trifluoromethyl)benzene; 2-bromo-6-chloroquinoline |
| 21 | 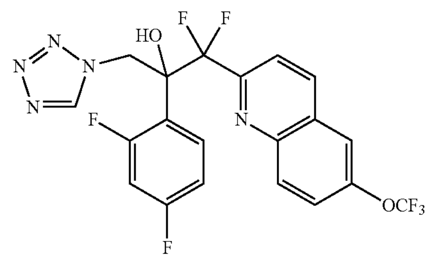 [SMILES: OC(Cn1cnnn1)(c1ccc(F)cc1F)C(F)(F)c1ccc2cc(OC(F)(F)F)ccc2n1] | 2-bromo-6-(trifluoromethoxy)quinoline (I-B, Example 12) |
| 22 | 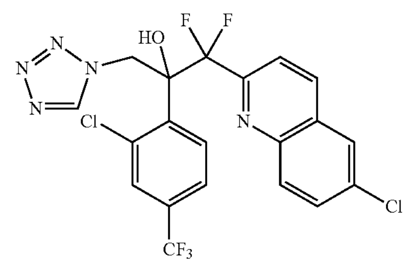 [SMILES: OC(Cn1cnnn1)(c1ccc(C(F)(F)F)cc1Cl)C(F)(F)c1ccc2cc(Cl)ccc2n1] | 1-bromo-2-chloro-4-(trifluoromethyl)benzene; 2-bromo-6-chloroquinoline |
| 23 | 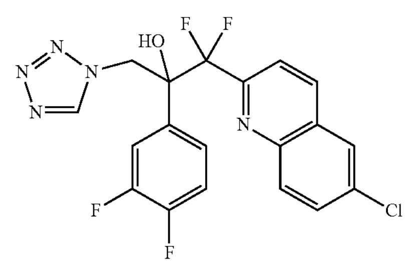 [SMILES: OC(Cn1cnnn1)(c1ccc(F)c(F)c1)C(F)(F)c1ccc2cc(Cl)ccc2n1] | 4-bromo-1,2-difluorobenzene; 2-bromo-6-chloroquinoline |
| 24 | 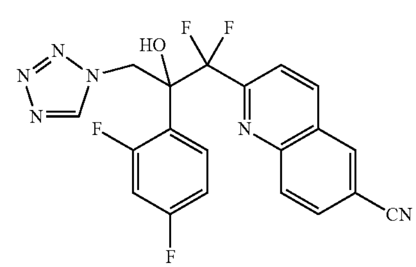 [SMILES: N#Cc1ccc2nc(C(F)(F)C(O)(Cn3cnnn3)c3ccc(F)cc3F)ccc2c1] | quinoline-6-carbonitrile (I-C, Example 12) |

TABLE 1-continued
Structures for Example Compounds
| Compound Number | Structure | Starting Material |
|---|---|---|
| 25 | 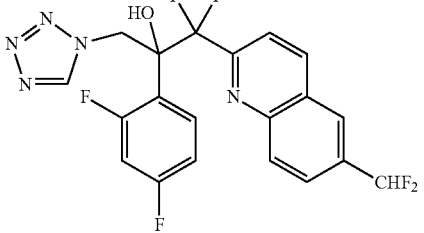 | 6-(difluoromethyl)quinoline (I-D, Example 12) |
| 26 | 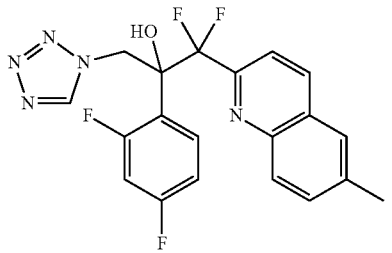 [SMILES: Cc1ccc2nc(C(F)(F)C(O)(Cn3cnnn3)c3ccc(F)cc3F)ccc2c1] | 6-methylquinoline |
| 27 | 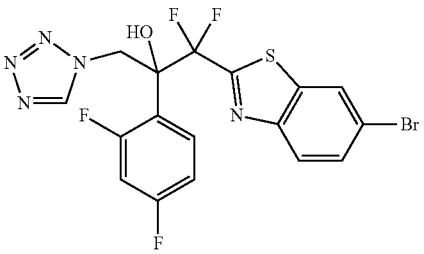 [SMILES: OC(Cn1cnnn1)(c1ccc(F)cc1F)C(F)(F)c1nc2ccc(Br)cc2s1] | 2,6-dibromobenzo[d]thiazole |
| 28 | 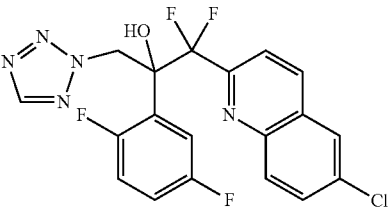 [SMILES: OC(Cn1ncnn1)(c1cc(F)ccc1F)C(F)(F)c1ccc2cc(Cl)ccc2n1] | 2-bromo-1,4-difluorobenzene; 2-bromo-6-chloroquinoline |
| 29 | 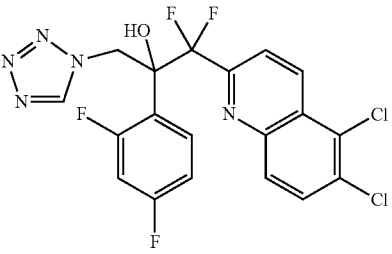 [SMILES: OC(Cn1cnnn1)(c1ccc(F)cc1F)C(F)(F)c1ccc2c(Cl)c(Cl)ccc2n1] | 5,6-dichloroquinoline |
| 30 | 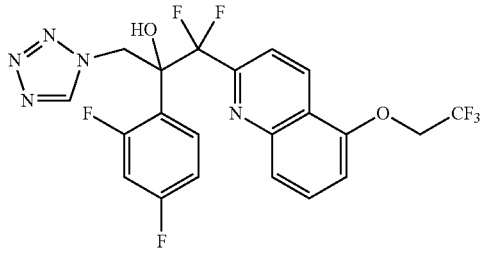 [SMILES: OC(Cn1cnnn1)(c1ccc(F)cc1F)C(F)(F)c1ccc2c(OCC(F)(F)F)cccc2n1] | 5-(2,2,2-trifluoroethoxy)quinoline (I-E, Example 12) |

TABLE 1-continued

Structures for Example Compounds

| Compound Number | Structure | Starting Material |
|---|---|---|
| 31 | 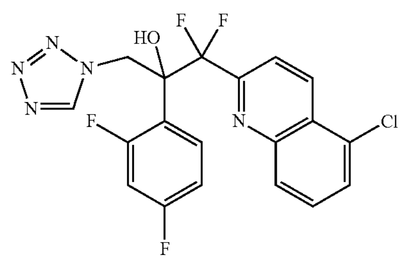 [SMILES: OC(Cn1cnnn1)(c1ccc(F)cc1F)C(F)(F)c1ccc2c(Cl)cccc2n1] | 5-chloroquinoline |
| 32 | 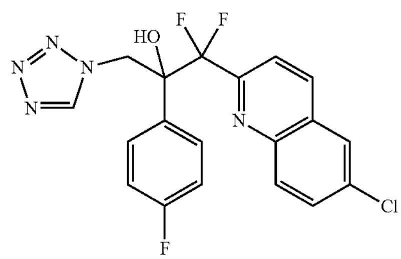 [SMILES: OC(Cn1cnnn1)(c1ccc(F)cc1)C(F)(F)c1ccc2cc(Cl)ccc2n1] | 1-bromo-4-fluorobenzene; 2-bromo-6-chloroquinoline |
| 33 | 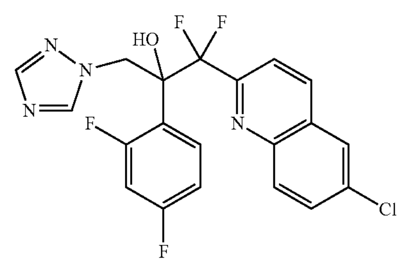 [SMILES: OC(Cn1cncn1)(c1ccc(F)cc1F)C(F)(F)c1ccc2cc(Cl)ccc2n1] | 1,2,4-triazole; 2-bromo-6-chloroquinoline |
| 34 | 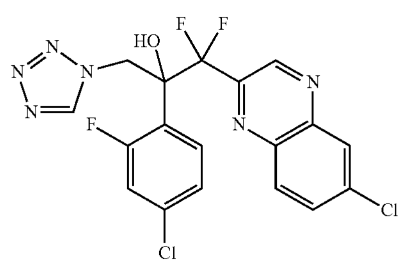 | 1-bromo-4-chloro-2-fluorobenzene; 2-bromo-6-chloroquinoxaline |
| 35 | 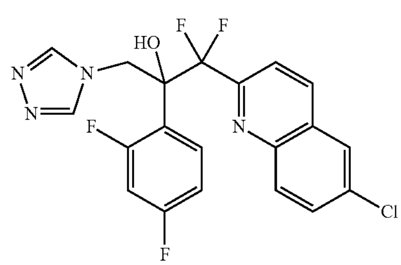 [SMILES: OC(Cn1cnnc1)(c1ccc(F)cc1F)C(F)(F)c1ccc2cc(Cl)ccc2n1] | See Example 13 |

TABLE 1-continued

Structures for Example Compounds

| Compound Number | Structure | Starting Material |
|---|---|---|
| 36 | 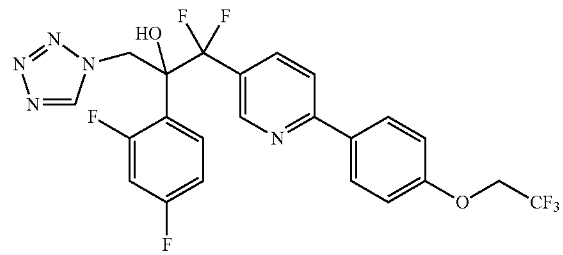 [SMILES: OC(Cn1cnnn1)(c1ccc(F)cc1F)C(F)(F)c1ccc(-c2ccc(OCC(F)(F)F)cc2)nc1] | See Example 14 |
| 37 | 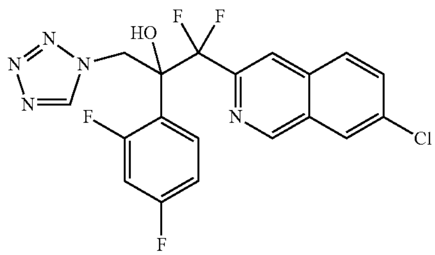 [SMILES: OC(Cn1cnnn1)(c1ccc(F)cc1F)C(F)(F)c1cc2ccc(Cl)cc2cn1] | See Example 15 |
| 38 | 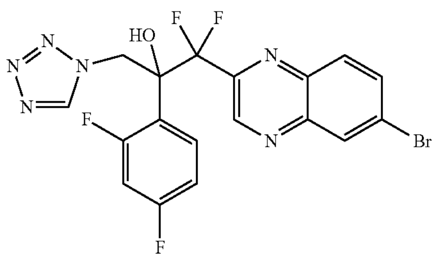 [SMILES: OC(Cn1cnnn1)(c1ccc(F)cc1F)C(F)(F)c1cnc2cc(Br)ccc2n1] | See Example 16 |
| 39 | 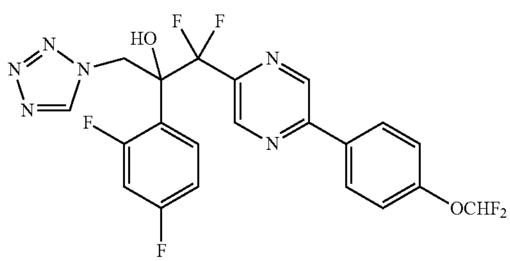 [SMILES: OC(Cn1cnnn1)(c1ccc(F)cc1F)C(F)(F)c1cnc(-c2ccc(OC(F)F)cc2)cn1] | See Example 17 |
| 40 | 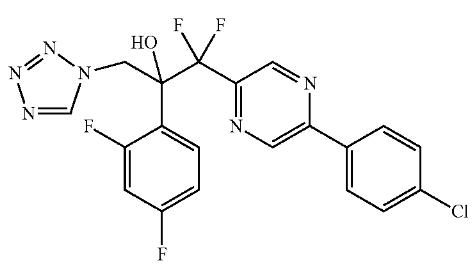 [SMILES: OC(Cn1cnnn1)(c1ccc(F)cc1F)C(F)(F)c1cnc(-c2ccc(Cl)cc2)cn1] | (4-chlorophenyl)boronic acid |
| 41 | 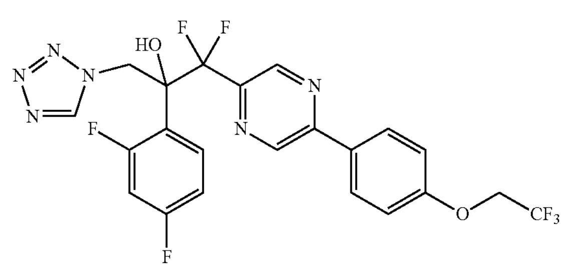 [SMILES: OC(Cn1cnnn1)(c1ccc(F)cc1F)C(F)(F)c1cnc(-c2ccc(OCC(F)(F)F)cc2)cn1] | 4,4,5,5-tetramethyl-2-(4-(2,2,2-trifluoroethoxy)phenyl)-1,3,2-dioxaborolane (I-F, Example 12) |

TABLE 1-continued

Structures for Example Compounds

| Compound Number | Structure | Starting Material |
|---|---|---|
| 42 | 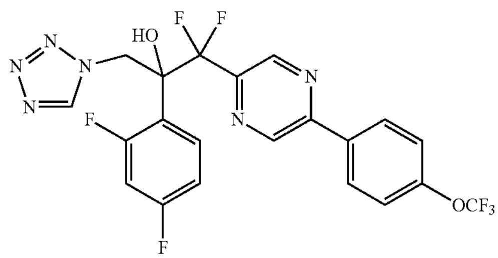 [SMILES: OC(Cn1cnnn1)(c1ccc(F)cc1F)C(F)(F)c1cnc(-c2ccc(OC(F)(F)F)cc2)cn1] | (4-(trifluoromethoxy)phenyl)boronic acid |
| 43 | 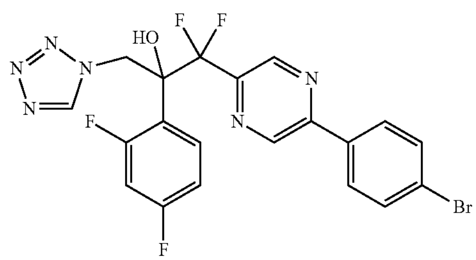 [SMILES: OC(Cn1cnnn1)(c1ccc(F)cc1F)C(F)(F)c1cnc(-c2ccc(Br)cc2)cn1] | (4-bromophenyl)boronic acid |
| 44 | 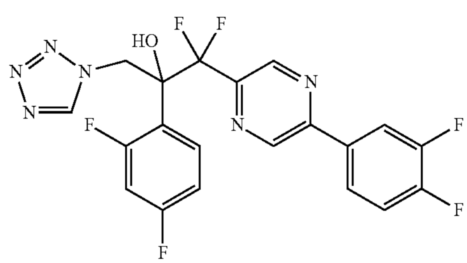 [SMILES: OC(Cn1cnnn1)(c1ccc(F)cc1F)C(F)(F)c1cnc(-c2ccc(F)c(F)c2)cn1] | (3,4-difluorophenyl)boronic acid |
| 45 | 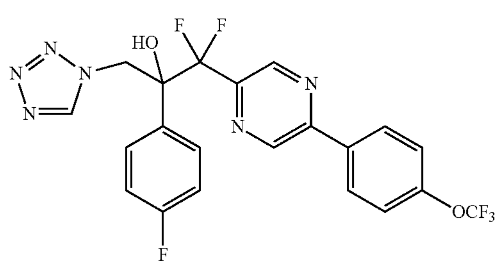 [SMILES: OC(Cn1cnnn1)(c1ccc(F)cc1)C(F)(F)c1cnc(-c2ccc(OC(F)(F)F)cc2)cn1] | 1-bromo-4-fluorobenzene |
| 46 | 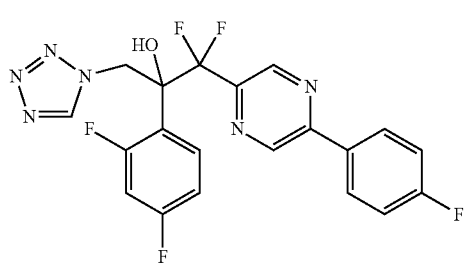 [SMILES: OC(Cn1cnnn1)(c1ccc(F)cc1F)C(F)(F)c1cnc(-c2ccc(F)cc2)cn1] | (4-fluorophenyl)boronic acid |

TABLE 1-continued
Structures for Example Compounds
| Compound Number | Structure | Starting Material |
|---|---|---|
| 47 | 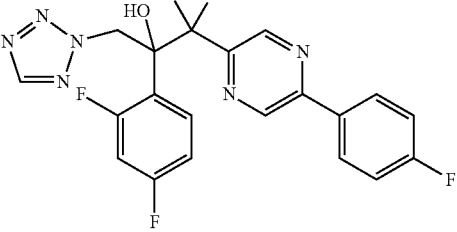 | (4-fluorophenyl)boronic acid |
| 48 | 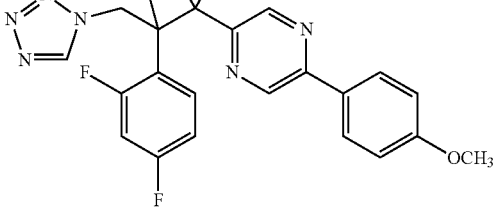 | (4-methoxyphenyl)boronic acid |
| 49 | 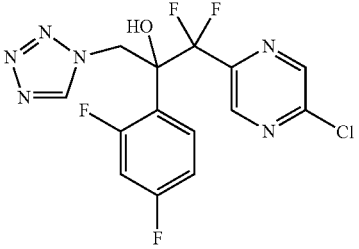 [SMILES: OC(Cn1cnnn1)(c1ccc(F)cc1F)C(F)(F)c1cnc(Cl)cn1] | See Example 19 |
| 50 | 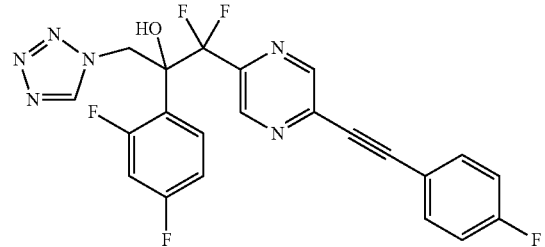 [SMILES: OC(Cn1cnnn1)(c1ccc(F)cc1F)C(F)(F)c1cnc(C#Cc2ccc(F)cc2)cn1] | See Example 20 |
| 51 | 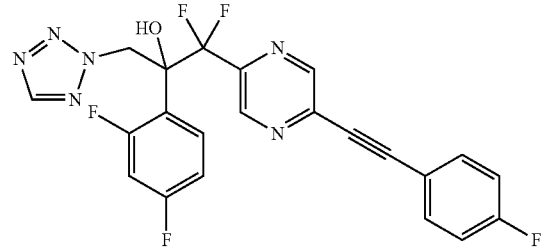 [SMILES: OC(Cn1ncnn1)(c1ccc(F)cc1F)C(F)(F)c1cnc(C#Cc2ccc(F)cc2)cn1] | See Example 20 |

TABLE 1-continued

Structures for Example Compounds

| Compound Number | Structure | Starting Material |
|---|---|---|
| 52 | 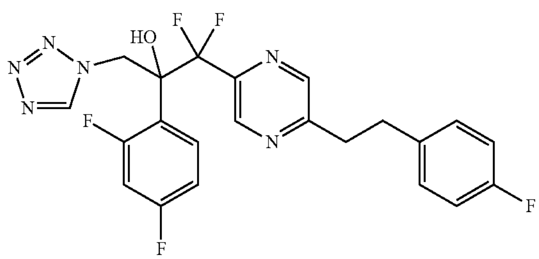 [SMILES: OC(Cn1cnnn1)(c1ccc(F)cc1F)C(F)(F)c1cnc(CCc2ccc(F)cc2)cn1] | See Example 21 |
| 53 | 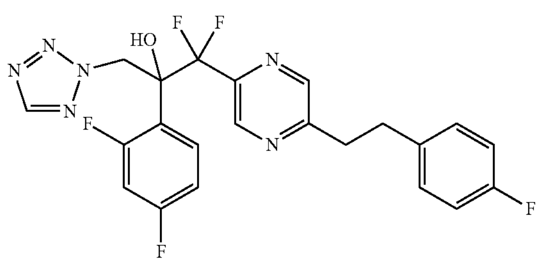 [SMILES: OC(Cn1ncnn1)(c1ccc(F)cc1F)C(F)(F)c1cnc(CCc2ccc(F)cc2)cn1] | See Example 22 |
| 54 | 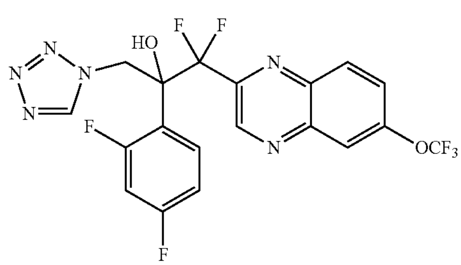 [SMILES: OC(Cn1cnnn1)(c1ccc(F)cc1F)C(F)(F)c1cnc2cc(OC(F)(F)F)ccc2n1] | See Example 23 |
| 55 | 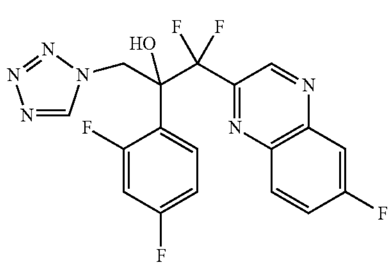 [SMILES: OC(Cn1cnnn1)(c1ccc(F)cc1F)C(F)(F)c1cnc2cc(F)ccc2n1] | 4-fluorobenzene-1,2-diamine |
| 56 | 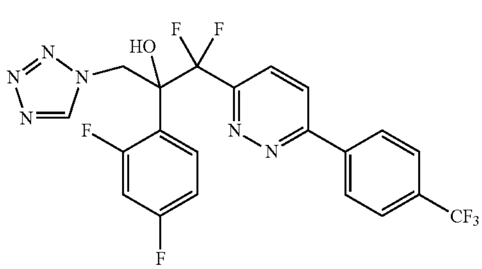 [SMILES: OC(Cn1cnnn1)(c1ccc(F)cc1F)C(F)(F)c1ccc(-c2ccc(C(F)(F)F)cc2)nn1] | See Example 24 |

TABLE 1-continued

Structures for Example Compounds

| Compound Number | Structure | Starting Material |
|---|---|---|
| 57 | 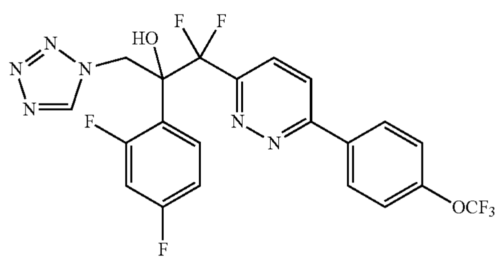 [SMILES: OC(Cn1cnnn1)(c1ccc(F)cc1F)C(F)(F)c1ccc(-c2ccc(OC(F)(F)F)cc2)nn1] | (4-(trifluoromethoxy)phenyl)boronic acid |
| 58 | 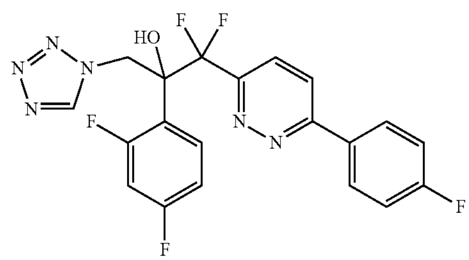 [SMILES: OC(Cn1cnnn1)(c1ccc(F)cc1F)C(F)(F)c1ccc(-c2ccc(F)cc2)nn1] | (4-fluorophenyl)boronic acid |
| 59 | 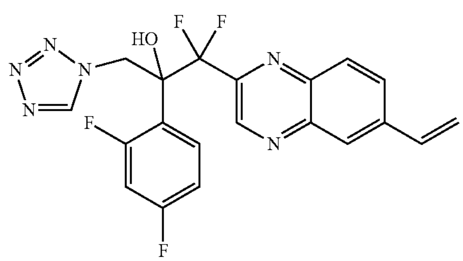 [SMILES: C=Cc1ccc2nc(C(F)(F)C(O)(Cn3cnnn3)c3ccc(F)cc3F)cnc2c1] | See Example 25 |
| 60 | 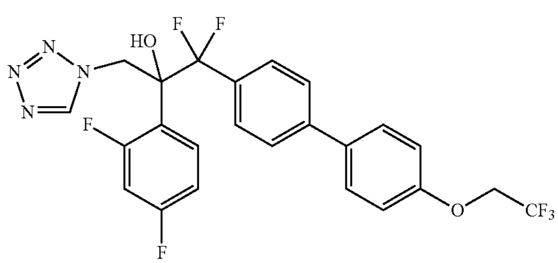 [SMILES: OC(Cn1cnnn1)(c1ccc(F)cc1F)C(F)(F)c1ccc(-c2ccc(OCC(F)(F)F)cc2)cc1] | See Example 26 |
| 61 | 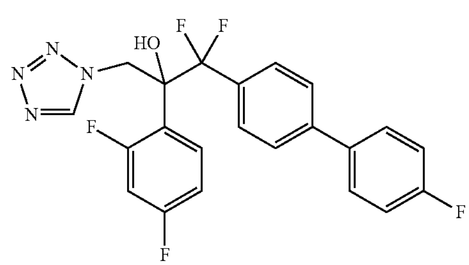 [SMILES: OC(Cn1cnnn1)(c1ccc(F)cc1F)C(F)(F)c1ccc(-c2ccc(F)cc2)cc1] | (4-fluorophenyl)boronic acid |

TABLE 2

Analytical Data for Example Compounds in Table 1

| Patent Example# | HPLC Method | HPLC Retention Time (min) | ESIMS (M + H) |
|---|---|---|---|
| 1 | A | 2.53 | 393 |
| 2 | A | 2.32 | 438 |
| 3 | A | 2.48 | 460.9 |
| 4 | A | 2.62 | 438 |
| 4(−) | A | 2.67 | 438 |
| 5 | A | 2.44 | 404 |
| 6 | A | 2.44 | 410 |
| 7 | A | 1.82 | 355 |
| 8(−) | A | 2.76 | 454 |
| 9(+) | A | 2.6 | 484 (M + 2) |
| 10(−) | A | 2.51 | 439 |
| 11 | A | 2.65 | 444.6 |
| 12 | A | 2.08 | 360 |
| 13 | A | 2.57 | 453 (M − 1) |
| 14 | A | 2.37 | 359 |
| 15 | A | 2.53 | 432 |
| 16 | A | 2.78 | 438 |
| 17 | A | 2.5 | 422 |
| 18 | A | 2.65 | 472 |
| 19 | A | 2.71 | 502 |
| 20 | A | 2.82 | 488 |
| 21 | A | 2.73 | 488 |
| 22 | A | 2.84 | 504.8 |
| 23 | A | 2.62 | 438 |
| 24 | A | 2.33 | 429 |
| 25 | A | 2.46 | 454 |
| 26 | A | 2.66 | 418.2 |
| 27 | A | 2.73 | 490.2 |
| 28 | A | 2.63 | 438 |
| 29 | A | 2.83 | 472.8 |
| 30 | A | 2.67 | 502.4 |
| 31 | A | 2.63 | 438 |
| 32 | A | 2.56 | 420 |
| 33(+) | A | 2.57 | 437 |
| 34 | A | 2.55 | 455 |
| 35 | A | 2.32 | 437 |
| 36 | A | 2.69 | 528 |
| 37 | A | 2.58 | 438 |
| 38 | A | 2.56 | 483 |
| 39 | A | 2.61 | 497 |
| 40 | A | 2.78 | 465.1 |
| 41 | A | 2.72 | 529 |
| 42 | A | 2.85 | 515 |
| 43 | A | 2.85 | 515.4 |
| 43(+) | A | 2.81 | 509 |
| 44 | A | 2.62 | 467.4 |
| 45 | A | 2.77 | 497.4 |
| 46 | A | 2.52 | 447.4 (M − 1) |
| 47 | A | 2.65 | 447.3 (M − 1) |
| 48 | A | 2.52 | 461.3 |
| 49 | A | 2.21 | 387.4 (M − 1) |
| 50 | A | 2.65 | 473.9 |
| 51 | A | 2.77 | 473.8 |
| 52 | A | 2.57 | 477.6 |
| 53 | A | 2.68 | 477 |
| 54 | A | 2.65 | 498.4 |
| 55 | A | 2.33 | 423.5 |
| 56 | A | 2.61 | 499.4 |
| 57 | A | 2.67 | 515.4 |
| 58 | A | 2.37 | 449.6 |
| 59 | A | 2.46 | 431.4 |
| 60 | A | 2.82 | 527 |
| 61 | A | 2.84 | |

Example 27

Metalloenzyme Activity

A. Minimum Inhibitory Concentration (MIC) (*C. albicans*)

Compounds of the present disclosure were assessed for their ability to inhibit the growth of common strains of fungus, *C. albicans* using a standardized procedure (CLSI M27-A2).

Stock solutions of the test compounds and standards were prepared in DMSO at 1,600 µg/mL (*C. albicans*). Eleven, serial, one-half dilutions of compounds were prepared in 96-well plates in RPMI+MOPS. The assay concentration ranges were 8-0.001 µg/mL (*C. albicans*). Cell suspensions of *C. albicans* were prepared and added to each well at concentrations of approximately $3.7 \times 10^3$ colony-forming-units per milliliter (cfu/mL). All testing was in duplicate. The inoculated plates were incubated for approximately 48 h at 35±1° C. At the completion of incubation the wells of each plate were evaluated visually for the presence of fungal growth.

For fluconazole and the test compounds, the MIC was the concentration at which growth was significantly reduced (about 50% reduction). For voriconazole the MIC was the concentration which reduced *C. albicans* growth by 50% (per CLS1, M27-A2). For QC purposes *C. krusei* isolate ATCC 6258 ($4.0 \times 10^3$ cfu/mL) was included in the VOR assay. This isolate did not exhibit trailing growth against voriconazole, therefore the MIC was the concentration at which growth was completely inhibited.

B. Inhibition of Liver Cytochrome P450 Enzymes

Solutions of each test compound were separately prepared at concentrations of 20000, 6000, 2000, 600, 200, and 60 µM by serial dilution with DMSO:MeCN (50:50 v/v). The individual test compound solutions were then diluted 20-fold with DMSO:MeCN:deionized water (5:5:180 v/v/v) to concentrations of 1000, 300, 100, 30, 10, and 3 µM. Mixtures of isozyme inhibitors (sulfaphenazole, tranylcypromine, and ketoconazole as specific inhibitors of isozymes 2C9, 2C19, and 3A4, respectively) were prepared containing each inhibitor at concentrations of 6000, 2000, 600, 200, 60, 20, 6, and 2 µM by serial dilution with DMSO:ACN (50:50 v/v). The mixed inhibitor solutions were then diluted 20-fold with DMSO:MeCN:deionized water (5:5:180 v/v/v) to concentrations of 300, 100, 30, 10, 3, 1, 0.3, and 0.1 µM. The percent of organic solvent attributable to the test compound or inhibitor mixture in the final reaction mixture was 2% v/v.

Pooled human liver microsome suspension (20 mg/mL) was diluted with phosphate buffer to obtain a 5 mg/mL suspension. A solution of NADPH was prepared in phosphate buffer at a concentration of 5 mM. Separate stock solutions of each substrate were prepared in DMSO:MeCN (50:50 v/v), mixed, and diluted in phosphate buffer to obtain a single solution containing each substrate at five times its experimentally determined $K_m$ concentration. The percent of organic solvent attributable to substrate mixture in the final reaction mixture was 1% v/v.

Substrate solution and microsome suspension were combined in a 1:1 volume ratio, mixed, and distributed to reaction wells of a PCR plate. Individual test compound or combined inhibitor solutions at each concentration were added to the wells and mixed by repetitive aspirate-dispense cycles. For active controls, blank phosphate buffer solution was added in place of test compound solution. Reaction mixtures were allowed to equilibrate at 37° C. for approximately two minutes before adding NADPH solution to initiate reaction, followed by pipette mixing of reaction mixture. Ten minutes after addition of NADPH, the reaction mixtures were quenched with cold acetonitrile. The samples were mixed by orbital shaking for approximately one minute and centrifuged at 2900 RCF for ten minutes. A portion of the supernatant was analyzed by gradient reverse-phase HPLC with detection by electrospray ionization triple quadrupole mass spectrometry in the positive ion mode.

Data was fitted to sigmoid dose-response curves and the inhibitory potency of each test compound was determined as its $IC_{50}$ value.

Results

| Example | Candida MIC* | CYP2C9 IC50 | CYP2C19 IC50 | CYP3A4 IC50 |
|---|---|---|---|---|
| 9 | 0.016 | 13 | 12 | 11 |
| 10 | 0.125 | 42 | 29 | 45 |
| Fluconazole | 0.5 | 29 | 8.2 | 8.0 |
| Voriconazole | 0.016 | 14 | 15 | 13 |

*Candida albicans* MICs are in μg/mL;
CYP IC50s are in μM.

C. Minimum Inhibitory Concentration (MIC) (*Septoria tritici*)

Compounds of the present disclosure were assessed for their ability to inhibit the growth of a common strain of the fungal plant pathogen *Septoria tritici* (ATCC 26517) using a procedure based on a Clinical and Laboratory Standards Institute (CLSI) microdilution assay protocol for filamentous fungi.

Stock solutions of the test compounds and standards were prepared in DMSO at 6400 μg/mL. Each stock solution was used to prepare a 2-fold dilution series ranging from 16 to 0.016 μg/mL (total of 11 compound concentrations) in RPMI-1640 (Roswell Park Memorial Institute) medium containing 3-(N-morpholino)propanesulfonic acid (MOPS) buffer and 2% DMSO. A 100 μL aliquot of the dilutions was added to columns 1 (16 μg/mL compound) through 11 (0.016 μg/mL compound) of a 96-well microtiter plate. This format was replicated in a second row of the microtiter plate. Thus, each microtiter plate could include 11 concentrations of four test or control compounds replicated twice. A 100 μL aliquot of RPMI-1640/MOPS/2% DMSO medium was added to column 12 (no compound control) of the microtiter plate.

A fresh culture of *S. tritici* was used to prepare a solution of approximately $5 \times 10^4$ colony-forming units per milliliter (cfu/mL) in RPMI/MOPS medium without DMSO. A 100 μL aliquot of this solution was added to all 96 wells in the microtiter plate. This results in final concentrations of each test or control compound of 8 μg/mL to 0.008 μg/mL in 200 μL of RPMI/MOPS media containing 1% DMSO and approximately $2.5 \times 10^4$ cfu/mL of *S. tritici*. The assay plates were incubated at 22° C. for seven days in the dark without shaking. The MIC for each compound was visually determined as the concentration which resulted in 50% reduction in the growth of *S. tritici* in comparison to the control (column 12).

In each case of Table 3 the rating scale is as follows:

| MIC (μg/mL | Rating |
|---|---|
| ≤0.5 | A |
| >0.5-1.5 | B |
| >1.5-4 | C |
| >4 | D |
| Not tested | E |

TABLE 3

MIC Data for Compounds in Table 1

| Patent Example# | Septoria Rating |
|---|---|
| 1 | E |
| 2 | C |
| 3 | E |
| 4 | A |
| 4(−) | A |
| 5 | E |
| 6 | A |
| 7 | E |
| 8(−) | A |
| 9(+) | A |
| 10(−) | A |
| 11 | A |
| 12 | D |
| 13 | A |
| 14 | B |
| 15 | C |
| 16 | B |
| 17 | A |
| 18 | A |
| 19 | B |
| 20 | B |
| 21 | A |
| 22 | C |
| 23 | A |
| 24 | A |
| 25 | A |
| 26 | A |
| 27 | A |
| 28 | A |
| 29 | A |
| 30 | C |
| 31 | C |
| 32 | A |
| 34 | A |
| 35 | C |
| 36 | C |
| 37 | A |
| 38 | A |
| 39 | A |
| 40 | B |
| 41 | A |
| 42 | A |
| 43 | A |
| 43(+) | A |
| 44 | B |
| 45 | C |
| 46 | B |
| 47 | D |
| 48 | A |
| 49 | E |
| 50 | A |
| 51 | C |
| 52 | A |
| 53 | C |
| 54 | C |
| 55 | C |
| 56 | B |
| 57 | A |
| 58 | C |
| 59 | B |
| 60 | C |
| 61 | B |

D. Evaluation of Fungicidal Activity vs. Leaf Rust (Causal Agent *Puccinia recondita tritici=Puccinia triticina*; Bayer code PUCCRT).

Wheat plants (variety Yuma) were grown from seed in a soil-less peat-based potting mixture (Metromix) until the seedlings had a fully expanded first leaf. Each pot contained 3-8 seedlings. These plants were sprayed until wet with the formulated test compounds. The compounds were formulated at 50 ppm in 10 vol. % acetone plus 90 vol. % Triton X water (deionized water 99.99 wt %+0.01 wt % Triton X100), giving a "formulated test compound." Formulated test compounds were applied to plants using a turn table sprayer fitted with two opposing air atomization nozzles which delivered approximately 1500 L/ha of spray volume. On the following day, the leaves were inoculated with an aqueous spore suspension of *Puccinia recondita* tritici and the plants were kept in high humidity overnight to permit spores to germinate and infect the leaf. The plants were then transferred to a greenhouse until disease developed on untreated control plants. Disease severity was evaluated 7-9 days later, depending on the speed of disease development. Compounds 4(−), 9(+), 11, 13, 18, 21, 25, 26, 27, 28, 32, 34, 37, 38, 39, 42, 43, 48, 51, 52, 56, 57, and 59 were selected for testing against PUCCRT at 50 ppm. Compounds that provided >80% disease control at 50 ppm included 4(−), 9(+), 11, 13, 18, 21, 25, 26, 27, 28, 32, 34, 37, 38, 39, 42, 43, 48, 52, 56, and 57.

Incorporation By Reference

The contents of all references (including literature references, issued patents, published patent applications, and co-pending patent applications) cited throughout this application are hereby expressly incorporated herein in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed:

1. A method of treating a metalloenzyme-mediated disease or disorder in or on a plant comprising contacting a compound of Formula I with the plant or seeds, wherein:

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ 1,1'-biphenyl substituted with 4'—$OCH_2CF_3$ or 4'-F, or heteroaryl, which may be optionally substituted with 1, 2 or 3 independent $R_5$;

$R_4$ is aryl, heteroaryl or cycloalkyl, optionally substituted with 0, 1, 2 or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo, haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —$Si(R_9)_3$, —$P(O)(OH)_2$, —$CH_2$—O—P(O)$(OH)_2$, or —C(O)alkyl optionally substituted with amino;

$R_9$ is independently alkyl or aryl;

wherein $R_3$ is not optionally substituted monocyclic pyridyl optionally substituted with 1, 2 or 3 independent $R_5$; and the metalloenzyme-related disorder or disease is mediated by lanosterol demethylase (CYP51).

2. A method of inhibiting metalloenzyme activity in a microorganism on a plant comprising contacting a compound of Formula I with the plant or seeds, wherein:

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —$Si(R_9)_3$, —$P(O)(OH)_2$, —$CH_2$—O—P(O)$(OH)_2$, or —C(O)alkyl optionally substituted with amino;

$R_9$ is independently alkyl or aryl;

wherein $R_3$ is not optionally substituted monocyclic pyridyl optionally substituted with 1, 2or 3 independent $R_5$; and wherein the metalloenzyme is lanosterol demethylase (CYP51).

3. A method of treating a fungal disease or disorder in or on a plant comprising contacting a compound of Formula I with the plant or seeds, wherein:

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2 or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$.

4. A method of treating fungal growth in or on a plant comprising contacting a compound of Formula I with the plant or seeds, wherein:

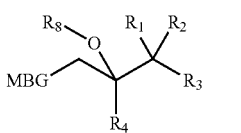

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;
$R_2$ is H, halo, alkyl or haloalkyl;
$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2 or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$.

5. A method of inhibiting microorganisms in or on a plant comprising contacting a compound of Formula I with the plant or seeds, wherein:

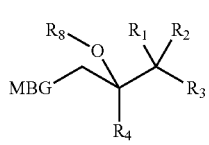

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2 or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$; and wherein the microorganism belongs to at least one genera selected from Blumeria, Podospaera, Sphaerotheca, Unicinula, Erysiphe, Puccinia, Phakopspora, Gymnosporangium, Hemileia, Uromyces, Alternia, Cercospora, Cladosporium, Cochliobolus, Colletotrichum, Magnaporthe, Mycosphaerella, Phaeosphaeria, Pyrenophora, Ramularia, Rhyncosporium, Septoria, Venturia, Ustilago, Aspergillus, Penicillium, Drechslera, Fusarium, Botrytis, Gibberella, Rhizoctonia, Pseudocercosporella, Sclerotinia, Helminithosporium, Stagonospora, Exserohilum, and Pyricularia.

6. A composition comprising a compound of Formula I or salt thereof, wherein:

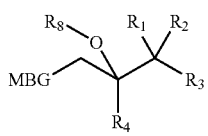

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2 or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$, said composition further comprising an azole fungicide selected from epoxiconazole, tebuconazole, fluquinconazole, flutriafol, metaconazole, myclobutanil, cycproconazole, prothioconazole and propiconazole.

7. A composition comprising a compound of Formula I, or salt thereof, wherein:

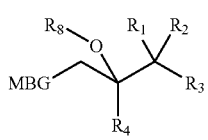

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$, said composition further comprising a strobilurin fungicide from the group trifloxystrobin, pyraclostrobin, orysastrobin, fluoxastrobin and azoxystrobin.

8. A method of inhibiting microorganisms in or on a plant comprising contacting a compound of Formula I with the plant or seeds, wherein:

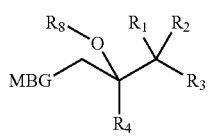

(I)

MBG is optionally substituted tetrazoyl, optionally substituted triazolyl, optionally substituted oxazolyl, optionally substituted pyrimidinyl, optionally substituted thiazolyl, or optionally substituted pyrazolyl;

$R_1$ is H, halo, alkyl or haloalkyl;

$R_2$ is H, halo, alkyl or haloalkyl;

$R_3$ is 1,1'-biphenyl substituted with 4'—$OCH_2CF_3$ or 4'—F, or heteroaryl, which may be optionally substituted with 1, 2 or 3 independent $R_5$;

$R_4$ is aryl, heteroaryl or cycloalkyl, optionally substituted with 0, 1, 2or 3 independent $R_6$;

each $R_5$ is independently H, halo, aryl optionally substituted 1, 2 or 3 independent $R_6$, heteroaryl, haloalkyl, haloalkoxy, cyano, nitro, alkyl, alkoxy, alkenyl, haloalkenyl, arylalkenyl, alkynyl, haloalkynyl, alklaryl, arylalkynyl, arylalkyl, cycloalklyl, halocycloalkyl, thioalkyl, $SF_3$, $SF_6$, SCN, $SO_2R_7$, C(O)alkyl, C(O)OH, C(O)Oalkyl;

each $R_6$ is independently alkyl, thioalkyl, cyano, haloalkyl, hydroxyl, alkoxy, halo haloalkoxy, —C(O)alkyl, —C(O)OH, —C(O)Oalkyl, $SF_3$, $SF_6$, SCN, $SO_3H$; and $SO_2R_7$;

$R_7$ is independently alkyl, aryl, substituted aryl, heteroaryl or substituted heteroaryl;

$R_8$ is H, —Si($R_9$)$_3$, —P(O)(OH)$_2$, —$CH_2$—O—P(O)(OH)$_2$, or —C(O)alkyl optionally substituted with amino;

$R_9$ is independently alkyl or aryl; and wherein $R_3$ is not optionally substituted monocyclic pyridyl optionally substituted with 1, 2 or 3 independent $R_5$; and wherein the microorganism is selected from the group consisting of Venturia inaequalis, Septoria tritici, Cercospora beticola, Cercospora arachidicola, Colletotrichum lagenarium, Puccinia graminis f. sp. tritici, Puccinia recondite tritici, Uncinula necoator, Blumeria grammis, and Mycosphaerella fijiensis.

9. The method of claim 3, wherein the fungal disease or disorder is selected from the group consisting of apple scab, speckled leaf blotch of wheat, leaf spot of sugarbeets, leaf spot of peanut, cucumber anthracnose, wheat leaf rust, grape powdery mildew, wheat powdery mildew, and black sigatoka.

10. The method of claim 4, wherein $R_1$ is fluoro.

11. The method of claim 4, wherein $R_2$ is fluoro.

12. The method of claim 4, wherein $R_1$ and $R_2$ are fluoro.

13. The method of claim 4, wherein $R_4$ is phenyl optionally substituted with 0, 1, 2 or 3 independent $R_6$.

14. The method of claim 4, wherein $R_4$ is phenyl optionally substituted with 0, 1, 2 or 3 independent halo.

15. The method of claim 4, wherein $R_4$ is phenyl optionally substituted with 0, 1, 2 or 3 independent fluoro.

16. The method of claim 4, wherein $R_1$ is 2,4-difluorophenyl.

17. The method of claim 4, wherein $R_5$ is halo.

18. The method of claim 4, wherein $R_3$ is heteroaryl optionally substituted with 1, 2 or 3 independent $R_5$; wherein at least one $R_5$ is halo.

19. The method of claim 4, wherein:
   $R_1$ is fluoro;
   $R_2$ is fluoro;
   $R_4$ is 2,4-difluorophenyl; and
   $R_3$ is heteroaryl other than 2-pyridyl, substituted with 1, 2 or 3 independent $R_5$.

20. The method of claim 4, wherein:
   $R_1$ is fluoro;
   $R_2$ is fluoro;
   $R_4$ is 2,4-difluorophenyl; and
   $R_3$ is bicyclic heteroaryl substituted with 1, 2 or 3 independent $R_5$.

21. The method of claim 4, wherein:
   $R_3$ is 2-quinolinyl substituted with 1, 2 or 3 independent $R_5$.

22. The method of claim 4, wherein the compound is one of:
   1-(5-Chlorothiophen-2-yl)-2-(2,4-difluorophenyl)-1,1-difluoro-3-(1H-tetrazol-1-yl)propan-2-ol (1);
   1-(4-Bromothiazol-2-yl)-2-(2,4-difluorophenyl)-1,1-difluoro-3-(1H-tetrazol-1-yl)propan-2-ol (2);
   4-(2-(2-(2,4-Difluorophenyl)-1,1-difluoro-2-hydroxy-3-(1H-tetrazol-1-yl)propyl)thiazol-4-yl)benzonitrile (3);
   1-(6-Chloroquinolin-2-yl)-2-(2,4-difluorophenyl)-1,1-difluoro-3-(1H-tetrazol-1-yl)propan-2-ol (4);
   2-(2,4-Difluorophenyl)-1,1-difluoro-1-(quinolin-2-yl)-3-(1H-tetrazol-1-yl)propan-2-ol (5);
   1-(Benzo[d]thiazol-2-yl)-2-(2,4-difluorophenyl)-1,1-difluoro-3-(1H-tetrazol-1-yl)propan-2-ol (6);
   2-(2,4-Difluorophenyl)-1,1-difluoro-1-(pyrimidin-2-yl)-3-(1H-tetrazol-1-yl)propan-2-ol (7);
   2-(4-Chloro-2-fluorophenyl)-1-(6-chloroquinolin-2-yl)-1,1-difluoro-3-(1H-tetrazol-1-yl)propan-2-ol (8);
   1-(6-Bromoquinolin-2-yl)-2-(2,4-difluorophenyl)-1,1-difluoro-3-(1H-tetrazol-1-yl)propan-2-ol (9);
   1-(6-Chloroquinoxalin-2-yl)-2-(2,4-difluorophenyl)-1,1-difluoro-3-(1H-tetrazol-1-yl)propan-2-ol (10);
   1-(6-Chlorobenzo[d]thiazol-2-yl)-2-(2,4-difluorophenyl)-1,1-difluoro-3-(1H-tetrazol-1-yl)propan-2-ol (11);
   2-(2,4-Difluorophenyl)-1,1-difluoro-3-(1H-tetrazol-1-yl)-1-(thiazol-2-yl)propan-2-ol (12);
   1-(5-Bromothiophen-2-yl)-2-(2,4-difluorophenyl)-1,1-difluoro-3-(1H-tetrazol-1-yl)propan-2-ol (13);
   2-(2,4-Difluorophenyl)-1,1-difluoro-3-(1H-tetrazol-1-yl)-1-(thiophen-2-yl)propan-2-ol (14);
   1-(6-Chloroquinolin-2-yl)-1,1-difluoro-2-(4-methoxyphenyl)-3-(1H-tetrazol-1-yl)propan-2-ol (15);
   1-(6-Chloroquinolin-2-yl)-2-(2,4-difluorophenyl)-1,1-difluoro-3-(2H-tetrazol-2-yl)propan-2-ol (16);
   2-(2,4-Difluorophenyl)-1,1-difluoro-1-(6-fluoroquinolin-2-yl)-3-(1H-tetrazol-1-yl)propan-2-ol (17);
   2-(2,4-Difluorophenyl)-1,1-difluoro-3-(1H-tetrazol-1-yl)-1-(6-(trifluoromethyl)quinolin-2-yl)propan-2-ol (18);
   2-(2,4-Difluorophenyl)-1,1-difluoro-3-(1H-tetrazol-1-yl)-1-(6-(2,2,2-trifluoroethoxy)quinolin-2-yl)propan-2-ol (19);
   1-(6-Chloroquinolin-2-yl)-1,1-difluoro-2-(2-fluoro-4-(trifluoromethyl)phenyl)-3-(1H-tetrazol-1-yl)propan-2-ol (20);
   2-(2,4-Difluorophenyl)-1,1-difluoro-3-(1H-tetrazol-1-yl)-1-(6-(trifluoromethoxy)quinolin-2-yl)propan-2-ol (21);
   2-(2-Chloro-4-(trifluoromethyl)phenyl)-1-(6-chloroquinolin-2-yl)-1,1-difluoro-3-(1H-tetrazol-1-yl)propan-2-ol (22);
   1-(6-Chloroquinolin-2-yl)-2-(3,4-difluorophenyl)-1,1-difluoro-3-(1H-tetrazol-1-yl)propan-2-ol (23);
   2-(2-(2,4-Difluorophenyl)-1,1-difluoro-2-hydroxy-3-(1H-tetrazol-1-yl)propyl)quinoline-6-carbonitrile (24);
   1-(6-(Difluoromethyl)quinolin-2-yl)-2-(2,4-difluorophenyl)-1,1-difluoro-3-(1H-tetrazol-1-yl)propan-2-ol (25);
   2-(2,4-Difluorophenyl)-1,1-difluoro-1-(6-methylquinolin-2-yl)-3-(1H-tetrazol-1-yl)propan-2-ol (26);
   1-(6-Bromobenzo[d]thiazol-2-yl)-2-(2,4-difluorophenyl)-1,1-difluoro-3-(1H-tetrazol-1-yl)propan-2-ol (27);
   1-(6-Chloroquinolin-2-yl)-2-(2,5-difluorophenyl)-1,1-difluoro-3-(2H-tetrazol-2-yl)propan-2-ol (28);
   1-(5,6-Dichloroquinolin-2-yl)-2-(2,4-difluorophenyl)-1,1-difluoro-3-(1H-tetrazol-1-yl)propan-2-ol (29);
   2-(2,4-Difluorophenyl)-1,1-difluoro-3-(1H-tetrazol-1-yl)-1-(5-(2,2,2-trifluoroethoxy)quinolin-2-yl)propan-2-ol (30);
   1-(5-Chloroquinolin-2-yl)-2-(2,4-difluorophenyl)-1,1-difluoro-3-(1H-tetrazol-1-yl)propan-2-ol (31);
   1-(6-Chloroquinolin-2-yl)-1,1-difluoro-2-(4-fluorophenyl)-3-(1H-tetrazol-1-yl)propan-2-ol (32);
   1-(6-Cloroquinolin-2-yl)-2-(2,4-difluorophenyl)-1,1-difluoro-3-(1H-1,2,4-triazol-1-yl)propan-2-ol (33);
   2-(4-Chloro-2-fluorophenyl)-1-(6-chloroquinoxalin-2-yl)-1,1-difluoro-3-(1H-tetrazol-1-yl)propan-2-ol (34);
   1-(6-Chloroquinolin-2-yl)-2-(2,4-difluorophenyl)-1,1-difluoro-3-(4H-1,2,4-triazol-4-yl)propan-2-ol (35);
   1-(7-Chloroisoquinolin-3-yl)-2-(2,4-difluorophenyl)-1,1-difluoro-3-(1H-tetrazol-1-yl)propan-2-ol (37);
   1-(6-Bromoquinoxalin-2-yl)-2-(2,4-difluorophenyl)-1,1-difluoro-3-(1H-tetrazol-1-yl)propan-2-ol (38);
   1-(5-(4-(Difluoromethoxy)phenyl)pyrazin-2-yl)-2-(2,4-difluorophenyl)-1,1-difluoro-3-(1H-tetrazol-1-yl)propan-2-ol (39);
   1-(5-(4-Chlorophenyl)pyrazin-2-yl)-2-(2,4-difluorophenyl)-1,1-difluoro-3-(1H-tetrazol-1-yl)propan-2-ol (40);
   2-(2,4-Difluorophenyl)-1,1-difluoro-3-(1H-tetrazol-1-yl)-1-(5-(4-(2,2,2-trifluoroethoxy)phenyl)pyrazin-2-yl)propan-2-ol (41);
   2-(2,4-Difluorophenyl)-1,1-difluoro-3-(1H-tetrazol-1-yl)-1-(5-(4-(trifluoromethoxy)phenyl)pyrazin-2-yl)propan-2-ol (42);
   1-(5-(4-Bromophenyl)pyrazin-2-yl)-2-(2,4-difluorophenyl)-1,1-difluoro-3-(1H-tetrazol-1-yl)propan-2-ol (43);
   2-(2,4-Difluorophenyl)-1-(5-(3,4-difluorophenyl)pyrazin-2-yl)-1,1-difluoro-3-(1H-tetrazol-1-yl)propan-2-ol (44);

1,1-Difluoro-2-(4-fluorophenyl)-3-(1H-tetrazol-1-yl)-1-(5-(4-(trifluoromethoxy)phenyl)pyrazin-2-yl)propan-2-ol (45);

2-(2,4-Difluorophenyl)-1,1-difluoro-1-(5-(4-fluorophenyl)pyrazin-2-yl)-3-(1H-tetrazol-1-yl)propan-2-ol (46);

2-(2,4-Difluorophenyl)-1,1-difluoro-1-(5-(4-fluorophenyl)pyrazin-2-yl)-3-(2H-tetrazol-2-yl)propan-2-ol (47);

2-(2,4-Difluorophenyl)-1,1-difluoro-1-(5-(4-methoxyphenyl)pyrazin-2-yl)-3-(1H-tetrazol-1-yl)propan-2-ol (48);

1-(5-Chloropyrazin-2-yl)-2-(2,4-difluorophenyl)-1,1-difluoro-3-(1H-tetrazol-1-yl)propan-2-ol (49);

2-(2,4-Difluorophenyl)-1,1-difluoro-1-(5-((4-fluorophenyl)ethynyl)pyrazin-2-yl)-3-(1H-tetrazol-1-yl)propan-2-ol (50);

2-(2,4-Difluorophenyl)-1,1-difluoro-1-(5-((4-fluorophenyl)ethynyl)pyrazin-2-yl)-3-(2H-tetrazol-2-yl)propan-2-ol (51);

2-(2,4-Difluorophenyl)-1,1-difluoro-1-(5-(4-fluorophenethyl)pyrazin-2-yl)-3-(1H-tetrazol-1-yl)propan-2-ol (52);

2-(2,4-Difluorophenyl)-1,1-difluoro-1-(5-(4-fluorophenethyl)pyrazin-2-yl)-3-(2H-tetrazol-2-yl)propan-2-ol (53);

2-(2,4-Difluorophenyl)-1,1-difluoro-3-(1H-tetrazol-1-yl)-1-(6-(trifluoromethoxy)quinoxalin-2-yl)propan-2-ol (54);

2-(2,4-Difluorophenyl)-1,1-difluoro-1-(6-fluoroquinoxalin-2-yl)-3-(1H-tetrazol-1-yl)propan-2-ol (55);

2-(2,4-Difluorophenyl)-1,1-difluoro-3-(1H-tetrazol-1-yl)-1-(6-(4-(trifluoromethyl)phenyl)pyridazin-3-yl)propan-2-ol (56);

2-(2,4-Difluorophenyl)-1,1-difluoro-3-(1H-tetrazol-1-yl)-1-(6-(4-(trifluoromethoxy)phenyl)pyridazin-3-yl)propan-2-ol (57);

2-(2,4-Difluorophenyl)-1,1-difluoro-1-(6-(4-fluorophenyl)pyridazin-3-yl)-3-(1H-tetrazol-1-yl)propan-2-ol (58);

2-(2,4-Difluorophenyl)-1,1-difluoro-3-(1H-tetrazol-1-yl)-1-(6-vinylquinoxalin-2-yl)propan-2-ol (59);

2-(2,4-Difluorophenyl)-1,1-difluoro-3-(1H-tetrazol-1-yl)-1-(4'-(2,2,2-trifluoroethoxy)-[1,1'-biphenyl]-4-yl)propan-2-ol (60);

2-(2,4-Difluorophenyl)-1,1-difluoro-1-(4'-fluoro-[1,1'-biphenyl]-4-yl)-3-(1H-tetrazol-1-yl)propan-2-ol (61).

\* \* \* \* \*